(12) United States Patent
Sundquist et al.

(10) Patent No.: US 10,736,689 B2
(45) Date of Patent: Aug. 11, 2020

(54) LOW-CORROSION ELECTRODE FOR TREATING TISSUE

(75) Inventors: Stephen K. Sundquist, Minnetonka, MN (US); Michael C. Holtz, Elk River, MN (US); Benjamin R. Fruland, Plymouth, MN (US); Tom A. Nelson, Elk River, MN (US); Kai Kroll, Plymouth, MN (US)

(73) Assignee: Prostacare Pty Ltd, Sydney (AU)

( * ) Notice: Subject to any disclaimer, the term of this patent is extended or adjusted under 35 U.S.C. 154(b) by 0 days.

(21) Appl. No.: 12/544,119

(22) Filed: Aug. 19, 2009

(65) Prior Publication Data

US 2011/0106072 A1 May 5, 2011

Related U.S. Application Data

(60) Provisional application No. 61/090,594, filed on Aug. 20, 2008, provisional application No. 61/090,519, (Continued)

(51) Int. Cl.
*A61B 18/00* (2006.01)
*A61B 18/14* (2006.01)
(Continued)

(52) U.S. Cl.
CPC ...... *A61B 18/1492* (2013.01); *A61B 18/1206* (2013.01); *A61B 18/16* (2013.01);
(Continued)

(58) Field of Classification Search
CPC ............... A61B 18/1492; A61B 19/56; A61B 2018/00285; A61B 2018/00547;
(Continued)

(56) References Cited

U.S. PATENT DOCUMENTS 3,698,394 A * 10/1972 Piper et al. ............... 606/29
3,933,616 A * 1/1976 Beer ..................... 204/290.12
(Continued)

FOREIGN PATENT DOCUMENTS

EP 1080731 A2 3/2001
EP 2 326 273 6/2011
(Continued)

OTHER PUBLICATIONS

Reis A, Henninger T. Zerstorung maligner Wachstumsenergie durch anodische Oxydation. Kim Wochenschrift 1951; _: 39.
(Continued)

*Primary Examiner* — Daniel W Fowler
(74) *Attorney, Agent, or Firm* — Patterson Thuente Pedersen, P.A.

(57) ABSTRACT

A non-implantable minimally invasive system for treatment of tissue in a body via direct current ablation is provided. A low-corrosion electrode for use with such system is further provided. In one embodiment the electrode includes a catheter end configured for coupling to a catheter, a tip configured for puncturing the tissue, and a length extending between the catheter and the tip. The length includes an active portion and an insulated portion. The active portion is electrically conductive and is between approximately 3 mm and approximately 12 mm long at an inserted portion of the electrode. The length further comprises an inner core formed of a material having a high resistance to deformation and an outer shell formed of a material having a high resistance to material decomposition.

23 Claims, 39 Drawing Sheets

Related U.S. Application Data filed on Aug. 20, 2008, provisional application No. 61/090,600, filed on Aug. 20, 2008, provisional application No. 61/090,589, filed on Aug. 20, 2008.

(51) Int. Cl.

| | | |
|---|---|---|
| *A61B 34/00* | (2016.01) | |
| *A61B 18/12* | (2006.01) | |
| *A61B 18/16* | (2006.01) | |
| *A61B 18/18* | (2006.01) | |
| *A61N 1/36* | (2006.01) | |
| *A61B 5/055* | (2006.01) | |
| *A61B 8/08* | (2006.01) | |
| *A61B 90/00* | (2016.01) | |

(52) U.S. Cl.
CPC .......... *A61B 18/1815* (2013.01); *A61B 34/25* (2016.02); *A61N 1/36071* (2013.01); *A61B 5/055* (2013.01); *A61B 8/08* (2013.01); *A61B 2018/0022* (2013.01); *A61B 2018/00083* (2013.01); *A61B 2018/00148* (2013.01); *A61B 2018/00285* (2013.01); *A61B 2018/00547* (2013.01); *A61B 2018/00577* (2013.01); *A61B 2018/00702* (2013.01); *A61B 2018/00755* (2013.01); *A61B 2018/00767* (2013.01); *A61B 2018/00791* (2013.01); *A61B 2018/00875* (2013.01); *A61B 2018/00982* (2013.01); *A61B 2018/00988* (2013.01); *A61B 2018/1266* (2013.01); *A61B 2018/143* (2013.01); *A61B 2018/1467* (2013.01); *A61B 2018/1475* (2013.01); *A61B 2018/1861* (2013.01); *A61B 2090/378* (2016.02); *A61B 2218/002* (2013.01)

(58) Field of Classification Search
CPC .. A61B 2018/00577; A61B 2018/1266; A61B 2018/143; A61B 2018/1475; A61B 2019/5276; A61B 5/055; A61B 8/08
USPC .............................................. 606/27, 34, 41
See application file for complete search history.

(56) References Cited

U.S. PATENT DOCUMENTS

| | | | |
|---|---|---|---|
| 4,003,379 A | 1/1977 | Ellinwood, Jr. | |
| 4,026,304 A | 5/1977 | Levy | |
| 4,289,135 A | 9/1981 | Nordenstrom et al. | |
| 4,572,214 A | 2/1986 | Nordenstrom et al. | |
| 4,639,244 A | 1/1987 | Rizk et al. | |
| 4,679,561 A | 7/1987 | Doss | |
| 4,682,596 A | 7/1987 | Bales et al. | |
| 4,721,123 A | 1/1988 | Cosentino et al. | |
| 4,919,138 A | 4/1990 | Nordenstrom | |
| 4,974,595 A | 12/1990 | Nordenstrom | |
| 5,002,558 A | 3/1991 | Klein et al. | |
| 5,026,371 A * | 6/1991 | Rydell et al. .................... 606/47 | |
| 5,058,605 A | 10/1991 | Slovak | |
| 5,084,154 A * | 1/1992 | Wakizoe ............. C25B 11/0478 | |
| | | | 204/290.13 |
| 5,098,843 A | 3/1992 | Calvin | |
| 5,281,218 A * | 1/1994 | Imran ............................. 606/41 | |
| 5,304,214 A | 4/1994 | DeFord et al. | |
| 5,314,451 A | 5/1994 | Mulier | |
| 5,314,457 A | 5/1994 | Jeutter et al. | |
| 5,370,675 A * | 12/1994 | Edwards et al. .............. 607/101 | |
| 5,431,625 A | 7/1995 | Fabian et al. | |
| 5,458,627 A | 10/1995 | Baranowski | |
| 5,482,054 A * | 1/1996 | Slater et al. ................. 600/564 | |
| 5,501,662 A | 3/1996 | Hofmann | |
| 5,507,724 A | 4/1996 | Hofmann et al. | |
| 5,529,574 A | 6/1996 | Frackelton | |
| 5,536,240 A * | 7/1996 | Edwards ................ A61B 18/00 | |
| | | | 604/22 |
| 5,536,267 A | 7/1996 | Edwards et al. | |
| 5,558,673 A * | 9/1996 | Edwards ............ A61B 18/1477 | |
| | | | 606/41 |
| 5,584,872 A | 12/1996 | LaFontaine et al. | |
| 5,611,350 A | 3/1997 | John | |
| 5,630,426 A | 5/1997 | Eggers et al. | |
| 5,672,153 A * | 9/1997 | Lax .................... A61B 10/0233 | |
| | | | 604/22 |
| 5,674,267 A | 10/1997 | Mir et al. | |
| 5,680,860 A * | 10/1997 | Imran ................. A61B 18/1492 | |
| | | | 600/374 |
| 5,701,895 A | 12/1997 | Prutchi et al. | |
| 5,718,686 A | 2/1998 | Davis | |
| 5,807,306 A | 9/1998 | Shapland et al. | |
| 5,810,764 A * | 9/1998 | Eggers et al. .................... 604/23 | |
| 5,820,548 A | 10/1998 | Sieben et al. | |
| 5,868,741 A * | 2/1999 | Chia et al. ..................... 606/41 | |
| 5,869,326 A | 2/1999 | Hofmann | |
| 5,919,187 A | 7/1999 | Guglielmi et al. | |
| 5,931,858 A | 8/1999 | Mackey | |
| 5,983,131 A | 11/1999 | Weaver et al. | |
| 5,985,305 A | 11/1999 | Peery et al. | |
| 5,993,434 A | 11/1999 | Dev et al. | |
| 6,009,345 A | 12/1999 | Hofmann | |
| 6,016,452 A * | 1/2000 | Kasevich ....................... 607/101 | |
| 6,021,347 A | 2/2000 | Herbst et al. | |
| 6,023,638 A | 2/2000 | Swanson | |
| 6,049,733 A | 4/2000 | Phipps et al. | |
| 6,051,017 A | 4/2000 | Loeb et al. | |
| 6,162,219 A * | 12/2000 | Nilsson et al. .................. 606/41 | |
| 6,165,206 A | 12/2000 | Tu | |
| 6,169,924 B1 | 1/2001 | Meloy et al. | |
| 6,171,787 B1 | 1/2001 | Wiley | |
| 6,174,309 B1 * | 1/2001 | Wrublewski et al. ........... 606/45 | |
| 6,179,833 B1 | 1/2001 | Taylor | |
| 6,238,393 B1 | 5/2001 | Mulier et al. | |
| 6,245,068 B1 * | 6/2001 | Olson et al. .................... 606/41 | |
| 6,269,270 B1 | 7/2001 | Boveja | |
| 6,273,886 B1 | 8/2001 | Edwards | |
| 6,278,895 B1 | 8/2001 | Bernard | |
| 6,366,808 B1 | 4/2002 | Schroeppel et al. | |
| 6,387,075 B1 | 5/2002 | Stivland et al. | |
| 6,391,026 B1 | 5/2002 | Hung et al. | |
| 6,402,745 B1 * | 6/2002 | Wilk ................................ 606/41 | |
| 6,419,673 B1 | 7/2002 | Edwards et al. | |
| 6,464,699 B1 * | 10/2002 | Swanson ........................ 606/41 | |
| 6,591,133 B1 | 7/2003 | Joshi | |
| 6,595,989 B1 * | 7/2003 | Schaer .......................... 606/41 | |
| 6,599,274 B1 | 7/2003 | Kucharczyk et al. | |
| 6,600,953 B2 | 7/2003 | Flesler et al. | |
| 6,607,528 B1 | 8/2003 | Quick et al. | |
| 6,626,899 B2 * | 9/2003 | Houser et al. .................. 606/14 | |
| 6,638,273 B1 | 10/2003 | Farley et al. | |
| 6,638,275 B1 * | 10/2003 | McGaffigan ....... A61B 18/1477 | |
| | | | 606/41 |
| 6,708,066 B2 | 3/2004 | Herbst et al. | |
| 6,713,291 B2 | 3/2004 | King et al. | |
| 6,733,485 B1 | 5/2004 | Whitehurst et al. | |
| 6,738,663 B2 | 5/2004 | Schroeppel et al. | |
| 6,901,296 B1 * | 5/2005 | Whitehurst et al. ............ 607/50 | |
| 6,952,615 B2 | 10/2005 | Satake | |
| 7,079,890 B2 | 7/2006 | Ahn et al. | |
| 7,412,285 B2 | 8/2008 | Schroeppel et al. | |
| 7,556,624 B2 | 7/2009 | Laufer et al. | |
| 7,720,549 B2 | 5/2010 | Schroeppel et al. | |
| 7,742,811 B2 | 6/2010 | Schroeppel et al. | |
| 7,837,670 B2 | 11/2010 | Barath | |
| 8,014,854 B2 | 9/2011 | Schroeppel et al. | |
| 8,024,048 B2 | 9/2011 | Schroeppel et al. | |
| 9,211,155 B2 | 12/2015 | Fruland et al. | |
| 9,597,145 B2 | 3/2017 | Nelson et al. | |
| 10,004,551 B2 | 6/2018 | Burnett | |
| 10,085,800 B2 | 10/2018 | Nelson et al. | |
| 2001/0001314 A1 * | 5/2001 | Davison et al. ................ 606/41 | |
| 2001/0021868 A1 | 9/2001 | Herbst et al. | |
| 2001/0034518 A1 * | 10/2001 | Edwards et al. ............... 606/41 | |
| 2002/0002329 A1 | 1/2002 | Avitall | |

(56) References Cited

U.S. PATENT DOCUMENTS

| | | |
|---|---|---|
| 2002/0026188 A1 | 2/2002 | Balbierz et al. |
| 2002/0077676 A1 | 6/2002 | Schroeppel et al. |
| 2002/0111618 A1 | 8/2002 | Stewart et al. |
| 2002/0115957 A1 | 8/2002 | Sun et al. |
| 2002/0183735 A1 | 12/2002 | Edwards et al. |
| 2003/0130711 A1 | 7/2003 | Pearson et al. |
| 2003/0191504 A1 | 10/2003 | Meadows et al. |
| 2003/0212394 A1 | 11/2003 | Pearson et al. |
| 2004/0010290 A1 | 1/2004 | Schroeppel et al. |
| 2004/0030334 A1 | 2/2004 | Quick et al. |
| 2004/0059326 A1 | 3/2004 | Flores |
| 2004/0172089 A1 | 9/2004 | Whitehurst et al. |
| 2004/0254618 A1 | 12/2004 | Schroeppel et al. |
| 2005/0004438 A1* | 1/2005 | Ward .............. A61B 5/145 600/345 |
| 2005/0004507 A1 | 1/2005 | Schroeppel et al. |
| 2005/0010203 A1 | 1/2005 | Edwards et al. |
| 2005/0054994 A1 | 3/2005 | Cioanta et al. |
| 2005/0080409 A1 | 4/2005 | Young et al. |
| 2005/0131508 A1 | 6/2005 | Garabedian et al. |
| 2005/0159742 A1 | 7/2005 | Lesh |
| 2005/0182449 A1* | 8/2005 | Auge et al. ............. 607/3 |
| 2005/0197657 A1* | 9/2005 | Goth .............. A61B 18/14 606/41 |
| 2005/0222623 A1 | 10/2005 | Kroll et al. |
| 2005/0222646 A1 | 10/2005 | Kroll et al. |
| 2005/0228373 A1 | 10/2005 | Kelly et al. |
| 2005/0245923 A1* | 11/2005 | Christopherson .. A61B 18/1477 606/41 |
| 2005/0283125 A1 | 12/2005 | Barkhahn et al. |
| 2005/0288730 A1 | 12/2005 | Deem et al. |
| 2006/0025756 A1 | 2/2006 | Francischelli et al. |
| 2006/0095032 A1 | 5/2006 | Jackson et al. |
| 2006/0235286 A1 | 10/2006 | Stone et al. |
| 2006/0259027 A1 | 11/2006 | Kwan et al. |
| 2007/0016067 A1* | 1/2007 | Webster, III ....... A61B 17/3403 600/464 |
| 2007/0073391 A1 | 3/2007 | Bourang et al. |
| 2007/0179491 A1* | 8/2007 | Kratoska ............ A61B 18/1477 606/32 |
| 2007/0191925 A1 | 8/2007 | Dorn |
| 2007/0255207 A1 | 11/2007 | Hangai et al. |
| 2008/0021275 A1 | 1/2008 | Tearney et al. |
| 2008/0021445 A1 | 1/2008 | Elmouelhi et al. |
| 2008/0027379 A1 | 1/2008 | Wilkins |
| 2008/0071262 A1 | 3/2008 | Azure |
| 2008/0132885 A1* | 6/2008 | Rubinsky ............... A61N 1/327 606/34 |
| 2008/0161804 A1 | 7/2008 | Rioux et al. |
| 2008/0243116 A1 | 10/2008 | Anderson |
| 2009/0024075 A1 | 1/2009 | Schroeppel et al. |
| 2010/0049031 A1 | 2/2010 | Fruland et al. |
| 2010/0049188 A1 | 2/2010 | Nelson et al. |
| 2010/0049192 A1 | 2/2010 | Holtz et al. |
| 2010/0168777 A1* | 7/2010 | Stangenes ........ A61B 17/00234 606/185 |
| 2011/0166569 A1 | 7/2011 | Whayne et al. |
| 2011/0208022 A1 | 8/2011 | Brawer et al. |
| 2012/0203307 A1 | 8/2012 | Schroeppel et al. |
| 2014/0005676 A1 | 1/2014 | Shelton, IV et al. |
| 2016/0184039 A1 | 6/2016 | Shelton, IV et al. |
| 2016/0206370 A1 | 7/2016 | Fruland et al. |
| 2017/0231693 A1 | 8/2017 | Nelson et al. |

FOREIGN PATENT DOCUMENTS

| | | |
|---|---|---|
| EP | 2 326 274 | 6/2011 |
| WO | WO 1997/036632 A1 | 10/1997 |
| WO | WO 98/47562 A1 | 10/1998 |
| WO | WO 01/52931 A1 | 7/2001 |
| WO | WO 01/62336 A1 | 8/2001 |
| WO | WO 02/98501 A2 | 12/2002 |
| WO | WO 2005/086683 A2 | 9/2005 |
| WO | WO 06/042117 A2 | 4/2006 |
| WO | WO 2008/083407 A1 | 7/2008 |
| WO | WO 2010/022275 A1 | 2/2010 |
| WO | WO 2010/022278 A1 | 2/2010 |
| WO | WO 2010/081730 A1 | 7/2010 |

OTHER PUBLICATIONS

Nordenstrom B. Preliminary clinical trials of electrophoretic ionization in the treatment of malignant tumors. IRCS Med Sc 1978; 6: 537.

Schauble MK, Mutaz HB, Gallick HD. Inbitition of experimental tumor growth in hamsters by small direct currents. Arch Pathol Lab Med 1977; 101: 294.

Srinivasan S, Gahen Jr. GL, Stoner GE. Electrochemistry in the biomedical sciences. In: Bloom H, Gutmann F (eds): Electrochemistry the last thirty and the next thirty years. New York: Plenum Press, 1977.

Nordenstrom BEW. Biologically closed electric circuits: clinical, experimental and theoretical evidence for an additional circulatory system. Stockholm: Nordic Medical Publications, 1983.

Nordenstrom B. Biologically closed electric circuits: activation of vascular interstitial closed electric circuits for treatment of inoperable cancer. Journal of Bioelectricity 1984; 3(162): 137-153.

Lao, Y., Ge, T., Zheng, X., Zhang, J. Hua, Y., Mao, S., Feng, X. Electrochemical therapy for intermediate and advanced liver cancer: a report of 50 cases. Eur J Surg 1994; Suppl 574: 51-53.

Mir LM, Orlowski S, Belehradek Jr J, Paoletti C. Electrochemotherapy potentiation of antitumour effect of bleomycin by local electric pulses. Eur J Cancer 1991; 27:68-72.

Wolf B, Kraus M, and Sieben U, "Potential of microsensor-based feedback bioactuators for biophysical cancer treatment," Biosensors and Bioelectronics, vol. 12, No. 4, pp. 301-309, 1997.

Kirsch DL, Lerner FN. Electromedicine: the other side of physiology. In: Innovations in pain management: a practical guide for clinicians. Winter Park, FL: GR Press, 1995.

Li K, Xin Y, Gu Y, Xu B, Fan D. Ni B. Effects of direct current on dog liver: possible mechanisms for tumor electrochemical treatment. Bioelectromagnetics 1997; 18: 2-7.

Berendson J. Simonsson D. Electrochemical aspects of treatment of tissue with direct current. Eur J Surg 1994: Suppl 574: 111-115.

Song Y, Li C, Li Y, Song Q. Chang B, Song L. Liu C. Wang T. Electrochemical therapy in the treatment of malignant tumors on the body surface. Eur J Surg 1994; Suppl 574: 41-43.

Matsushima Y, Takahashi E, Hagiwara K, Konaka C, Miura H, Kato H, Koshiishi Y. Clinical and experimental studies of anti-tumoural effects of electrochemical therapy (ECT) alone or in combination with chemotherapy. Eur J Surg 1994; Suppl 574: 59-67.

Xin Y, Xue F, Ge B, Zhao F, Shi B, Zhang W. Electrochemical treatment of lung cancer. Bioelectromagnetics 1997; 18: 8-13.

Nordenstrom BEW. Electrochemical treatment of cancer. I: variable response to anodic and cathodic fields. Am J Clin Oncol (CCT) 1989; 12(6): 530-536.

Nordenstrom BEW. Survey of mechanisms in electrochemical treatment (ECT) of cancer. Eur J Surg 1994: Suppl 574: 93-109.

Chen B, Xie Z, Zhu F. Experimental study on electrochemical treatment of cancer in mice. Eur J Surg 1994: Suppl 574: 75-77.

Chou C, McDougall JA, Ahn C, Vora N. Electrochemical treatment of mouse and rat fibrosarcomas with direct current. Bioelectromagnetics 1997; 18: 14-24.

Nordenstrom BEW, Eksborg, S., Beving, H. Electrochemical treatment of cancer. II: effect of electrophoretic influence on adriamycin. Am J Clin Oncol (CCT)1990; 13(1): 75-88.

Xin, Y. Organisation and spread of electrochemical therapy (ECT) in China. Eur J Surg 1994; Suppl 577: 25-30.

Quan, K. Analysis of the clinical effectiveness of 144 cases of soft tissue and superficial malignant tumors treated with electrochemical therapy. Eur J Surg 1994; Suppl 574: 37-40.

Wang, H. Electrochemical therapy of 74 cases of liver cancer. Eur J Surg 1994; Suppl 574: 55-57.

Song, L., Liu, C., Zhang, B., Wang, T., Song, Y., Li, Y. Electrochemical therapy (ECT) for thyroid adenoma during acupuncture anaesthesia: analysis of 46 patients. Eur J Surg 1994; Suppl 574: 79-81.

(56) References Cited

OTHER PUBLICATIONS

Yokoyama, M., Itaoka, T., Nakajima, H., Ikeda, T., Ishikura, T., Nitta, S. [The use of direct current in the local destruction of cancer tissues]. Gan to Kagaku Ryoho Apr. 1989; 16(4 Pt 2-2): 1412-1417.
Okino, M. and Mohri, H. Effects of high voltage electrical impulse and an anti-cancer drug on growing tumors. Japanese Journal of Cancer Research, vol. 78, pp. 1319-1321, 1987.
Orlowski, S., Belehradek, J.J., Paoletti,C. and Mir, L.M. "Transient electropermeabilization of cells in culture increase of the cytotoxicity of anti-cancer drugs", Biochem, vol. 37, No. 24, pp. 4727-4733, 1988.
Belahradek, J.J., Orlowski, S., Raimiriz, L.H., Pron, G., Poddevin, B. and Mir, L.M., "Electropermeabilization of cells and tissues assessed by the qualitative and quantitative electroloading of bleomycin", Biochem. Biophys. Acta, vol. 1190, pp. 155-163, 1994.
Hofmann, G.A., Dev. S.B., Dimmer, S. and Nanda, G.S., "Electroporation Therapy: A new approach to the treatment of head and neck cancer, IEEE Transactions on Biomedical Engineering", vol. 46, No. 6, pp. 752-759, 1999.
Schecter, DC. "Containment of Tumors Through Electricity." PACE 1979. vol. 2, pp. 100-114.
Sersa, et al. Improvement of Combined modality therapy with cisplatin and radiation using electroporation of tumors. Int J. Radiation Oncology Biol. Phys. vol. 46, No. 4:1037-1041. (2000).
Hofmann, Dev, Nanda, and Rabussay. electroporation therapy of solid tumors. Critical Reviews in therapeutic Drug Carrier Systems 16(6):523-569 (1999).
Samuelsson, Harnek, Ewers, Jonsson. Electrochemical and megavolt treatment of rat tumors. Eur J Surg Suppl 574:69-70. (1994).
Habal and Schauble. An implantable DC power unit for control of experimental tumor growth in hamsters. Medical Instrumentation 7 No. 5: 305-306. (1973).
Semrov and Miklacic. Calculation of the electrical parameters inn electrochemistry of solid tumors in mice. Comp Biol Med 28:439-448. (2000).
Turler, Schaefer, et al. Local treatment of hepatic metastases with low level direct electrical current: experimental results. Scand J Gastroenterol. 3:322-328. (2000).
http://www.genetronics, retrieved Jul. 29, 2003.
Electro-Cancer Treatment, http://www.st-georg.com/ect.html, retrieved Oct. 25, 1999.
M. Belehradek, C. Domenge, B. Luboinski, S. Orlowski, J. Belehradek, Jr., L.M. MIR. Abstract of Electrochemotherapy, A new antitumor treatment. First clinical phase I-II trial. Cancer Dec. 15, 1993; 72(12):3694-700.
K. Brandisky, I. Daskalov. Abstract of Electrical Field and Current Distributions in Electrochemotherapy, Bioelectrochemistry and Bioenergetics Feb. 1999; 48(1):201-8.
M. Cemazar, G. Sersa and D. Miklavcic. Electrochemotherapy with Cisplatin in the Treatment of Tumor Cells Resistant to Cisplatin, Anticancer Research 18: 4463-4466 (1998).
S.L. David, D.R. Absolom, C.R. Smith, J. Gams, and M.A. Herbert. Effect of Low Level Direct Current on In Vivo Tumor Growth in Hamsters, Cancer Research 45, 5625-5631, Nov. 1985.
D. Liu, Y.L. Xin, B. Ge, F. Zhao, H.C. Zhso. Experimental Studies on Electrolytic Dosage of ECT for Dog's Oesophageal Injury and Clinical Effects of ECT for Oesophageal Anastomotic Opening Stenosis and Oesophageal Carcinoma, European Journal of Surgery 1994; Suppl 574: 71-72.
R.A. Gatenby. Abstract of Mathematical Models of Tumour Invasion Mediated by Transformation-Induced Alteration of Microenvironment pH, Symposium 240: The Tumour Microenvironment: Causes and Consequences of Hypoxia and Acidity, p. 2-3, held at the Novartis Foundation, London, 240 Oct. 10-12, 2000.
L.F. Glass, N.A. Fenske, M. Jaroszeski, R. Perrott, D.T. Harvey, D.S. Reintgen, R. Heller. Abstract of Bleomycin-Mediated Electrochemotherapy of Basal Cell Carcinoma, Journal of the American Academy of Dermatology Jan. 1996; 34(1):82-6.
H. Gong, G. Liu. Effect of Electrochemical Therapy on Immune Functions of Normal and Tumour-Bearing Mice, European Journal of Surgery, Suppl 1994; (574): 73-74.
S.A. Grossman, P.S. Staats, Abstract of Current Management of Pain in Patients with Cancer. Oncology (Huntingt) Mar. 1994; 8(3):93-107.
M.B. Habal. Abstract of Effect of Applied DC Currents on Experimental Tumor Growth in Rats, Journal of Biomedical Materials Research, vol. 14, 789-801 (1980).
M.A. Hamza, P.F. White, H.E. Ahmed, E.A. Ghoname. Abstract of Effect of the Frequency of Transcutaneous Electrical Nerve Stimulation on the Postoperative Opioid Analgesic Requirement and Recovery Profile, Anesthesiology Nov. 1999;91(5):1232-8.
C. Hauton, M. Charbonnier, L. Cara and J.P. Salles, A New Type of Liposome for Electrochemical Treatment of Cancer: The Lipogelosomes, European Journal of Surgery 1994; Suppl 574: 117-119.
C.E. Humphrey, E.H. Seal. Biophysical Approach toward Tumor Regression in Mice, Science, vol. 130, 1959.
M. Kraus and B. Wolf. Implications of Acidic Tumor Microenvironment for Neoplastic Growth and Cancer Treatment: A Computer Analysis, Tumor Biology 1996; 17: 133-154.
M. Kraus and B. Wolf Physicochemical Microenvironment as Key Regulator for Tumor Microevolution, Invasion, and Immune Response: Targets for Endocytotechnological Approaches in Cancer Treatment, Endocytobiosis & Cell Research, 12, 133-156 (1998).
Miklavcic, D. An, J. Belehradek, Jr., L.M. Mir. Abstract of Host's Immune Response in Electrotherapy of Murine Tumors by Direct Current, European Cytokine Network Sep. 1997;8(3):275-9.
D.M. Morris, M.D., A.A. Marino, Ph. D., and E. Gonzalez, M.D. Electrochemical Modification of Tumor Growth in Mice, Journal of Surgical Research 53, 306-309 (1992).
E. Nilsson. Modelling of the Electrochemical Treatment of Tumours. Dissertation, Department of Chemical Engineering and Technology, Applied Electrochemistry, Royal Institute of Technology, Stockholm 2000.
T. Nishi, S.B. Dev., K. Yoshizato, J. Kuratsu, Y. Ushio. Abstract of Treatment of Cancer Using Pulsed Electric Field in Combination With Chemotherapeutic Agents or Genes, Human Cell Mar. 1997;10(1):81-6.
G.D. O'Clock, Ph. D. (E.E.), P.E. The Effects of In Vitro Electrical Stimulation on Eukaryotic Cells: Suppression of Malignant Cell Proliferation, Journal of Orthomolecular Medicine, vol. 12, No. 3, 1997.
W.R. Panje, M.P. Hier, G.R. Garman, E. Harrell, A. Goldman, I. Bloch. Abstract of Electroporation Therapy of Head and Neck Cancer, Annals of Otology, Rhinology and Laryngology Sep. 1998; 107(9 Pt 1): 779-85.
A. Plesnicar, G. Sersa, L. Vodovnik, J. Jancar, L. Zaletel-Kragelj and S. Plesnicar. Electric Treatment of Human Melanoma Skin Lesions with Low Level Direct Electric Current: An Assessment of Clinical Experience Following a Preliminary Study in Five Patients, European Journal of Surgery 1994; Suppl 574:45-49.
N. Raghunand. Abstract of pH and Chemotherapy, Symposium 240: The Tumour Microenvironment: Causes and Consequences of Hypoxia and Acidity, p. 5-6, held at the Novartis Foundation, London, 240 Oct. 10-12, 2000.
L.H. Ramirez, S. Orlowski, D. An, G. Bindoula, R. Dzodic, P. Ardouin, C. Bognel, J. Belehradek Jr., J-N Munck, and L.M. Mir. Electrochemotherapy on Liver Tumours in Rabbits, British Journal of Cancer (1998) 77(12). 2104-2111.
M.K. Schauble, M.B. Habal. Electropotentials of Tumor Tissues. Journal of Surgical Research 9: 9, 1969.
S. Seguchi, S. Kawauchi, Y. Morimoto, T. Arai, H. Asanuma, M. Hayakawa, M. Kikuchi. Abstract of Critical Parameters in the Cytotoxicity of Photodynamic Therapy Using a Pulsed Laser. Lasers Med Sci 2002, 17(4):265-71.
G. Sersa, M. Cemazar, D. Miklavcic and D. J. Chaplin, Tumor Blood Flow Modifying Effect of Electrochemotherapy with Bleomycin, Anticancer Research 19: 4017-4022 (1999).
B.N. Singh and C. Dwivedi. Antitumor Drug Delivery by Tissue Electroporation, Anti-Cancer Drugs 1999, 10, pp. 139-146.
T.V. Taylor, P. Engler, B.R. Pullan and S. Holt. Ablation of Neoplasia by Direct Current, British Journal of Cancer (1994), 70, 342-345.

(56) References Cited

OTHER PUBLICATIONS

A.L. Vandenbogaerde, E.M. Delaey, A.M. Vantieghem, B.E. Himpens, W.J. Merlevede, P.A. de Witte, Abstract of Cytotoxicity and Antiproliferative Effect of Hypericin and Derivatives After Photosensitization. Photochem Photobiol Jan. 1998;67(1):119-25.
P. Vaupel, D.K. Kelleher, M. Hockel. Abstract of Oxygen Status of Malignant tumors: Pathogenesis of Hypoxia and Significance for Tumor Therapy. Semin Oncol Apr. 2001; 28(2 Suppl 8):29-35.
L. Vodovnik, D. Miklavcic, G. Sersa. Modified Cell Proliferation Due to Electrical Currents, Medical and Biological Engineering and Computing, 1992, 30, CE21-CE28.
H. von Euler, Electrochemical Treatment of Tumours, Doctoral Thesis, Swedish University of Agricultural Sciences, Uppsala 2002.
J.C. Weaver. Electroporation: A General Phenomenom for Manipulating Cells and Tissues. J Cell Biochem 1993; 51 No. 4: 426-435.
Wojcicki, R. Kostyrka, B. Kaczmarek, J. Kordowski, M. Romanowski, M. Kaminski, J. Klonek, S. Zielinski. Abstract of Electrochemical Therapy in Palliative Treatment of Malignant Dysphagia: A Pilot Study, Hepatogastroenterology Jan.-Feb. 1999;46(25):278-84.
B. Wolf, M. Brischwein, W. Baumann, R. Ehret, T. Henning, M. Lehmann, A. Schwinde. Microsensor-Aided Measurements of Cellular Signalling and Metabolism on Tumor Cells, Tumor Biology 1998; 19:374-383.
Y.L. Xin, F.Z. Xue, F.G. Zhao. Effectiveness of Electrochemical Therapy in the Treatment of Lung Cancers of Middle and Late Stage, Chinese Medical Journal 1997 110(5): 379-383.
Y. Yen, J.R. Li, B.S. Zhou, F. Rojas, J. Yu and C.K. Chou. Electrochemical Treatment of Human KB Cells in Vitro, Bioelectromagnetics 20:34-41 (1999).
Y.L. Xin, D. Liu. Electrostatic Therapy (EST) of Lung Cancer and Pulmonary Metastasis: Report of 15 Cases. European Journal of Surgery 1994; Suppl 574: 91-92.
X.Z. Lin, C.M. Jen, C.K. Choud, D.S. Chou, M.J. Sung, T.C. Chou. Saturated Saline Enhances the Effect of Electrochemical Therapy. Digestive Diseases and Sciences 2000: 45(3): 509-514.
Damascelli B, Patelli G, Frigerio LF, Lanocita R, Di Tolla GD, Marchiano A., Spreafico C, Garbagnati F, Bonalumi MG, Monfardini L Ticha V, Prino A. First clinical experience with a high-capacity implantable infusion pump for continuous intravenous chemotherapy. Cardiovasc Intervent Radiol 1999; 22: 37-43.
Ranade VV. Drug delivery systems. 4. Implants in drug delivery. J Clin Pharmacol 1990; 30 No. 10: 871-889.
Buchwald H, Rohde TD. Implantable pumps. Recent progress and anticipated future advances. ASAIO J 1992; 38 No. 4: 772-778.
Wigness BD, Dorman FD, Robinson Jr HJ, Arendt EA, Oegema Jr TR,Rohde TD, Buchwald H. Catheter with an anchoring tip for chronic joint capsule perfusion. ASAIO Trans. 1991; 37 No. 3: M290-292.
Heruth KT, Medtronic SynchroMed drug administration system. Ann NY Acad Sci 1988; 531: 72-75.
Vogelzang NJ, Ruane M, DeMeester TR. Phase I trial of an implanted battery-powered, programmable drug delivery system for continuous doxorubicin administration. J Clin Oncol 1985; 3 No. 3: 407-414.
Application and File history for U.S. Appl. No. 09/524,405, filed Mar. 13, 2000, now U.S. Pat. No. 6,366,808, issued Apr. 2, 2002. Inventors: Schroeppel et al.
Application and File history for U.S. Appl. No. 09/974,474, filed Dec. 14, 2001, now U.S. Pat. No. 6,738,663, issued May 18, 2004. Inventors: Schroeppel et al.
Application and File history for U.S. Appl. No. 10/434,400, filed May 7, 2003, now U.S. Pat. No. 7,412,285, issued Aug. 12, 2008. Inventors: Schroeppel et al.
Application and File history for U.S. Appl. No. 10/792,256, filed Mar. 2, 2004, now U.S. Pat. No. 7,742,811, issued Jun. 22, 2010. Inventors: Schroeppel et al.
Application and File history for U.S. Appl. No. 12/173,639, filed Jul. 15, 2008, now U.S. Pat. No. 8,014,854, issued Sep. 6, 2011. Inventors: Schroeppel et al.
Application and File history for U.S. Appl. No. 13/226,319, filed Sep. 6, 2011. Inventors: Schroeppel et al.
Application and File history for U.S. Appl. No. 10/819,641, filed Sep. 6, 2011, now U.S. Pat. No. 7,720,549, issued May 18, 2010. Inventors: Schroeppel et al.
Application and File history for U.S. Appl. No. 10/881,375, filed Jun. 29, 2006. Inventors: Schroeppel et al.
Application and File history for U.S. Appl. No. 10/841,205, filed May 7, 2004, now U.S. Pat. No. 8,024,048, issued Sep. 20, 2011. Inventors: Schroeppel et al.
Application and File history for U.S. Appl. No. 12/544,112, filed Aug. 19, 2009. Inventors: Fruland et al.
Application and File history for U.S. Appl. No. 12/544,127, filed Aug. 19, 2009. Inventors: Holtz et al.
Application and File history for U.S. Appl. No. 12/544,134, filed Aug. 19, 2009. Inventors: Nelson et al.
EP Application No. 037997616, EP Search Report, dated Feb. 2, 2010.
EP Application No. 05733003.7, Search Report, dated Apr. 11, 2008.
EP 05733003.7, Office Action, dated Aug. 13, 2008.
EP Application No. 05733003.7, Examination Report, dated Apr. 21, 2009.
PCT/US2003/14104, International Search Report, Nov. 18, 2004.
PCT/US2005/011430, PCT International Written Opinion, dated Jan. 13, 2006.
PCT/US2009/54528, PCT International Search Report, dated Oct. 22, 2009.
PCT/US2009/054523, PCT International Preliminary Report on Patentability and Written Opinion, dated Feb. 22, 2011.
EP09808837.0, EP Search Opinion, dated Apr. 11, 2012.
EP09808839.6, EP Search Opinion, dated Jul. 27, 2012.
EP09808839.6, EP Summons to Attend Oral Proceedings, dated Sep. 13, 2018, 7 pages.
PCT/US2018/062618, PCT International Search Report and Written Opinion dated Feb. 29, 2019, 7 pages.
Application and File history for U.S. Appl. No. 14/969,889, filed Dec. 15, 2015. Inventors: Fruland et al.
Application and File history for U.S. Appl. No. 15/455,358, filed Mar. 10, 2016. Inventors: Nelson et al.
Application and File history for U.S. Appl. No. 16/148,756, filed Oct. 1, 2018. Inventors: Nelson et al.
Application and File history for U.S. Appl. No. 16/287,551, filed Feb. 27, 2019. Inventors: Kroll et al.
Application and File history for U.S. Appl. No. 16/201,642, filed Nov. 27, 2018. Inventors: Gilmour et al.
Dalziel et al., "Let-Go Currents and Voltages," Transactions of the American Institute of Electrical Engineers, Part II: Applications and Industry, 75(2): pp. 49-56, 1956.

\* cited by examiner

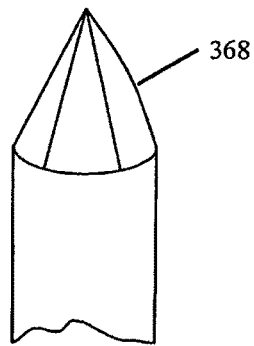
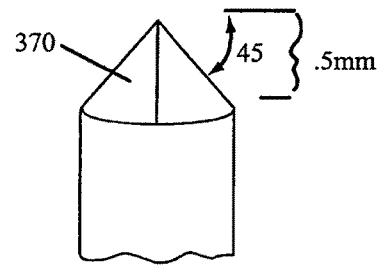
FIG. 35A    FIG. 35B
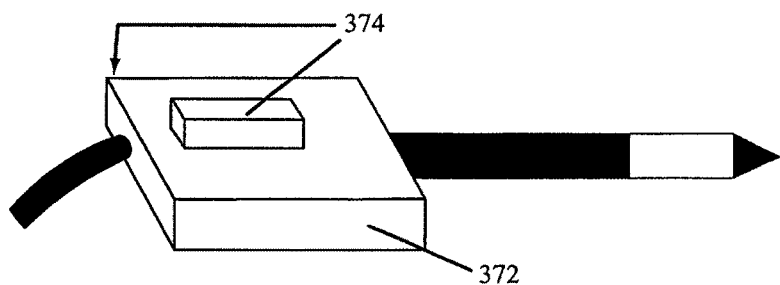
FIG. 36

LOW-CORROSION ELECTRODE FOR TREATING TISSUE

CROSS-REFERENCE TO RELATED APPLICATIONS

This application claims priority to U.S. Provisional Patent Application Nos. 61/090,594, filed Aug. 20, 2008; 61/090,519, filed Aug. 20, 2008; 61/090,600, filed Aug. 20, 2008; and 61/090,589, filed Aug. 20, 2008; and is related to the following U.S. Patent Applications:

U.S. patent application Ser. No. 12/544,112 entitled "Non-Thermal Ablation System for Treating BPH and Other Growths", filed on Aug. 18, 2009;

U.S. patent application Ser. No. 12/544,127 entitled "Catheter for Treating Tissue with Non-thermal Ablation", filed on Aug. 18, 2009;

U.S. patent application Ser. No. 12/544,134 entitled "Non-Thermal Ablation System for Treating Tissue", filed on Aug. 18, 2009.

The contents of each of the above listed applications are hereby incorporated by reference herein in their entireties.

FIELD OF THE INVENTION

The present invention relates generally to systems and methods for treating tissue and, more specifically, to low-corrosion electrodes for non-thermal ablation systems and methods for treating tissue.

BACKGROUND

Enlargement of the prostate gland (known as benign prostatic hyperplasia or hypertrophy—"BPH") is a common ailment in older men. BPH affects 40% of men in their 50s and 90% of men in their 80s. The enlargement of the prostate is a form of benign tumor or adenoma. FIG. 1 illustrates a simplified view of the anatomy and location of the prostate 3, 4. The urethra 1 passes upwards through the external urethral sphincter 2, through the prostate 3, 4 (surrounding the urethra), and into the bladder 5. The prostate 3, 4 comprises three lobes: two major lobes 3, 4 and a median lobe. The median lobe is located generally behind the major lobes 3, 4.

As the prostate becomes enlarged, it may compress the urethra and cause one or more of the following symptoms to occur: more frequent urination, weak urine stream, inability to delay urination, difficulty starting and stopping urination, incomplete emptying of the bladder, loss of bladder control, and painful or bloody urination.

If symptoms are mild and do not affect quality of life, treatment may not be performed. If diagnosed with BPH but not pursuing treatment options, men typically receive regular checkups and report increased BPH symptoms to the physician. If symptoms occur and cause discomfort, affect activities of daily living, or endanger health, drug treatment or surgery may be recommended. Treatment options for BPH include lifestyle changes (such as adjusting fluid intake), herbal remedies, drug therapy, non-surgical procedures, and surgical procedures. The goals of treatment are generally to improve urinary flow and decrease symptoms associated with BPH. Treatment may delay or prevent the progression of BPH.

Drugs may be used to relieve the common urinary symptoms associated with BPH by either reducing the size of the prostate gland or by slowing the growth of the prostate. Common drug classes used to treat urinary symptoms include alpha blockers, such as doxazosin or tamsulosin, and 5-alpha reductase inhibitors, such as finasteride or dutasteride. The medications may have deleterious side effects such as decreased libido, impotence, retrograde ejaculation, fatigue, dizziness, headache, and decreased blood pressure. If drug therapy does not provide adequate relief of symptoms, surgery may be needed to help correct the prostate gland overgrowth. Further, if more severe symptoms of BPH present, such as recurrent urinary retention, recurrent blood in the urine, recurrent urinary tract infections or bladder stones, drug therapy should not be initiated. Generally, upon presentation of these symptoms, surgery is indicated.

Surgical treatments of BPH may or may not be minimally invasive. For the surgical methods, access to the prostate may be via the urethra, the perineum, or other route.

Non-minimally invasive surgical treatments include Trans Urethral Resection of the Prostate (TURP). Conducted in an operating room under general or spinal anesthetic, a probe is passed through the urethra which scrapes away prostate tissue causing the blockage. Side effects may include retrograde ejaculation, impotence, and a repeat of the procedure if the blockage regrows. U.S. Pat. No. 6,491,672, herein incorporated by reference, discloses one surgery option for treating BPH.

Minimally invasive surgical treatments usually offer the incentives of less pain, faster recovery, lower costs, and use of local anesthesia and a mild sedative. In general, minimally invasive surgical treatments destroy prostate tissue through one of various mechanisms. The destroyed prostate tissue may be reabsorbed by the body and/or discharged into the urine over a period of time. Minimally-invasive surgical treatment options include generation of heat, freezing, chemical means, and ultrasound to destroy prostate tissue. Care must be taken to avoid damaging sensitive areas adjacent the prostate such as nerves controlling sexual functions or the rectal wall.

Various types of laser treatment of BPH exist including laser prostatectomy, interstitial laser coagulation, photosensitive vaporization of the prostate, Holmium laser ablation of the prostate, and Holmium laser enucleation of the prostate (HoLEP). Laser prostatectomy uses a transurethral laser device to cut or vaporize obstructions. Interstitial Laser Coagulation uses a cystoscope through which a fiberoptic probe is directly introduced into the prostate. A small laser fiber is inserted into the prostate through the device inserted in the urethra. Laser energy heats a selected area and the probe may be moved several times to treat all areas of obstruction. Photosensitive vaporization of the prostate (PVP) uses a laser delivered through an endoscope inserted into the urethra. The high-energy laser vaporizes excess prostate tissue and seals the treated area.

For microwave treatment of BPH, a microwave antenna is inserted transurethrally into the prostate. Various forms of microwave treatment may include a cooling means for minimizing patient discomfort and to protect adjacent urethral tissue from damage. Further means may be used to dilate the urethra.

Heat for treatment of BPH may be generated, for example, via laser beams, microwaves, radiofrequency current, or direct current. Other heat application techniques exist for treating BPH including transurethral vaporization of the prostate (TUVP) wherein heat is applied directly to the prostate with a grooved roller bar that vaporizes tissue and water-induced thermotherapy (WIT) to destroy obstructive tissue wherein hot water flows through a transurethrally-placed balloon. U.S. Pat. Nos. 5,928,225 and 6,640,139, herein incorporated by reference in their entirety, further disclose treatment methods using heat.

Non-thermal treatments of BPH include injection of ethanol (see, for example, U.S. Pat. No. 7,015,253) or direct current ablation (see, for example, U.S. Pat. Nos. 7,079,890; 6,733,485; and 6,901,294).

Transurethral ethanol ablation of the prostate (TEAP) may be used to treat BPH and typically uses a cystoscope with a curved needle to inject ethanol in various doses.

High intensity focused ultrasound (HIFU) may be used to treat BPH and noninvasively focuses ultrasound waves to heat and destroy targeted prostate tissue.

Various radiofrequency current treatment methods of BPH have been developed. Some methods are shown and described in U.S. Pat. Nos. 6,106,521; 6,638,275; and 6,016,452, all herein incorporated by reference in their entireties. In one treatment method, transurethral needle ablation, a small needle is inserted into the prostate from the urethra. Radio frequency (RF) energy is applied to the needle to generate heat in specific areas of the prostate. RF frequency based ablation of tissue is done via thermal treatment. Typically, treatment is done until a certain temperature is reached and is then discontinued. An assumption is made that sufficient ablation has occurred on the basis of the reached temperature.

As may be appreciated, many of these BPH treatment methods include transurethral access. Transurethral access may involve catheter-based electrodes within the prostatic urethra (see, for example, U.S. Pat. Nos. 6,517,534 and 5,529,574) or electrodes designed to puncture the urethra and dwell inside the prostate (see, for example, U.S. Pat. Nos. 6,638,275; 6,016,452; 5,800,378; and 5,536,240), transurethral access including balloons for positioning and stabilizing the electrodes (see, for example, U.S. Pat. Nos. 6,517,534 and 7,066,905), transurethral access including means for puncturing the urethral wall (see, for example, U.S. Pat. No. 5,385,544), and transurethral access including means for more accurately placing the electrodes (see, for example, U.S. Pat. No. 6,638,275).

Accordingly, a need exists in the art for a minimally invasive low power, non-thermal method of treating tissue via direct current ablation.

BRIEF SUMMARY

Systems and methods for treating tissue, and particularly systems and methods for non-thermal ablation of tissue, are provided. In various embodiments, the systems and methods use a non-implantable system employing direct current ablation for targeting the area to be treated. DC current ablates tissue by imparting extreme pH into the tissue surrounding electrode. In general, the systems and methods may be used to treat any form of tissue where ablation is desired including, for example, adipose tissue, muscular tissue, glandular tissue, nodular tissue, and fibrous tissue. In specific embodiments, the systems and methods may be used to treat benign prostatic hypertrophy or hyperplasia (BPH). In other embodiments, the systems and methods may be used to treat cancerous tissue. One skilled in the art will appreciate that specifics of the systems and methods may be modified for access to various sites in the body for treating different tissues.

In one embodiment, a low-corrosion electrode for use with a system for non-thermal direct current ablation of tissue is provided. The electrode includes a catheter end configured for coupling to a catheter, a tip configured for puncturing the tissue, and a length extending between the catheter end and the tip. The length includes an electrically conductive active portion and an insulated portion. The active portion is between approximately 3 mm and 12 mm long at an inserted portion of the electrode and has an outer diameter of 0.25 to 1.0 mm. The length further includes a supporting inner core and an outer shell formed of a material having a high resistance to corrosion.

In a further embodiment, a minimally invasive system for treatment of tissue in a body via direct current ablation is provided The system includes a catheter for insertion into the body, wherein a portion of the catheter remains outside of the body when the catheter is in a treatment position. The system further includes a plurality of electrodes positioned for deployment through and outwardly from the catheter. Each electrode comprises an inner core having a high resistance to bending stress and an outer shell having a high resistance to corrosion, wherein the outer shell and inner core together comprise a drawn filled tube. The electrodes impart at least one of a high pH and a low pH such that a necrotic zone is created around each electrode to form a field of treatment. The system further includes a power source for applying power to the plurality of electrodes, wherein the power source is configured to apply between 10 to 100 mA of direct current. Treatment using the system is substantially non-thermal.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

BRIEF DESCRIPTION OF THE DRAWINGS

FIG. 10b illustrates an end view of the catheter of the system of FIG. 10a.

FIG. 22b illustrates an electrical diagram of the embodiment of FIG. 22a.

FIG. 35a illustrates features for preventing moving electrodes from sticking to the inside of a curved channel, in accordance with one embodiment.

FIG. 35b illustrates features for preventing moving electrodes from sticking to the inside of a curved channel, in accordance with another embodiment.

FIG. 36 illustrates a straight wire electrode with a crimp tube that contains an orientation feature, in accordance with one embodiment.

DETAILED DESCRIPTION

Systems and methods for treating tissue, and particularly systems and methods for non-thermal ablation of tissue, are provided. In various embodiments, the systems and methods use a non-implantable system employing direct current ablation for targeting the area to be treated. DC current ablates tissue by imparting extreme pH into the tissue surrounding electrode. DC current ablation uses low power to treat tissues and creates necrosis without a significant increase in tissue temperatures. In general, the systems and methods may be used to treat any form of tissue where ablation is desired including, for example, adipose tissue, muscular tissue, glandular tissue, nodular tissue, and fibrous tissue. In specific embodiments, the systems and methods may be used to treat benign prostatic hypertrophy or hyperplasia (BPH). In other embodiments, the systems and methods may be used to treat cancerous tissue and benign tumors. One skilled in the art will appreciate that specifics of the systems and methods may be modified for access to various sites in the body for treating different tissues.

Ablation of pathologic tissue can be performed using low level DC current. This may be done by powering multiple electrodes and imparting a high pH at one polarity electrode and a low pH at the opposite polarity electrode. Generally, DC ablation resists diffusing across tissue boundaries and thus can be used to treat tissue with minimal concern to affecting adjacent tissues. Further, in systems employing a plurality of electrodes, treatment may be done with relatively slow application of DC current with the total treatment time reduced by the plurality of electrodes.

System Overview

Figure 1:
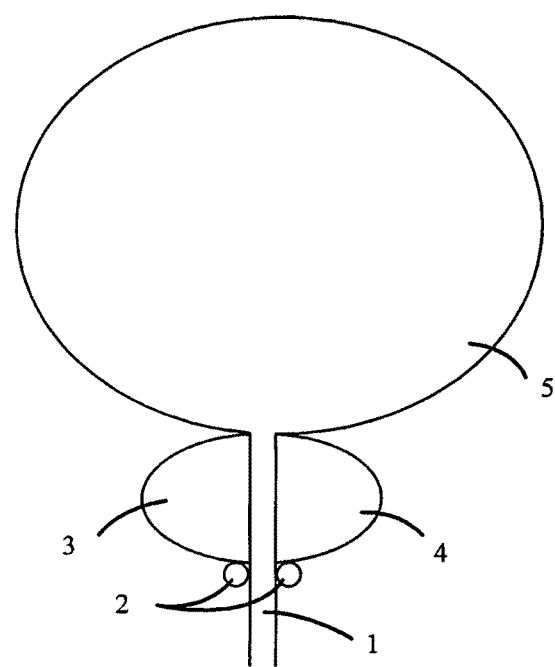
FIG. 1 illustrates a block anatomy diagram of the prostate area.
Figure 2A:
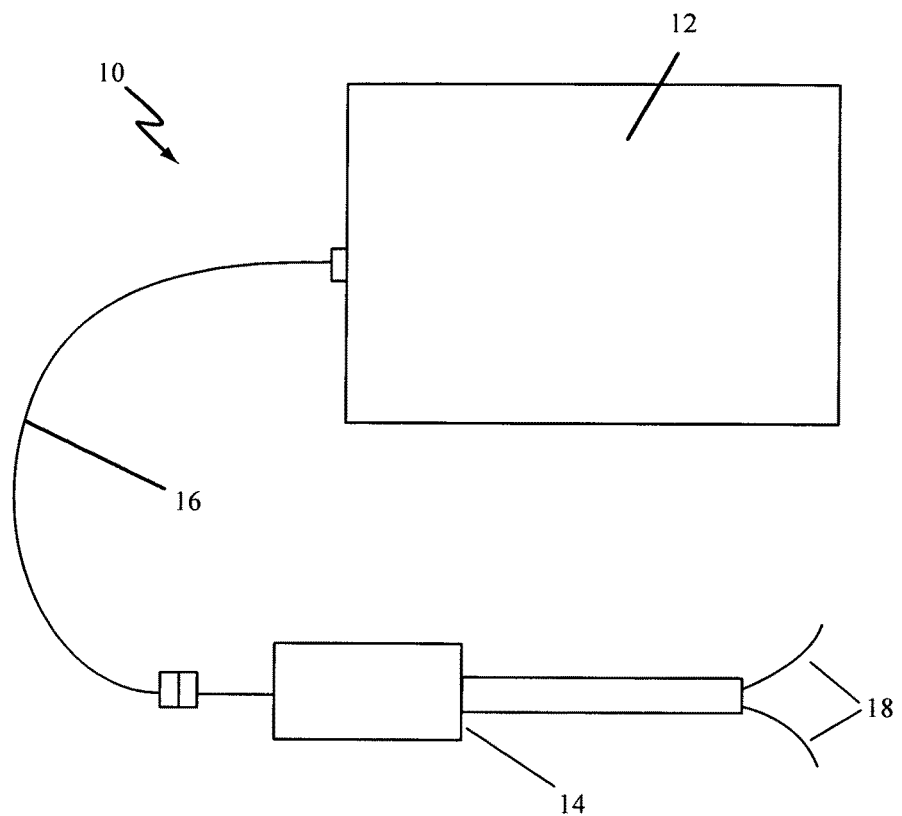
FIG. 2a illustrates a system for treating tissue, in accordance with one embodiment.

FIG. 2a illustrates a basic system configuration. As shown, the system 10 includes a generator 12, a catheter 14, electrodes 18, and a cable 16 running from the generator 12 to the catheter 14. The catheter 14 may be inserted in the body to a desired location for tissue treatment. Once positioned, the electrodes 18 may be deployed, for example through the catheter 14. To treat tissue, power is provided by the generator 12 to the electrodes 18. The electrodes then apply a DC current to a treatment area of the tissue. The tissue is thus treated by DC ablation in a non-thermal manner.

Figure 2B:
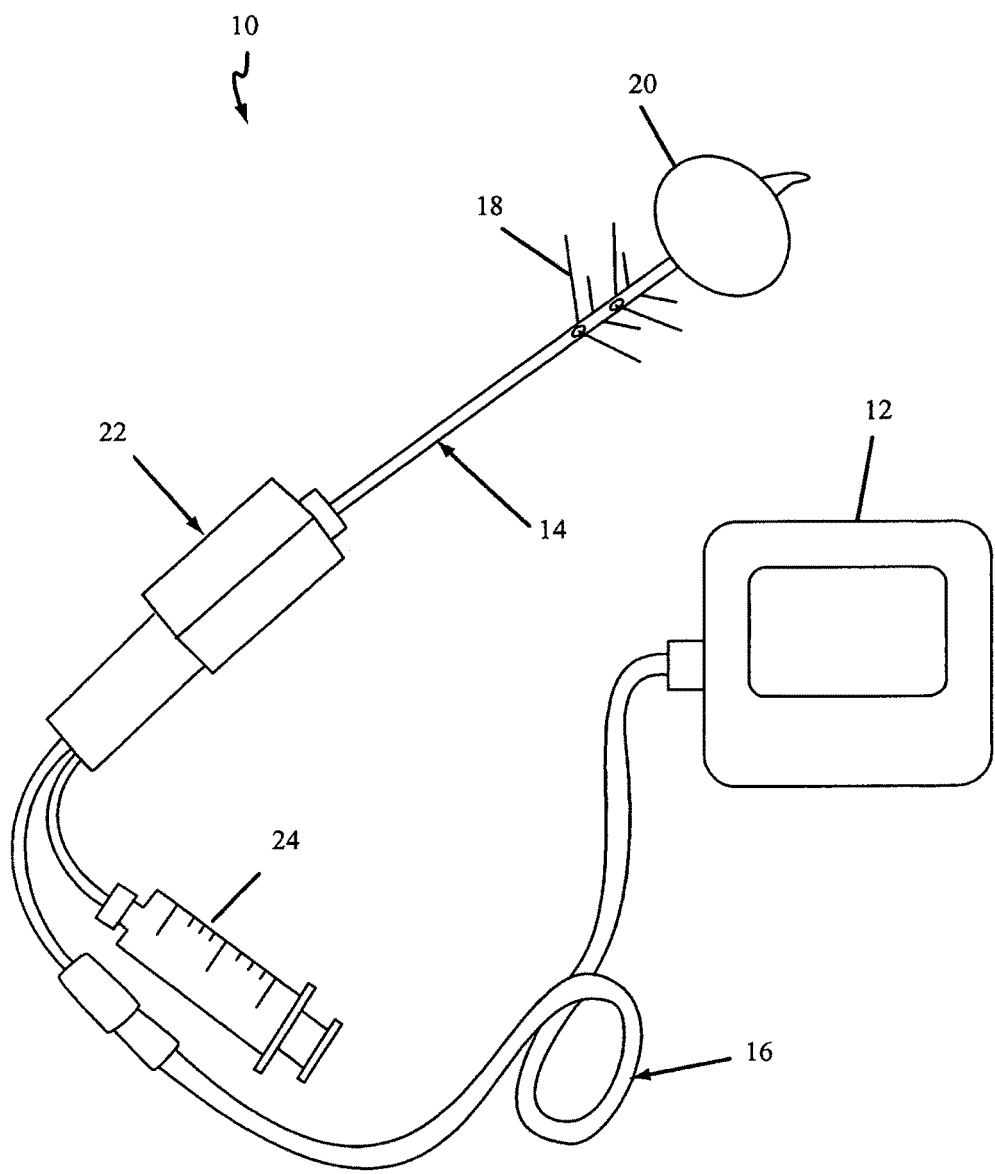
FIG. 2b illustrates a system for treating BPH, in accordance with one embodiment.

FIG. 2b illustrates an embodiment of the system of FIG. 2a configured for treatment of prostate tissue (or BPH treatment). As shown, the system 10 includes a generator 12, a catheter 14, an electrical connection 16 from the generator to the catheter, a plurality of electrodes 18, a mechanism 22 for deploying the electrodes, a stabilization mechanism or fixation element 20, and a mechanism 24 for deploying the stabilization mechanism. In various embodiments, the catheter 14 may be a transurethral catheter. In some embodiments, the electrodes 18 may be provided as pairs of electrodes. In some embodiments, an electronic control system may be included. The system and method may be used for treatment of BPH via deployment of the one or more electrodes through the transurethral catheter and application of direct electrical current to the one or more electrodes. In alternative embodiments, the system may comprise a catheter for other laparoscopic or percutaneous access to a treatment site. The electrodes produce a field of treatment that covers a predictable area of the target tissue. When deployed transurethrally, the electrodes can produce a field of treatment covering a predictable area of prostatic tissue. A necrotic zone may be created around each of the electrodes and the created necrotic zones coalesce to form the field of treatment. The field of treatment begins at the electrode and diffuses out generally passively.

The electrodes may be provided in any number, may have various shapes, may have various deployment configurations, and may be manufactured of various materials, as shown and discussed in copending U.S. patent application Ser. No. 12/544,119, herein incorporated by reference in its entirety. In some embodiments, the electrodes are provided in pairs. The Ability to control the mechanical length, angle, and electrical polarity of each electrode, as well as the amount of current passing through each electrode allows debulking of a predictable region in a controlled manner while reducing risk of damage to adjacent, non-targeted areas. Generally, application of DC ablation to treat tissue will not result in scar tissue such as arises from other forms of treatment.

In the embodiment shown in FIG. 2b, the electrodes 18 are provided as four electrode pairs, each electrode being generally cylindrical. As shown, two of the electrode pairs comprise shorter electrodes and two of the electrode pairs comprise longer electrodes. Each electrode pair comprises an anode and a cathode. An anode is defined as the electrode with higher voltage potential. A cathode is defined as the electrode with the lower voltage potential. In the embodiment of FIG. 2b, the electrodes deploy outward from the catheter. Such outward deployment may be, for example, radial or may be linear. Generally, the electrodes may be coupled to the catheter or to a support structure in the catheter. As can be appreciated, the electrodes and their coupling with the catheter or a support structure provided within the catheter may be configured to extend from the catheter at different angles, for different lengths, etc. Angles of extension may further be influenced by the shape and configuration of the routing holes. The various system configurations may be designed based on the tissue to be treated and a selected access route to the tissue to be treated. In some embodiments, for example, the system may be configured for treatment of prostate tissue, or more specifically, for treatment of a large region of prostate tissue.

The electrodes 18 are configured for puncture and proper placement of the electrode tip to create a desired treatment area. The electrodes 18 further are configured to resist corrosion. In some embodiments, the electrodes 18 may comprise a Nitinol wire with a corrosion resistant coating. The corrosion resistant coating may be, for example, platinum. In some embodiments, the electrodes may be configured to be atraumatic. In an embodiment comprising needle electrodes, for example, the tip of the needle electrode may be self-introducing. Using a transurethral approach, deployment of the electrodes comprises extension from the transurethral catheter and through the urethra. Accordingly, the electrodes pierce the urethra. Thus, in embodiments for treating BPH, the electrode tip may be sufficiently sharp to penetrate the urethra.

In use, current is supplied to the electrodes to create a reaction around the electrodes to change the structure of the tissue in a treatment zone around the electrodes. The system thus may further include a generator for supplying current to the electrodes. The non-thermal ablation system generally is a lower power system, using, for example, on the order of milliwatts. The system thus does not create significant heat during treatment, thus mitigating side effects often associated with thermal treatment. The size and shape of the treatment zone varies depending on, at least, treatment time, current delivered, electrode size and shape, and positioning of the electrode relative to tissue boundaries. As a general matter, by using a plurality of electrodes that are properly placed, treatment may be done at a relatively slow rate but the total treatment time may be relatively fast. The shape of the treatment zone around a cylindrical electrode, such as shown in FIG. 2b, is approximately an ellipsoid or cylinder with hemispheric ends with the distance from the boundary of the treatment zone and the surface of the electrode having a generally consistent radius, referred to herein as the radius of treatment.

Figure 3A:
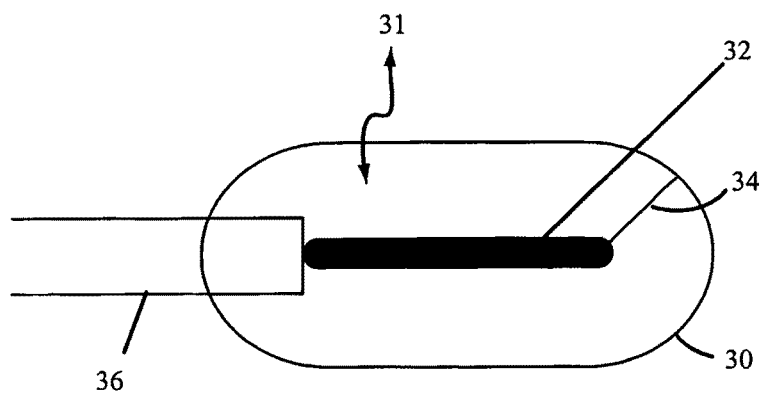
FIG. 3a illustrates a side view of an electrode, radius of treatment, and treatment zone, in accordance with one embodiment.
Figure 3B:
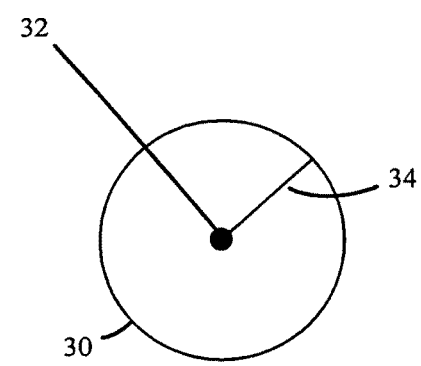
FIG. 3b illustrates an end view of an electrode, radius of treatment, and treatment zone, in accordance with one embodiment.

FIG. 3a illustrates a side view and FIG. 3b illustrates an end view of an active electrode. As shown, the electrode 31 includes an active portion 32 and an insulated portion 36. The insulated portion 36 of the electrode is resistant to the corrosive environment created during ablation. FIGS. 3a and 3b further illustrate the radius of treatment 34, treatment zone 30 associated with the active portion 32 of the electrode 31.

Figure 4A:
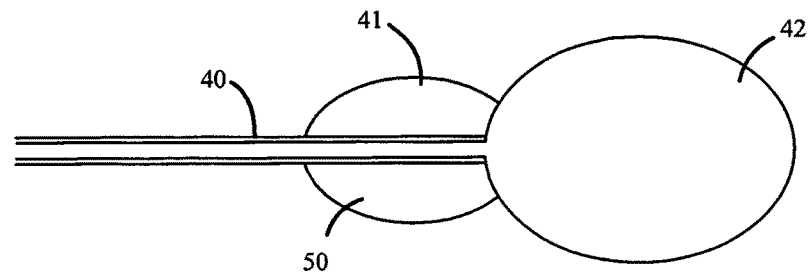
FIG. 4a illustrates anatomy of a prostate region prior to deployment of a device for treating tissue.
Figure 4B:
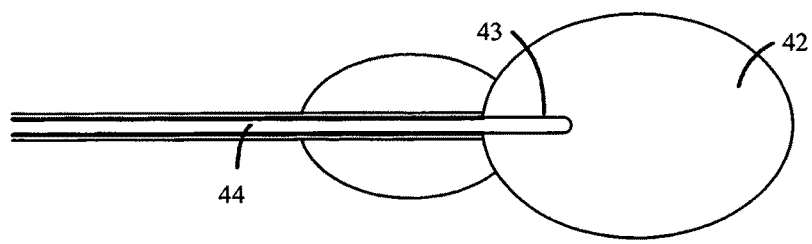
FIG. 4b illustrates transurethral insertion of a catheter for deployment of a device for treating tissue, in accordance with one embodiment.
Figure 4C:
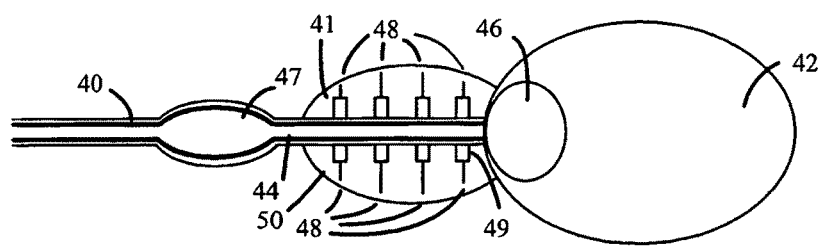
FIG. 4c illustrates deployment of electrodes, in accordance with one embodiment.

FIGS. 4a-4c illustrate deployment of a device for treating tissue in a prostate region, in accordance with one embodiment. Specifically, FIGS. 4a-4c illustrate the device relative the urethra 40, prostate gland 41, prostate capsule or wall 50, and bladder 42. Before treatment, the tissue to be treated may be assessed to determine appropriate treatment protocol. FIG. 4a illustrates a simplified diagram of the anatomy of a prostate region prior to deployment of a device for treating tissue. FIG. 4b illustrates transurethral insertion of the catheter 44 and shows the distal end 43 of the catheter 44. FIG. 4c illustrates deployment of the electrodes 48 and their insulation sleeves 49 through the catheter 44; with the catheter 44 generally fixed in place by one or more balloons 46, 47 (or other fixation element).

FIG. 4b illustrates an embodiment for BPH treatment wherein a catheter 44 is inserted transurethrally. In various embodiments, the catheter 44 may be flexible or semi-flexible or semi-rigid distally from the entrance of the urethra, as deployed. In one embodiment the catheter body has a flex modulus of between about 0.4 and 3 GPa. The catheter may be advanced with the guidance of a trans-rectal ultrasound (TRUS). In FIG. 4b, the distal end 43 of the catheter 44 is shown inserted in the bladder 42. The catheter 44 may include one or more balloons 46 and 47, as shown in FIG. 4c. To fix the system in place, one balloon 46 is expanded within the bladder and one balloon 47 is expanded in the urethra 40. Other anchoring mechanisms or fixation elements may alternatively be used. In some embodiments, the balloon 46 expanded within the bladder 42 assists in placement of the catheter 44. For example, the balloon 46 may be inflated after the catheter tip has entered the bladder and the catheter may be retracted until resistance is felt by the balloon 46. The balloons further may assist in maintaining the catheter in a treatment position. Various methods of imaging, such as ultrasound using a rectal probe, may be used to help position the catheter.

FIG. 4c illustrates electrode deployment after anchoring of the catheter. In the embodiment of FIG. 4c, the catheter 44 includes eight needle electrodes 48 at four different positions on the catheter 44. The electrodes 48 and their electrical insulation sleeves 49 pierce the urethra 40 and enter the prostate 41. As shown, the length of the electrodes 48 may be varied to optimize the field of treatment for the given size and shape of the prostate 41. In the deployment position, none of the electrodes 48 pierce the prostate wall 50. After the electrodes have been positioned, current is applied to create acidic and basic zones and thus ablate tissue in the treatment zone. In embodiments comprising eight electrodes, the system may be used to create eight necrotic zones in a single deployment. Thus, the treatment may be performed with a single deployment, employing relatively slow treatment with respect to application of current but having relatively fast treatment time because all treatment zones may be formed substantially simultaneously. This decreases physician time and burden to deliver the treatment to patients.

In some embodiments for treatment of BPH, the cathode may be placed proximate the bladder neck or base of the prostate. A cathode so placed creates a large area of necrosis with less relative variation. Because of the edemic reaction at the cathode, the healing response and resorption of tissue into the body (and associated relief of symptomatic BPH) is accelerated. The area closest to the bladder neck in the prostate is responsible for the greatest contribution to lower urinary tract symptoms due to BPH. The anode may be placed closer to the verumontanum or as an indifferent electrode. Another embodiment includes placing the cathodes in the lateral posterior quadrant of the tissue relative to the urethra and placing the anodes in the lateral or lateral anterior quadrant of the tissue relative to the urethra. A treatment zone forms around each of the electrodes and diffuses out generally passively. Thus, the electrodes may be placed in the tissue relative to each other such that the treatment zones overlap and coalesce. In one embodiment an indifferent electrode is used as either the anode or cathode in addition to the electrodes in the catheter which create the treatment zones. The indifferent electrode can be a patch electrode that makes contact with the skin of the patient. In one embodiment the patch is placed on the buttocks of the patient. The indifferent electrode may have a substantially large surface area to reduce the electrochemical affect on the skin. In one embodiment indifferent electrode incorporates a flushing system to maintain a neutral pH at the surface of the skin-electrode interface.

Method of Treatment

Figure 5:
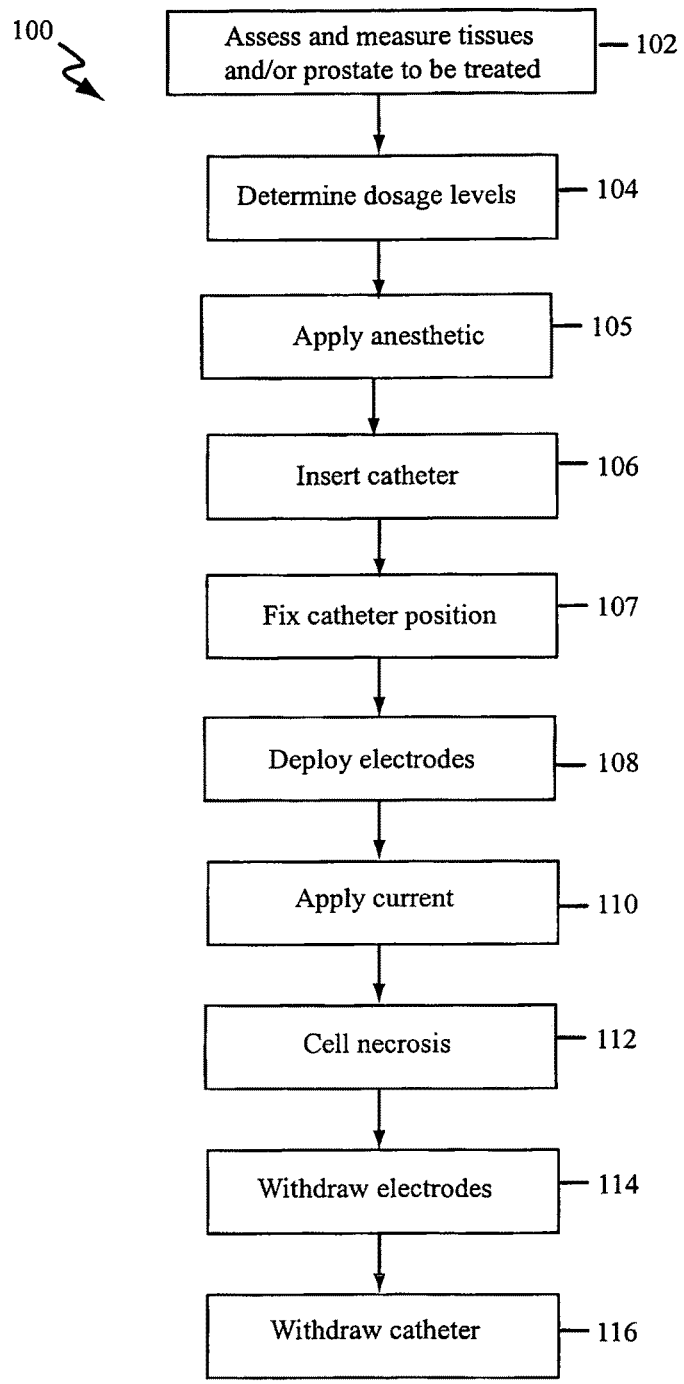
FIG. 5 illustrates a block diagram of a method for treating tissue, in accordance with one embodiment.

FIG. 5 illustrates a block diagram of a method 100 for treating tissue. In the embodiment shown, the method comprises assessing and measuring the prostate or other tissue to be treated [block 102], determining dosage levels [block 104], application of an anesthetic [block 105], inserting a catheter [block 106] and fixing the position of the catheter with a fixation element [block 107], deploying electrodes via the catheter [block 108], applying current to the electrodes to create acidic and basic treatment zones [block 110], cell necrosis [block 112], withdrawal of the electrodes [block 114], and withdrawal of the catheter [block 116]. It is to be appreciated that, in some embodiments, not all of these steps may be performed and/or additional steps may be performed. Further, in some embodiments, one or more of the steps may be performed in a manner other than specifically disclosed herein.

In treatment of BPH, prostate size may vary considerably and selection of appropriate number and size of electrodes to deploy may vary based on size of the prostate. Generally, using systems and methods such as disclosed herein, a minimum of 4 electrodes will be deployed. In some embodiments, eight electrodes, with eight associated treatment zones are provided and deployed in a single deployment. To evaluate the number and size of electrodes for deployment and/or dosage levels, it may be desirable to examine the patient to determine size of the tissue area to be treated. Such examination may be visual, tactile, or other. In one embodiment, examination may be done using a cystoscope, a tubular instrument used to visually examine the interior of the urinary bladder and urethra. In various embodiments, the location for electrode deployment may be determined by estimating the size and shape of the prostate through cystoscopy and/or transrectal ultrasound (TRUS) and/or other suitable imaging method. Other options include CT, MRI, PET, or X-ray. Treatment zone size may also be determined to minimize interaction with the prostate capsule and the prostatic urethra. Minimizing treatment interactions with the capsule and prostatic urethra will reduce the amount of irritative urinary symptoms after treatment. An appropriate system configuration thus may be selected based on the prostate size to be treated to minimize these interactions. Dosage levels may be determined based on the assessed treatment area. The desired treatment area can be determined by measuring the overall prostate dimension such as transverse width, sagittal length, and anterior to posterior height. Generally, the most important anatomical dimension to determine treatment may be the prostate transverse width. Diffusion through tissue is typically predictable, thus facilitating dosage setting.

In one embodiment the generator is configured to display the predicted areas of necrosis over an uploaded image from ultrasound. In other embodiments, other imaging devices may be used to provide such imagery. The size and shape of the treatment zone varies with the charge setting inputted into the generator. In some embodiments the generator is configured to communicate with an ultrasound machine overlaying the predicted treatment zone on the ultrasound image. In embodiments wherein the system is used for treatment of prostate, imaging may be used prior to insertion of the system. Such imaging may be, for example, a rectal ultrasound whereby the prostate is measured. Measurements of the prostate may then be compared to a table to determine appropriate length of insertion and dose for treatment.

Block 104 of FIG. 5 may include entry of input treatment parameters into the generator. In some embodiments, the generator may include switches, keys or buttons for the entry of one or more input treatment parameters by the user of the system and those input treatment parameters may be used by the generator to control the delivery of current. During treatment, the generator may compare measured treatment parameters with input treatment parameters to determine when to pause or stop the treatment. In one embodiment, the input treatment parameter may be dose (charge) in coulombs. During treatment, the generator stops treatment when the measured charge is greater than or equal to the charge entered by the user. In another embodiment, input treatment parameters may be current level and time. During treatment, the generator may stop treatment when the measured charge is greater than or equal to the product of the current level and time input parameters. In another embodiment, the input treatment parameter may be current level. During treatment, the generator may pause or stop treatment if the measured current level exceeds the current level input parameter. In another embodiment, the input treatment parameter may be time with a predetermined current level.

The following look-up tables can be a guide for determining the charge to be delivered and the length of insertion of the electrodes into prostates with varying transverse widths to optimize treatment.

Table 1 shows optimized treatment settings for a catheter which has electrodes that extend outward from the catheter generally perpendicular from the catheter body (Extension angle between 60 and 120 degrees) (The active length of the electrode is assumed to be 6 to 8 mm in this table):

TABLE 1

| Prostate Transverse Width (mm) | Dose or Charge (C) | Expected Treatment Zone Radius around each electrode (mm) | Electrode Extension Length (mm) |
|---|---|---|---|
| 30-40 | 36-48 | 5-7 | 13 |
| 40-50 | 40-52 | 6-8 | 16 |
| >50 | 48-60 | 7-9 | 20 |

Table 2 shows optimized treatment setting for a catheter which has electrodes that extend outward from the catheter towards the catheter tip with an extension angle of 45 degrees to 30 degrees. The active length of the electrode is assumed to be 6 to 8 mm in this table:

TABLE 2

| Prostate Transverse Width (mm) | Distal Electrode Insertion Point from Fixation Element in Bladder (mm) | Optimal Dose or Charge (C) per electrode | Expected Treatment Zone Radius around each electrode (mm) | Electrode Extension Length (mm) |
|---|---|---|---|---|
| >30 | 14-16 | 28-36 | 4-6 | 16 |
| >30 | 16-18 | 36-48 | 5-7 | 18 |
| >35 | 18-20 | 36-48 | 5-7 | 20 |
| >40 | 20-22 | 48-60 | 7-9 | 22 |

Table 3 shows optimized treatment setting for a catheter which has electrodes that extend outward from the catheter towards the catheter tip with an extension angle of 60 degrees to 45 degrees. The active length of the electrode is assumed to be 6 to 8 mm in this table:

TABLE 3

| Prostate Transverse Width (mm) | Distal Electrode Insertion Point from Fixation Element in Bladder (mm) | Optimal Dose or Charge (C) per electrode | Expected Treatment Zone Radius around each electrode (mm) | Electrode Extension Length (mm) |
|---|---|---|---|---|
| >30 | 12-14 | 28-36 | 4-6 | 16 |
| >35 | 14-16 | 36-48 | 5-7 | 18 |
| >40 | 15-17 | 36-48 | 5-7 | 20 |
| >45 | 16-18 | 48-60 | 7-9 | 22 |

Table 4 shows optimized treatment setting for a catheter which has electrodes that extend outward from the catheter towards the catheter tip with an extension angle of 30 degrees to 15 degrees. The active length of the electrode is assumed to be 6 to 8 mm in this table:

TABLE 4

| Prostate Transverse Width (mm) | Distal Electrode Insertion Point from Fixation Element in Bladder (mm) | Optimal Dose or Charge (C) per electrode | Expected Treatment Zone Radius around each electrode (mm) | Electrode Extension Length (mm) |
|---|---|---|---|---|
| >30 | 16-18 | 20-28 | 3-5 | 16 |
| >30 | 18-20 | 24-32 | 4-5 | 18 |
| >30 | 20-22 | 28-36 | 4-6 | 20 |
| >30 | 22-24 | 28-36 | 4-6 | 22 |

To determine how many electrodes should be used to treat a prostate a cystoscopy should be done to measure the distance between the bladder neck and the verumontanum. If the measurement is less than 2.5 cm the patient is not well suited to be treated with a catheter that has electrodes that angle away from the catheter of less than 60 degrees upon electrode extension (extension angle). Table 5 shows the number of electrodes that should be used in treating prostates with varying distances between the bladder neck and verumontanum with catheters with different extension angles. This assumes that 4 electrodes are placed in each plane along the urethra and each plane is spaced between 6 and 12 mm.

TABLE 5

| Cystoscopy Measurement between bladder neck and verumontanum (cm) | Optimal # of Electrodes in catheter with extension angle between 90 and 60 degrees | # of Electrodes in catheter with extension angle between 60 and 45 degrees | # of Electrodes in catheter with extension angle between 45 and 30 degrees | # of Electrodes in catheter with extension angle between 30 and 15 degrees |
|---|---|---|---|---|
| <2.5 | 4 | NA | NA | NA |
| 2.5-4.5 | 8 | 4 | 4 | 4 |
| >4.5 | 12 | 8 | 8 | 4 |

Figure 6A:
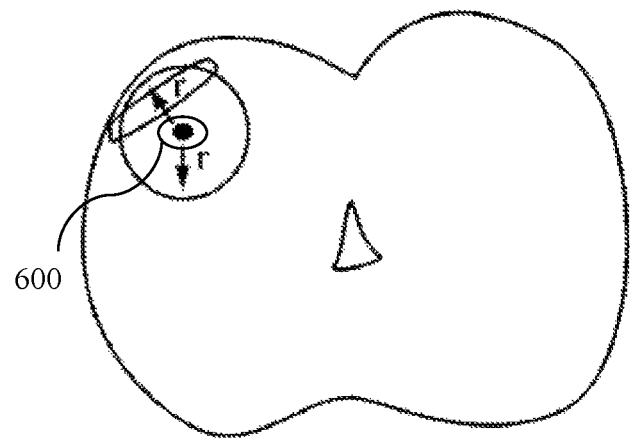
FIG. 6a illustrates a treatment zone for a dose that just touches the capsule, in accordance with one embodiment.
Figure 6B:
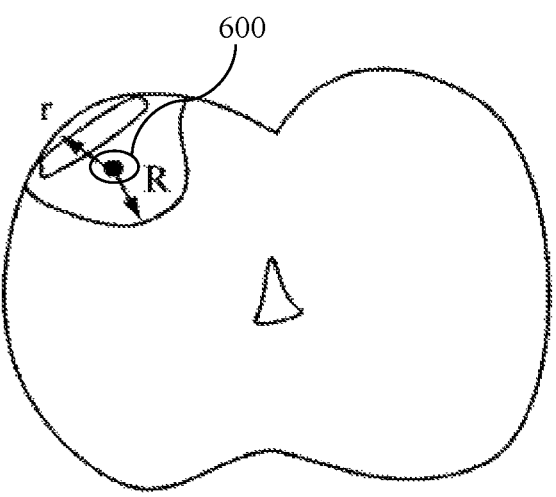
FIG. 6b illustrates a treatment zone for a dose that is overdosed, in accordance with one embodiment.

In some embodiments, the prostate capsule may be used as a safety margin to deliver DC ablation to the periphery zone of the prostate. Because of the capsule around the prostate and the creation of ions using DC ablation, the prostate can be overdosed to effectively treat the periphery zone, especially for applications for treating cancerous tissue. This overdose may range from approximately 160% to approximately 260% of the dose for allowing the ionic gradient to reach the prostate capsule. FIGS. 6a and 6b illustrate treatment zones for a dose that just touches the capsule (FIG. 6a) and a dose that is overdosed (FIG. 6b). A cancer is shown in each of the figures with the treatment radius of each electrode being suitable for treating the cancer. Each of FIGS. 6a and 6b show the same electrode placement. Dose typically may be determined assuming a radius that reaches the capsule but does not extend past the capsule, radius r shown in FIG. 6a. The dose may be increased to effectively increase radius but the radius r towards the capsule will not extend past the capsule because of the anatomy of the capsule. Thus, as shown in FIG. 6b, radius r towards the capsule remains the same but radius R away from the capsule increases. In one embodiment, the treatment radius in FIG. 6a is achieved using a dose of 30 C and results in a radius r of 6 mm. In one embodiment, the treatment radius R in FIG. 6b is achieved using a dose of 78 C and results in a radius R of 10 mm. An algorithm may be developed using routine experimentation for current and charge balancing to produce the desired treatment zone.

In some embodiments, the area for treatment may be prepared for treatment, as shown and discussed in copending U.S. patent application Ser. No. 12/544,134, herein incorporated by reference in its entirety. Unlike many ablation methods, DC ablation does not use extremes of temperature to cause necrosis and therefore can be used safety adjacent vascular structures.

In some embodiments, a saline solution or saline gel may be introduced to provide additional safety margin where ablation of tissue is not desired. In some embodiments, a saline solution with a pH of 7 may be provided adjacent to a treatment area. This substantially prevents the acidic and basic treatment zones from advancing into that area. The neutral pH of the saline dilutes the advancing acidic and basic gradient to a point which does not create necrosis in the tissue in irrigated areas. The saline solution may be delivered to an area by any suitable method. For example, in a first embodiment, saline may be introduced into a body lumen where preservation is desired, such as the urethra, through the therapy delivery catheter or through a separate dedicated irrigation catheter. In a second embodiment, saline may be injected through a needle into a capsule to preserve a certain region within the capsule. In a third embodiment, saline may be injected into a body cavity adjacent to the capsule of the body being treated to preserve adjacent tissue, such as the rectum. Saline saturation of the treatment area may further be done if a concern for dehydration arises. In other embodiments, distilled water may be used as an alternative to saline solution. As discussed with respect to application of current to the electrodes, muscle contractions may arise during treatment. Generally, muscle contractions are undesirable during treatment. A nerve block may be used in some embodiments to minimize patient discomfort during treatment. In some embodiments, anesthetic may be applied. It is to be appreciated, however, that the system and method disclosed herein are significantly more tolerable to patients than previous methods of BPH treatment and may be performed with minimal anesthetic. For example, the methods disclosed herein may be performed with the patient conscious.

Pain management during treatment according to the systems and methods provided herein may be done by local anesthesia. For example, in some embodiments application of anesthesia may comprise introducing a topical anesthetic gel (e.g. lidocaine) into the urethra. This may be done, for example, by injecting into the urethra or coating a catheter that would be inserted and removed prior to inserting the treatment catheter. Thus, in various treatment applications, anesthetic gel may be applied to a transperineal, transrectal, or transurethral catheter for delivery to the prostate or other tissue. In other embodiments, a nerve block may be injected locally or a sedative may be orally ingested or intravenously delivered.

In some embodiments, the method may include visualization, for example to facilitate placement and positioning of the system. Accordingly, visualization elements may be provided as part of the system. Particularly in systems employing a plurality of electrodes, such as eight electrodes, correct positioning can impact results. The positioning of the system impacts positioning of all electrodes and, thus, positioning of all necrotic zones. Accurate placement of transurethral catheters can be optimized with the use of a transrectal ultrasound. Ultrasound imaging may be optimized by designing the catheter or other portion of the system for imaging. The ability to image the system as the system is placed can enhance results and improve safety.

Magnetic resonance imaging may alternatively be used to verify position and treatment for the system for treating tissue as provided herein. In accordance with one method, the catheter is placed and the electrodes are inserted. The patient is positioned for MRI imaging and DC ablation is activated at low levels. MRI is performed, tuned to measure the electromagnetic field of DC current, and therapy is paused. The position of electrodes and treatment region are verified through examination of the MRI image. Generally, the imaging sequence may include electrical currents, via induced magnetic field, or $H^+$ concentration, such as for conventional MRI images, or other sequences such as known to those skilled in the art.

Angular orientation of the catheter and electrode array can be verified by a physical marker on the body of the catheter or handle that is exposed outside the body. In certain embodiments, this may be a linear marking or a bubble indicator. Such indicator may also be internal to the body and may be seen through imaging such as ultrasound, MRI, CT, or X-Ray The system may be deployed by inserting a catheter proximate the tissue to be treated such that the treatment zone of an electrode deployed from the catheter overlaps the tissue to be treated. The catheter may have a handle provided at a proximal end thereof for handling by a physician, such as a surgeon or urologist. The catheter is inserted until location of the electrodes, as determined with respect to the catheter, is at the desired tissue for treatment. Thus, for example for BPH treatment, the catheter may be inserted into the urethra through the penis until location of the electrodes is in the urethra proximate the prostate. In some embodiments, the catheter may include an anchor for anchoring the catheter in place during treatment. For example, a pair of pneumatically or hydraulically activated balloons may be used to anchor the catheter.

After anchoring (if done) and placement confirmation, the electrodes may be deployed from the catheter. Electrode deployment may be linear, rotation, or a hybrid of linear and rotational. Deployment of the electrodes may be triggered, for example, using a push button trigger, a slide mechanism, or other on the catheter handle. In some embodiments, the catheter may be partially retracted or advanced to expose electrodes provided on a support structure within the catheter. In some embodiments, the electrodes may be deployed through routing holes provided in an outer sheath or sleeve (e.g., outer sheath 600) that surrounds the catheter. The electrodes may extend generally outwardly from the catheter to enter the tissue to be treated. The position of the electrodes in the tissue affects the treatment zone. More particularly, the treatment zone generally surrounds the electrodes.

In some embodiments, the inserted length of all deployed electrodes may be approximately equivalent. This permits the electrodes to be deployed with a single simple mechanism. In other embodiments, multiple insertion lengths may be used. Such varied insertion lengths may be achieved, for example, with multiple insertion mechanisms or various cam and/or gearing mechanisms. Treatment zones around each electrode may be the same size or may vary one to another. The amount of charge to each electrode may be controlled to influence treatment zones. For example, where varying sizes of treatment zones are desired and each electrode has the same length, different currents may be supplied to the electrodes from independent current sources. Further, in some embodiments, portions of the electrode may be insulated, for example portions closest to the catheter to increase the distance from the active area of the electrode to a structure that is wished to be preserved, for example the urethra. This facilitates preservation of the urethra to minimize post-procedural irritative symptoms such as dysuria, hematuria, and urinary urgency.

After the electrodes have been positioned, current is applied to create acidic and basic zones. Specifically, direct electrical current is applied to the electrodes. In some embodiments, the direct electrical current is applied simultaneously to all electrodes from isolated current sources having individually selectable polarity and charge delivery. The applied current creates an acidic zone around the anode and an alkaline or basic zone around the cathode. Generally, the treatment zone tends to follow, and not cross, a tissue plane. Accordingly, using DC ablation, treatment may be up to the tissue plane. The sizes of the necrotic zones are based on the amount of charge delivered to each electrode, where charge (coulombs) equals current (amperes) multiplied by time (seconds). In some embodiments, the applied current is at a relatively low level such as between approximately 1 mA and approximately 100 mA. Generally, treatment time increases as current decreases. Treatment time decreases as the number of electrodes increases. Treatment time may decrease if impedance decreases and the voltage compliance of the constant current system is low or the system utilizes constant voltage. In accordance with one embodiment, BPH treatment is achieved in approximately 30 minutes when using a 4, 6, 8, or 12 electrode array at 20 mA to deliver the treatment of 36 coulombs per electrode pair. Treatment time is reduced to 24 minutes when the current is increased to 25 mA and delivering 36 coulombs per electrode pair. The systems and methods disclosed herein employ slow, low current, low power treatment. Because of the plurality of electrodes and the substantially simultaneous treatment through all electrodes, total treatment time is nevertheless kept low. Table 6 shows the relationships between current, power, time, charge, and number of electrodes.

TABLE 6

| Current per Electrode Pair (mA) | Impedance per Electrode Pair (ohms) | Power per Electrode Pair (mW) | Time (minutes) | Charge per Electrode Pair (coulombs) | Number of Electrode Pairs | Total Charge (coulombs) |
| --- | --- | --- | --- | --- | --- | --- |
| 10 | 400 | 40 | 30 | 18 | 1 | 18 |
| 10 | 700 | 70 | 30 | 18 | 2 | 36 |
| 10 | 1000 | 100 | 30 | 18 | 3 | 54 |
| 25 | 400 | 250 | 30 | 45 | 1 | 45 |
| 25 | 700 | 437.5 | 30 | 45 | 2 | 90 |
| 25 | 1000 | 625 | 30 | 45 | 3 | 135 |
| 50 | 400 | 1000 | 30 | 90 | 1 | 90 |
| 50 | 700 | 1750 | 30 | 90 | 2 | 180 |
| 50 | 1000 | 2500 | 30 | 90 | 3 | 270 |

The power applied to the electrodes is low compared to prior methods for treating BPH. More specifically, the power applied in accordance with systems and methods disclosed herein is on the order of milliwatts in the range of 20 to 3200 mW of power per electrode pair. The power typically used for each electrode pair is between approximately 190 mW (25 mA into a 300 ohm tissue impedance) to 1600 mW (40 mA into a 1000 ohm tissue impedance). A common impedance level seen in tissue is 400 ohms, and treating with 50 mA equates to a required power output of 1000 mW. This low power of treatment delivery allows for insignificant heat transfer to occur between the device and body tissues. This reduces or eliminates pain and discomfort from the heating of surrounding tissues during treatment that are experienced with thermal technologies utilizing significantly higher power. It also reduces or eliminates scarring and long healing times associated with a thermal wound. RF and microwave technologies using thermal energies to create necrosis in soft tissue often have power ranges between 15 and 75 W. The amount of power delivered by a thermal ablation system is not based directly on the measurement of the power delivered, but is based on the temperature measurement resulting from the power delivered. In contrast, the amount of charge delivered by the DC ablation system is based directly on the measurement of the charge delivered, allowing for more precise control of the size of the necrotic zones.

In order to create substantial cell death a temperature of at least 45 degrees C. or an 8 degree increase in tissue temperature must be maintained for approximately one hour.

Figure 7:
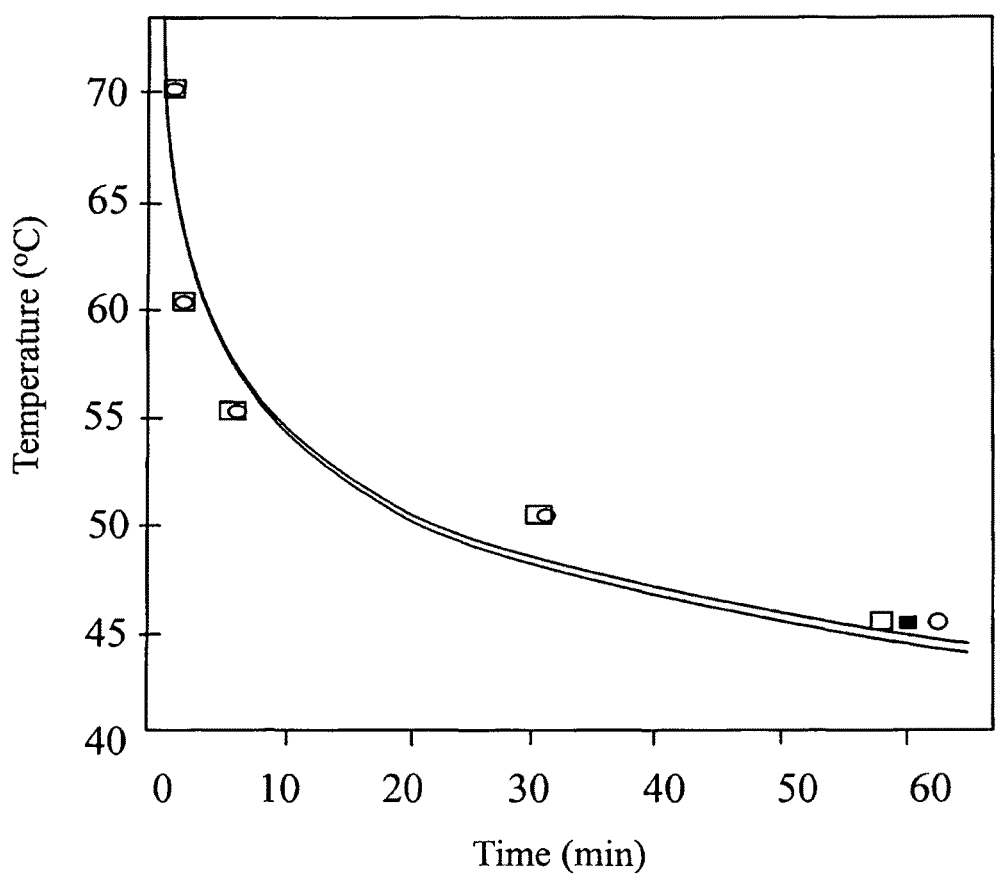
FIG. 7 illustrates a table showing time-temperature relationship for 90% normalized cell death in human BPH tissue from heating.

Substantial cell death occurs over 10 minutes at 55 degrees C. FIG. 7 illustrates the relationship between time and temperature. More specifically, FIG. 7 illustrates the time-temperature relationship for 90% normalized cell death in human BPH tissue from heating. At greater than 100 degrees C. the water present in the tissue boils and can cause impedance increases such that thermal therapy becomes intermittent. RF thermal ablation devices attempt to create tissue temperatures approaching 100 degrees C. to create necrosis with minimal treatment time. RF thermal ablation treatments can last between 1.5 and 5 minutes.

DC ablation applied with up to 50 mA only results in a maximum increase of 4 to 5 degrees C. in the tissues surrounding the electrodes. Lower currents will cause a lesser change in tissue temperature in the range of 0 to 3 degrees C. This mild increase in temperature does not create necrosis or act as a mechanism in ablating the tissue over the duration of the DC ablation treatment. These calculations are dependent on tissue type and vascularization of the tissue.

Inducing high localized temperatures causes surrounding tissues to also substantially increase in temperature. This may lead to collateral damage of structures outside of the intended treatment area such as, in the case of BPH treatment, the erectile nerves, rectum, or external sphincter. Devices that use radiated energy to heat tissues such as microwave require a rectal temperature probe to ensure that the rectum does not exceed an unsafe temperature. The high temperatures surrounding the treatment area also leads to a burning sensation in the pelvic region. Generally at 45 degrees a heat sensation is perceived. This is exceeded at the prostate capsule during thermal ablation treatments. A non-thermal DC ablation system, such as disclosed herein, does not have either of these concerns due to the low power that is delivered.

A single treatment can be done with no repositioning of the catheter and can be completed in no less than 8 minutes assuming delivering 24 C per electrode at the rate of 50 mA. A single treatment with no catheter repositioning can take as long as 100 minutes assuming delivering 60 C per electrode at a rate of 10 mA. It should be appreciated that, generally, no single treatment should last longer than 45 minutes for patient comfort and physician burden. Thus a treatment of 60 C should be completed at a minimal rate of 22 mA. If more treatment is required the catheter may be repositioned and a second treatment started.

In some embodiments, the electrodes may be generally cylindrical. The shape of the treatment zone for a cylindrical electrode is a cylinder with hemispheric ends and approximates an ellipsoid. By adjusting the electrode length and/or charge delivered, the shape of the ellipsoid can be controlled to make shapes that are cylindrical, oval, or spherical. As current is applied to the electrodes, an ellipsoid treatment zone forms around each electrode. The length of the ellipsoid is approximately equal to the length of the exposed electrode plus the diameter of the treatment zone. If the electrode length is significantly longer than the diameter of the treatment zone, the shape of the zone will be nearly cylindrical. The ends will be round (hemispheres) but the shape will be long and narrow like a cylinder. As the treatment continues, the diameter and length of the zone grow. As a percentage of the previous dimension, the diameter grows faster than the length. As this continues, the shape of the treatment zone becomes more oval than cylindrical and eventually becomes nearly spherical.

Figure 8A:
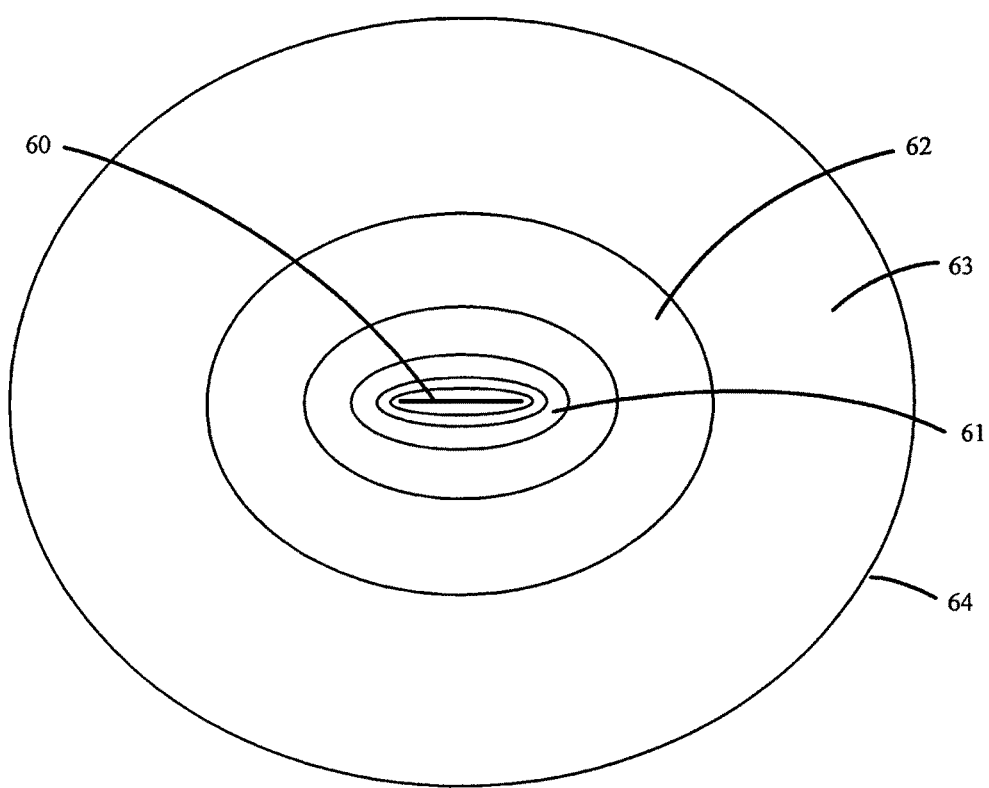
FIG. 8a illustrates changes to the shape of the treatment zone, in accordance with various embodiments.

FIG. 8a illustrates a treatment zone around an electrode 60 wherein the treatment zone is, for the purposes of illustration, divided into 4 zones 61, 62, 63, and 64, extending radially outward from the electrode 60. As shown, the treatment zones 61, 62, 63, and 64 change shape as they extend away from the electrode 60. The zone 61 closest to the electrode is nearly cylindrical while the zone 64 farthest from the electrode is nearly spherical. Accordingly, with electrodes of equal length, treatment zone size as well as shape may vary with different applied currents when treating for an equal amount of time. Treatment shape will vary as well due to the proximity of tissue planes that impede the diffusion of the treatment.

Figure 8B:
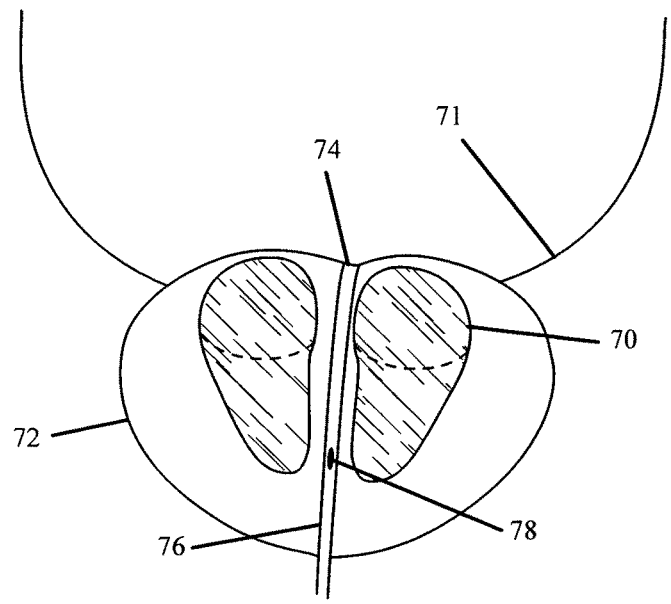
FIG. 8b illustrates coronal tracing of a treatment zone, in accordance with one embodiment.
Figure 8C:
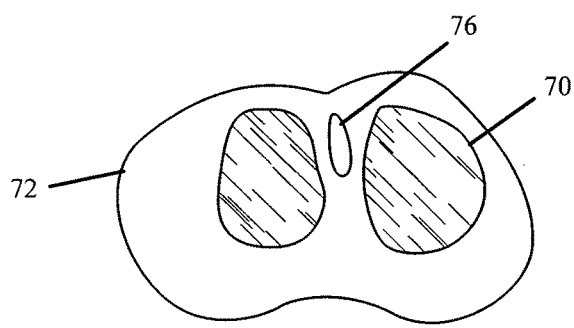
FIG. 8c illustrates transverse tracing of a treatment zone, in accordance with one embodiment.

FIGS. 8b and 8c illustrate a suitable area to create necrosis in the prostate to relieve symptomatic BPH. FIG. 8b illustrates coronal tracing of a treatment zone. FIG. 8c illustrates transverse tracing of a treatment zone. As shown, the treatment zones 70 may be in the lateral lobes 72 of the prostate adjacent to the bladder neck 74 and along the urethra 76 to the verumontanum 78. FIG. 8b also illustrates the bladder 71 for reference. Treating in the treatment zones 70 maximizes symptom relief obtained by treatment as the necrotic tissue is reabsorbed by the body and pressure is removed from the urethra. The urethral interaction of the treatment may be minimized to reduce transient irritative symptoms such as hematuria, dysuria, and urinary urgency. Amount of charge delivered, electrode shape and size, electrode array, electrode positioning, number of electrodes, current level, and electrode insertion length are all factors in treatment.

In another embodiment the electrodes may be staggered such that they do not align. In another embodiment 3, 5, 6, 7, 9, 10, 11, and 12 electrode arrays may be utilized to treat the prostate with DC ablation through the urethra and into the lateral lobes of the prostate. These embodiments are optimized to created treatment zones as prescribed in FIGS. 8b and 8c.

Figure 9A:
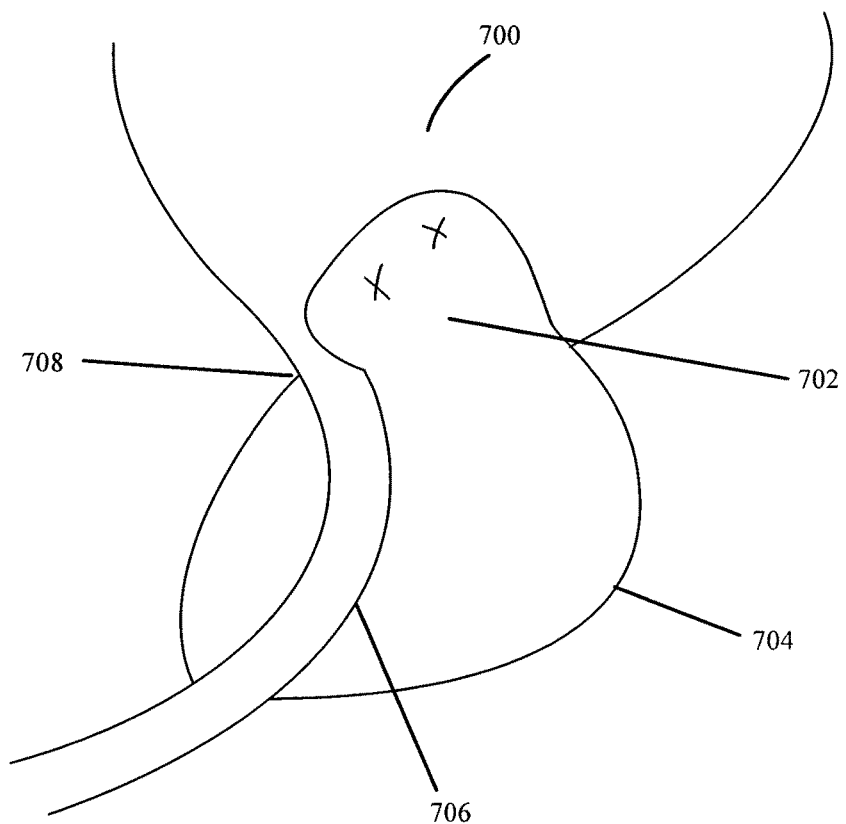
FIG. 9a illustrates a prostate anatomy with a large median lobe that extends up in the bladder.

In some patients it may be desirable to treat the median lobe of the prostate instead or in addition to the lateral lobes. FIGS. 9a-9d illustrate median lobe treatment. FIG. 9a shows a prostate anatomy 704 with a large median lobe 702 which extends up into the bladder 700. A large median lobe 702 can cause a urinary obstruction of the prostatic urethra 706 at the bladder neck 708. Ablating the median lobe can be accomplished using DC ablation by using a modified method and system for treating the lateral lobes as previously described.

Figure 9B:
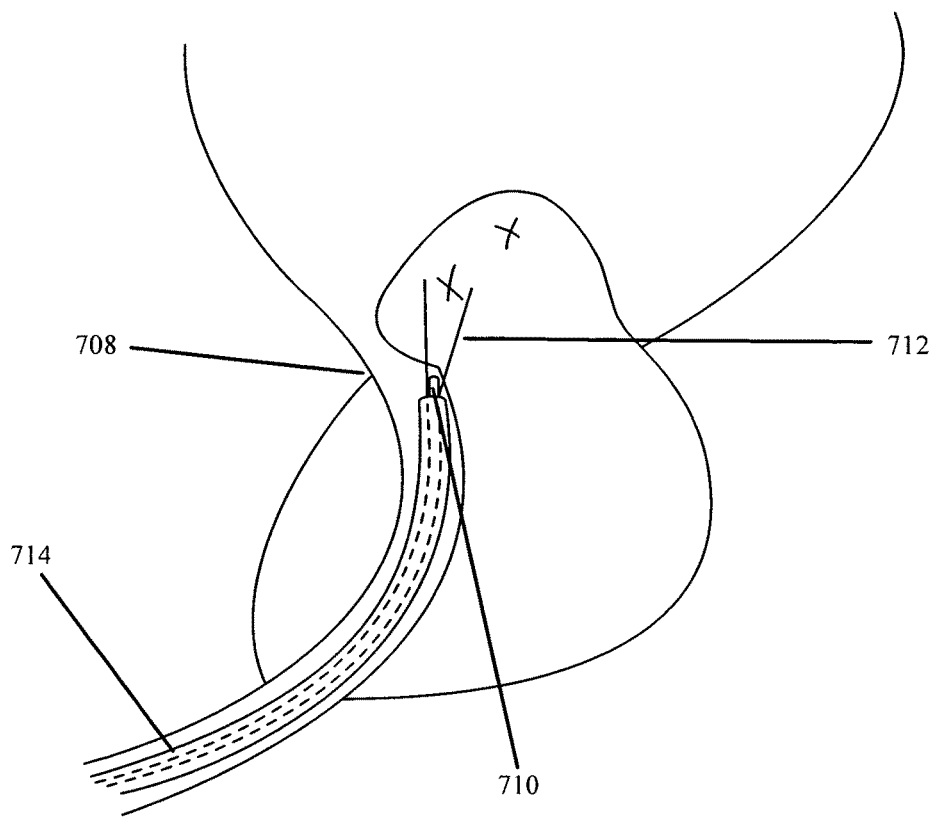
FIG. 9b illustrates positioning of a system for treatment of the median lobe, in accordance with one embodiment.
Figure 9C:
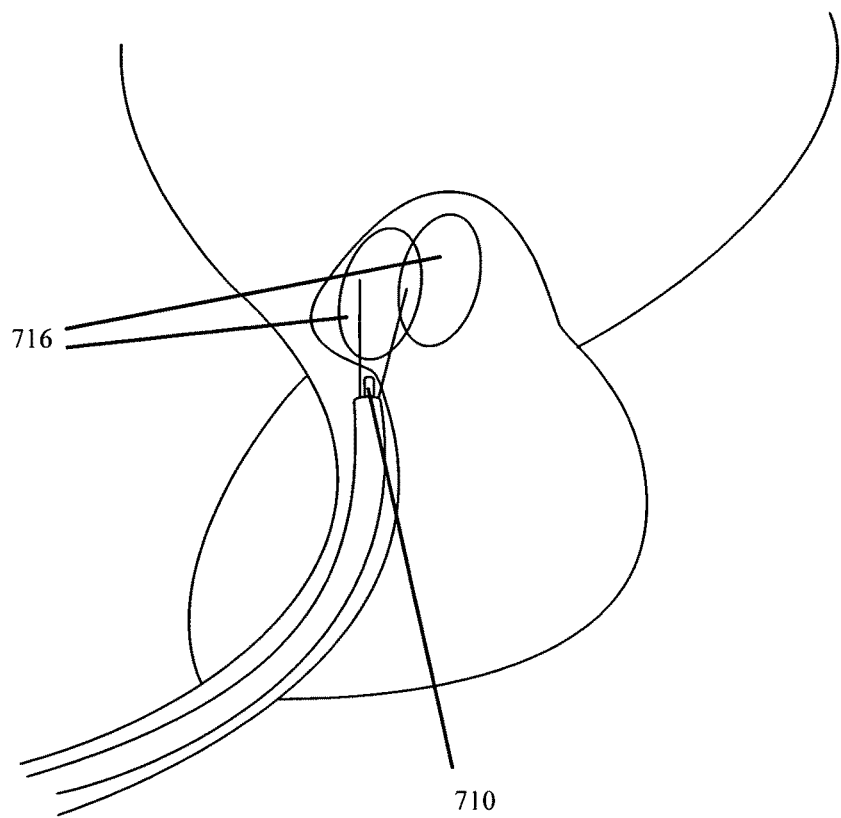
FIG. 9c illustrates treatment zones created through treatment of the median lobe, in accordance with one embodiment.

FIG. 9b illustrates positioning of a system for treatment of the median lobe. FIG. 9c illustrates treatment zones created through such treatment. Treating the median lobe of the prostate can be accomplished using methods described herein. As a preliminary matter, it may be useful to assess the size and position of the median lobe through visualization of the median lobe through Ultrasound, CT, MRI or cystoscopy. A transurethral delivery catheter 714 is routed in proximity to the bladder neck 708 and the area to treat identified by inserting a cystoscope 710 through or adjacent to the delivery catheter. A plurality of electrodes 712, for example between 2 and 4 electrodes, may then be extended into the median lobe under cystoscopy guidance. Insertion may be done either through the urethra near the bladder neck or from the bladder back into the median lobe. After the electrodes are placed a dose or charge of 15 to 60 coulombs per electrode may be delivered creating treatment zones 716 in the median lobe as shown in FIG. 9c. The catheter may be anchored to prevent the electrodes from moving during treatment. After treatment is completed the catheter and cystoscope is removed from the body.

Figure 9D:
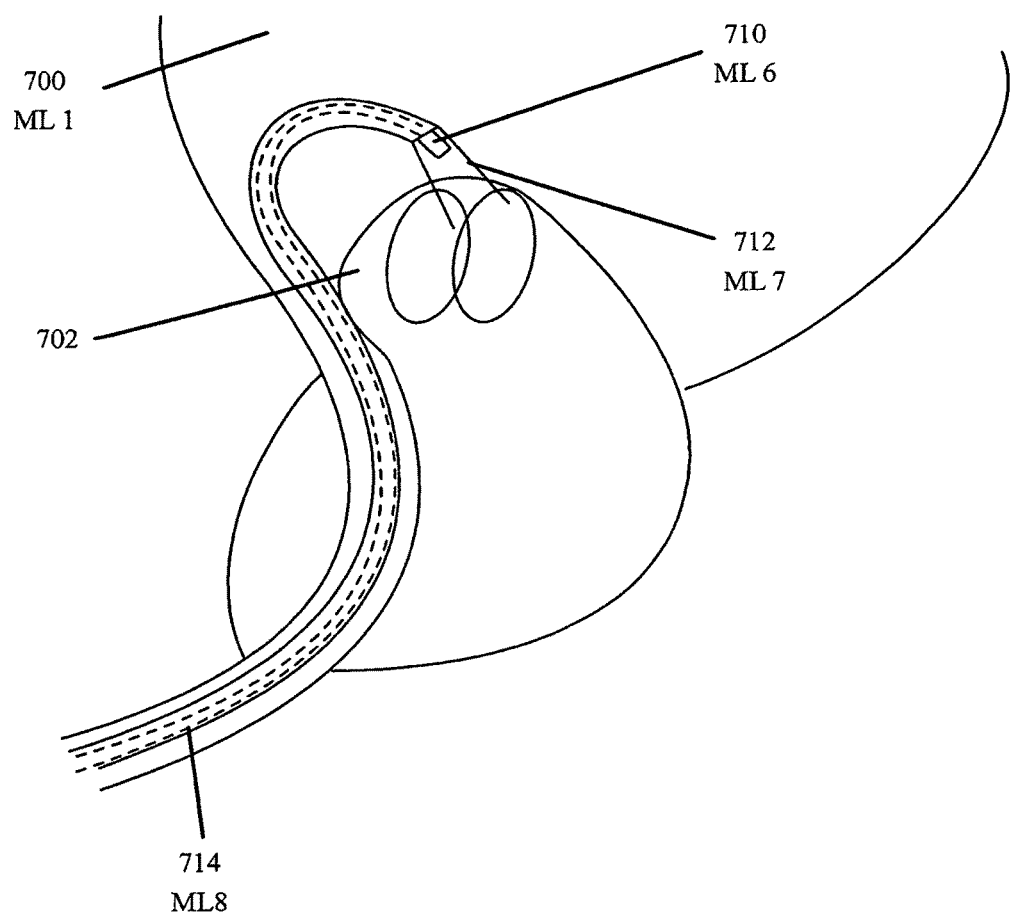
FIG. 9d illustrates an alternative treatment method for treating the median lobe, in accordance with one embodiment.

FIG. 9d illustrates an alternative treatment method for treating the median lobe. As shown, the delivery catheter 714 may be routed into the bladder 700 and then curved back towards the median lobe 702 where the electrodes may be inserted under guidance from a cystoscope.

As may be appreciated by those skilled in the art, similar systems and methods may be used for ablation of tissue in several different areas of the body. Such areas may include, for example, the trachea, stomach, esophagus, rectum, colon, intestine, bladder, uterus, and other tissues accessible from a lumen.

Figure 10A:
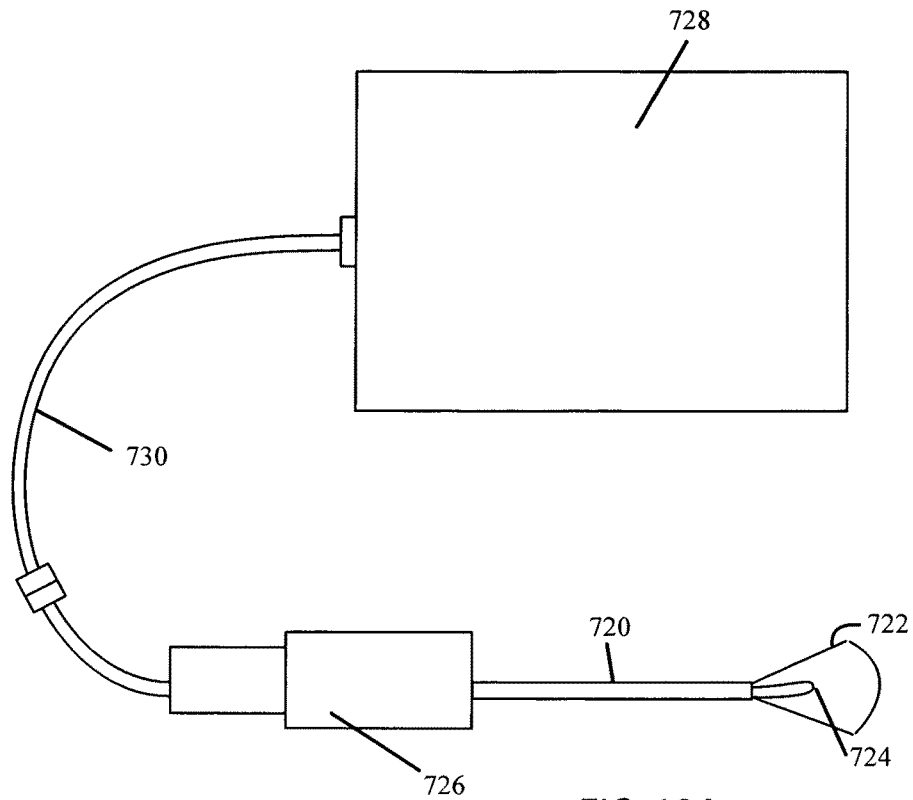
FIG. 10a illustrates a perspective view of a system for median lobe treatment, in accordance with one embodiment.
Figure 10B:
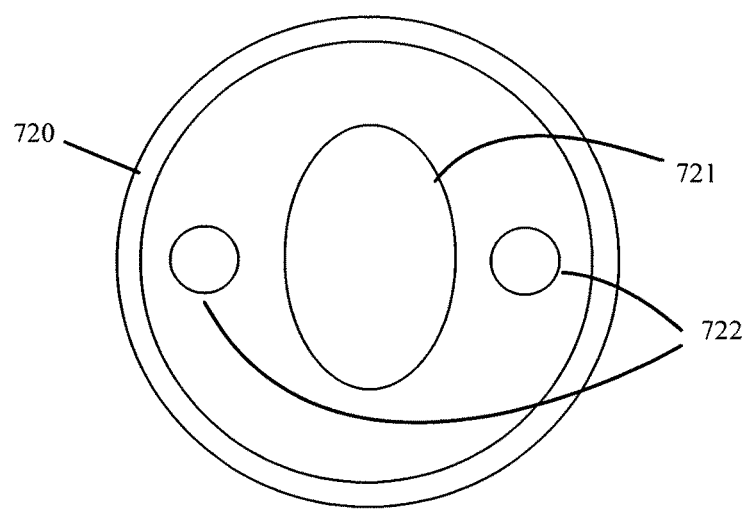

FIGS. 10a and 10b illustrate a specific embodiment of the delivery catheter for a system for treating the median lobe. FIG. 10a illustrates a perspective view and FIG. 10b illustrates an end view. As shown, the system may include a semi-flexible catheter 720 and a plurality of electrodes 722 positioned for extension from the distal tip of the catheter. In some embodiments, between 2 and 4 electrodes may be provided. A cystoscope 724 may be routed down the center of an open lumen 721 of the delivery catheter. The electrodes 722 may be actuated by a mechanism 726 which remains outside of the body during treatment. The delivery catheter is connected to a generator 728 by an extension cable 730. The same generator can be used in the median lobe system as the system for treating the lateral lobes previously described.

In some embodiments, the gas generation and diffusion through tissue can be used to mark the necrotic region. By calibrating current and time to tissue type, the treatment zone (or area of necrosis) can be visualized on ultrasound. As discussed, the gas created during DC ablation diffuses through tissue being treated until it becomes absorbed in solution with the fluids present in the tissue. By controlling the rate of therapy (current) and the total therapy delivered, the region of gas bubbles in the tissue can be correlated to the area of necrosis. Such visualization may be used, for example, when DC ablation is used to treat benign and malignant tumors.

In some embodiments, one anode and one cathode are provided per current source. This may facilitate control of the treatment zone size. In other embodiments, more than one anode and one cathode are provided per current source. This may reduce the likelihood of poor tissue contact during treatment. If more than 2 electrodes are used per current source, current may be directed to specific electrodes of the same polarity by making some electrodes have higher (or lower) impedance than others. This may be accomplished by varying configurations of the electrodes, for example by creating different surface textures on different electrodes, by providing a means for venting gases via some electrodes but not others, etc.

In various embodiments, size of treatment zone may be customized for specific treatment positions of the electrodes. For example, in treatment of BPH, smaller treatment zones may be formed near the prostate base and apex and larger zones may be formed in bulkier areas. Such varied treatment zone sizes may be provided by using different electrode sizes, differing numbers of electrodes, differing current or charge delivery, or by varying other process or system parameters. For example, shorter electrodes may be used at the distal and proximal ends and longer electrodes may be used in the middle band(s), as shown in the embodiment of FIG. 4c. In an alternative embodiment, fewer electrodes can be used at distal and proximal ends and more electrodes in the middle band(s). In a further embodiment, less charge may be delivered to electrodes at distal and proximal ends and more charge may be delivered to electrodes in middle band(s). In yet a further embodiment, the electrodes at distal and proximal ends may be programmed as anodes and those in the middle band(s) as cathodes.

DC current ablates tissue by imparting extreme pH (<5 or >9 to 10) into the tissue surrounding the electrode. The area surrounding the electrode affected by the extreme pH is referred to as the treatment zone. In some embodiments, the system may be deployed to provide overlapping polarity treatment zones. Such overlapping may optimize the radius of the treatment zone for tissue ablation. When DC ablation electrodes are placed in close proximity, the extreme pH zones grow. When they overlap for a paired electrode, the zones increase in radius more readily than when separate for a given dose.

Figure 11:
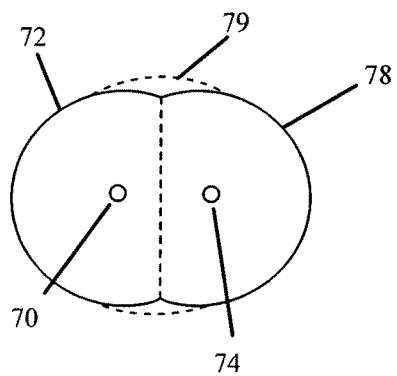
FIG. 11 illustrates overlapping treatment zones, in accordance with one embodiment.

FIG. 11 illustrates a radius of a combined treatment zone at the pH interface. The treatment zone may increase approximately 10-20% in radius. Specifically, FIG. 11 illustrates a first electrode 70 with a first pH extreme 72, a second electrode 74 with a second pH extreme 76, and a typical treatment radius 78. FIG. 11 further illustrates the increased radius 79 of the combined treatment zone (shown by the dotted line).

Similarly, in other embodiments, the anode and cathode may be placed proximate one another. By placing the anode and cathode (opposite polarity electrodes) in close proximity to one another, extreme pHs can be achieved to necrose tissue. The opposite pH levels help to neutralize one another to decrease the amount of time it takes for the surrounding tissue to return to normal conditions.

Figure 12:
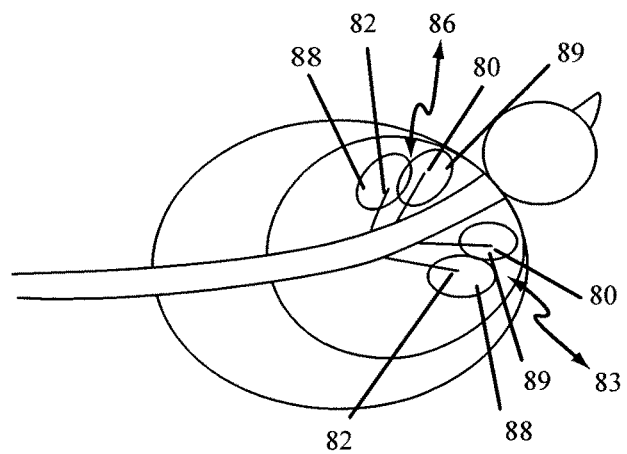
FIG. 12 illustrates electrodes placed in close proximity, in accordance with one embodiment.

FIG. 12 illustrates an embodiment with two anodes 80 and two cathodes 82. In one treatment area 83, an anode 80 is placed proximate a cathode 82, for example spaced between approximately 2 and approximately 20 mm from one another. The same set up is provided in a second treatment area 86—an anode 80 placed proximate a cathode 82. As a result, in each treatment area 83 and 86, a high pH zone 88 and a low pH zone 89 each arise proximate to the other. The zones 88 and 89 likely overlap one another. In the area of zone overlap, the pH of the tissue can return to normal within, for example, hours of the DC ablation procedure.

Figure 13A:
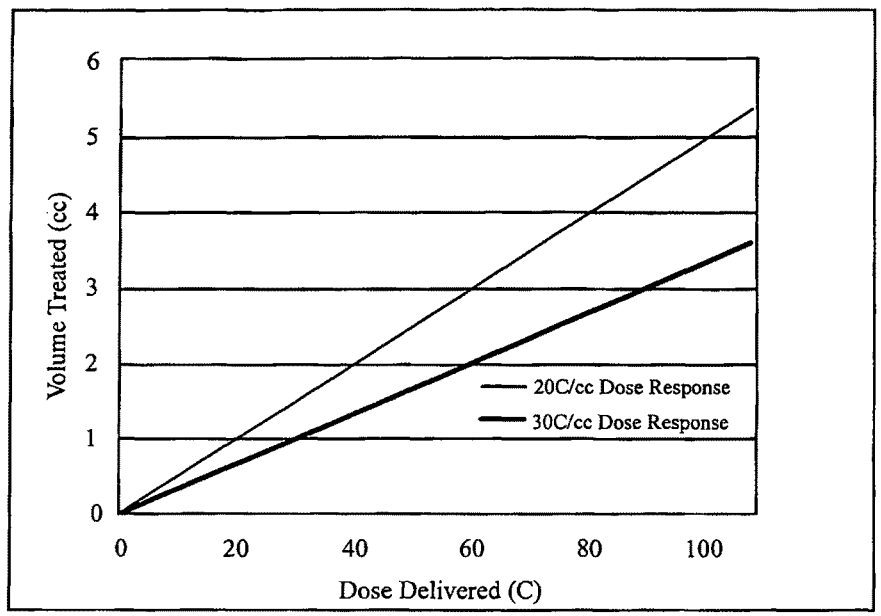
FIG. 13a illustrates dose delivered versus volume of tissue treated, in accordance with one embodiment.
Figure 13B:
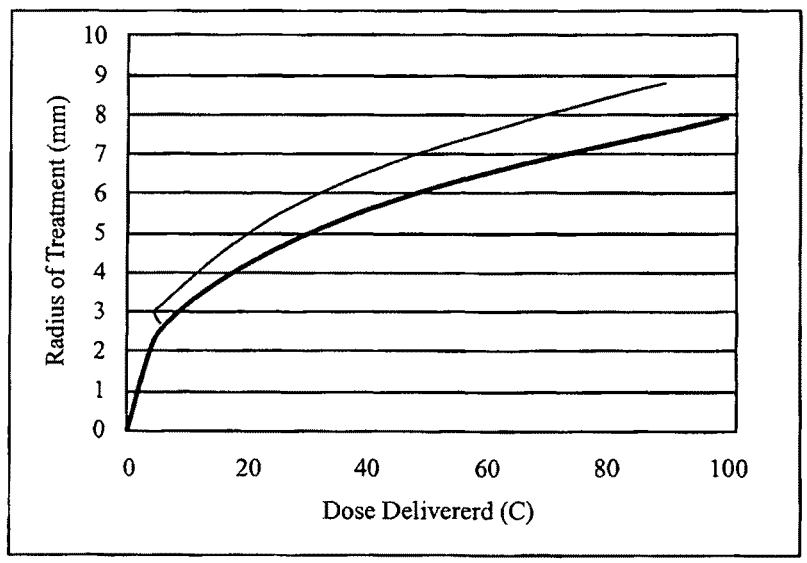
FIG. 13b illustrates dose delivered versus expected radius of treatment for a 6 mm electrode in prostatic tissue, in accordance with one embodiment.
Figure 13C:
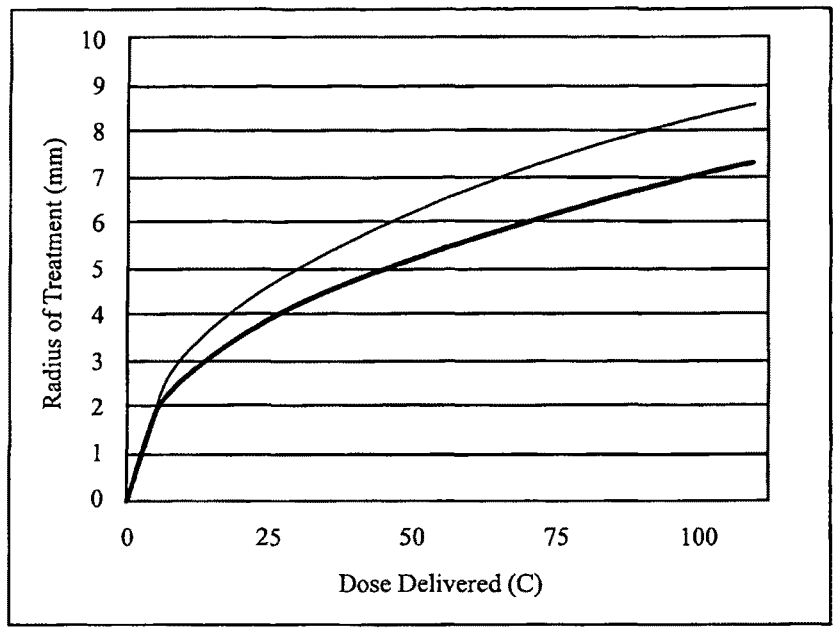
FIG. 13c illustrates dose delivered versus expected radius of treatment for 12 mm electrode in prostatic tissue, in accordance with one embodiment.
Figure 13D:
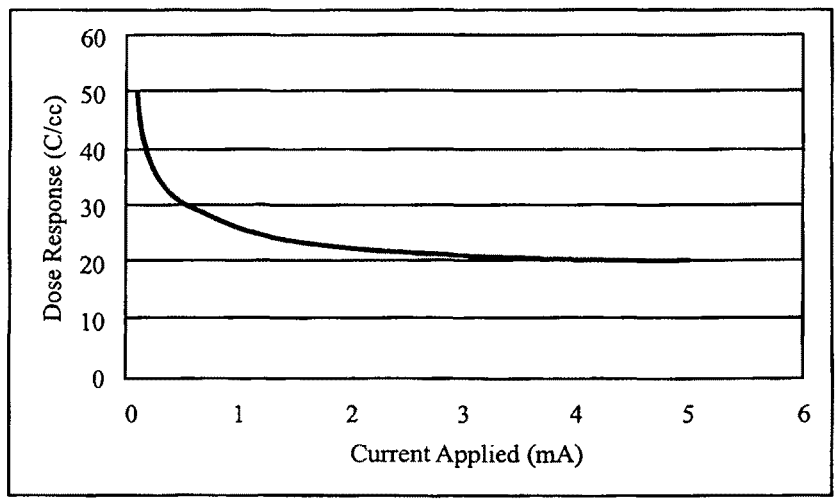
FIG. 13d illustrates current applied versus dose response, in accordance with one embodiment.

FIGS. 13a through 13d illustrate various effects and relationships of dosage. FIG. 13a illustrates the dose delivered versus the volume of tissue treated. FIG. 13b illustrates the dose delivered versus the upper and lower limit of expected radius of treatment for a 6 mm electrode in prostatic tissue. FIG. 13c illustrates the dose delivered versus the upper and lower limit of expected radius of treatment for a 12 mm electrode in prostatic tissue. FIG. 13d illustrates current applied versus dose response.

Generally, DC ablation creates necrosis around a singular anode and a singular cathode at a rate of approximately 0.07-0.05 cc/C at the anode and at a rate of approximately 0.10-0.08 cc/C at the cathode. A typical period for treating BPH using systems and methods for DC ablation as disclosed herein is under 30 minutes. Dosing at approximately 25 mA for approximately 30 minutes will deliver 45 C. This in turn treats between approximately 5.8 cc and approximately 7.7 cc of tissue per pair of electrodes. To achieve a more efficacious treatment, multiple electrode pairs may be used. In some embodiments, 2 to 6 pairs of electrodes may be used. This correlates to approximately 11.6 to approximately 14.4 cc of treated tissue for 2 pairs of electrodes and between approximately 34.8 and approximately 43.3 cc of treated tissue for 6 pairs of electrodes. These numbers do not account for the overlap of treatment zones which decrease the amount of treated tissue. In some embodiments, the treatment zones overlap. Treatment times may vary between 15 and 45 minutes depending on the dosing required and rate at which the treatment is delivered. Alternatively fewer pairs of electrodes could be used in a device to achieve these same larger treatment zones if the catheter or electrodes are repositioned between treatments.

The rate at which the charge is applied (current, units of milliamperes) does not affect the ultimate radius of the treatment zone as long as the current provides more charge than the tissue's natural ability to stabilize its own pH. The relationship between current applied and the dose response is shown FIG. 13d. As shown, in some embodiments, it may be desirable for the treatment current to be at or above approximately 1 mA. In the example of FIG. 13d, all currents above 5 mA exhibit generally the same dose response. While higher currents may not increase dose response, higher currents may reduce treatment time to deliver the desired dosage. The higher current, however, may increase likelihood of patient discomfort. Generally, as current decreases, patient discomfort and muscle contractions (or muscle twitch) decrease. In some embodiments, the dose may be delivered at a constant current to prevent nerves in the region of treatment from being stimulated and causing muscle contraction. The magnitude of current delivered may be adjusted during treatment to allow pain and treatment time to be minimized. Care should be taken however, because a fast rate of current change may cause patient discomfort and muscle twitch. Thus, in some embodiments, it may be advisable that any change in the current delivered be done at a rate no greater than 10 mA/s to prevent muscle contraction and patient discomfort. A suitable rate of change is approximately 1 mA/s.

Figure 14:
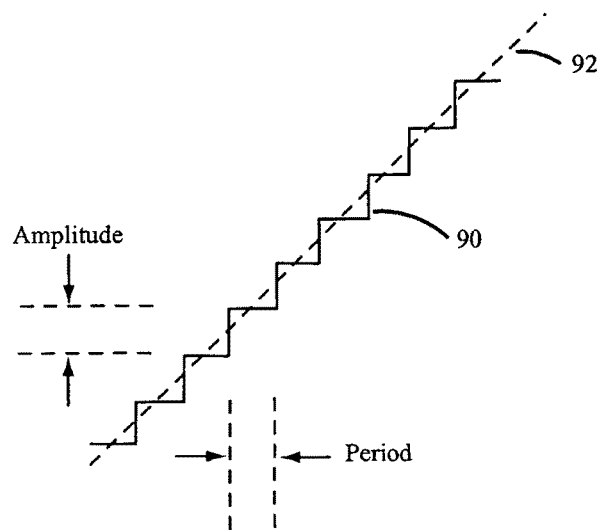
FIG. 14 illustrates and defines the period and amplitude of current ramping during the start of treatment, in accordance with one embodiment.

FIG. 14 illustrates current 90 increased gradually when current delivery is started to prevent the stimulation of nerves. Current 90 is also decreased gradually when current delivery is terminated. The increase or decrease may occur in steps of amplitude and period with the ramp rate equal to the step amplitude divided by the step period. The upper limit on the amplitude for preventing nerve stimulation is 0.5 mA for increasing current. A suitable embodiment is approximately 0.2 mA for increasing the current. The upper limit on the amplitude for preventing nerve stimulation is 1 mA for decreasing current. A suitable embodiment is approximately 0.5 mA for decreasing the current. Regardless of the slowness of the period of the steps, a large enough amplitude step will cause nerve stimulation. For amplitudes below that limit, there is a minimum limit on the period for preventing nerve stimulation. Small amplitude steps can still cause nerve stimulation if the steps occur too quickly and result in a ramp rate greater than 10 mA/s. The ramp rate (slope of broken line 92) should ideally be as great as possible without resulting in a high risk of nerve stimulation. If the step amplitudes are low enough, capacitance in the circuit may cause the output to look less like steps and more like a straight line (such as broken line 92), which may help to reduce the risk of nerve stimulation. These observations also apply to ramping down the current.

In some embodiments, an independent current source may be used to deliver the current for each electrode pair in order to control the charge passing through each electrode and thus the size of the treatment zone. Changing impedances at individual electrodes throughout the therapy session may lead to an unpredictable imbalance in treatment zones if multiple cathodes and anodes are put on a single current source. If multiple electrode pairs are placed on a single current source, the treatment zones may be controlled by putting a coulomb counter on each electrode and directing the desired amount of charge to each electrode.

The acidic and basic zones are created by the following chemical reaction:

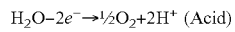  Anode Reactions:

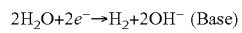  Cathode Reaction:

The anode reactions also include a chlorine reaction that produces molecular chlorine. The molecular chlorine reacts with water to form hypochlorous acid, chloride and hydrogen ions. These reactions occur within both benign and malignant tissue including prostate. A marker, such as an ultrasound marker, may be provided to indicate pH in real time during treatment.

The anode and cathode reactions create cell necrosis within the treatment zone. The cathode causes necrosis via a combination of liquefaction cell necrosis and coagulation cell necrosis. The anode causes necrosis via coagulation cell necrosis. Cell necrosis occurs in normal prostate tissue, hyperplastic prostate tissue, and malignant prostate tissue. Accordingly, dosage and configuration may be optimized to generally limit the treatment area to the hyperplastic prostate tissue.

Figure 15A:
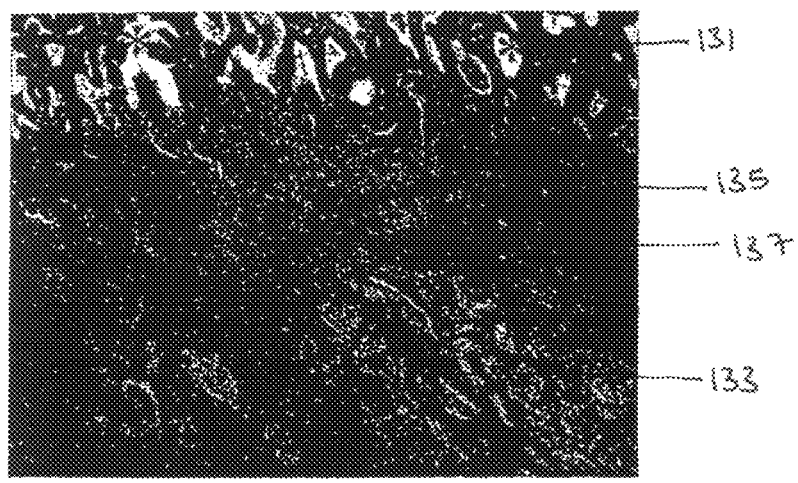
FIG. 15a is an in vivo image illustrating a liquefaction necrosis histology at the boundary of a cathode treatment zone.
Figure 15B:
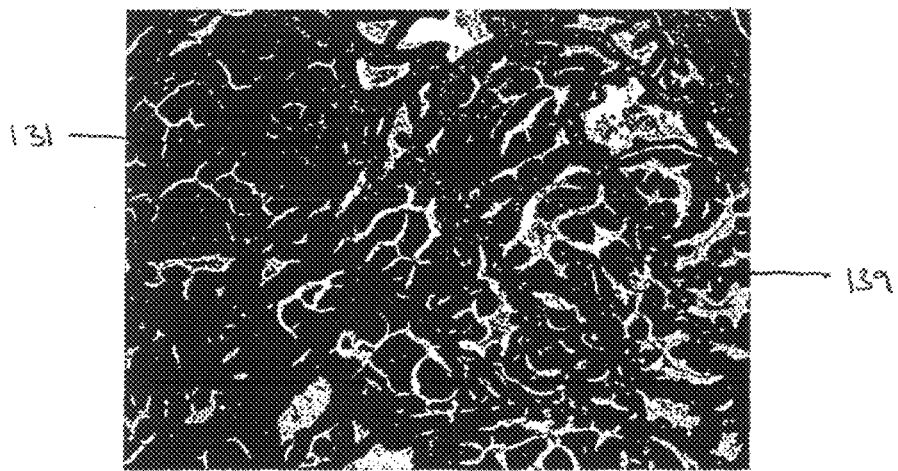
FIG. 15b is an in vivo image illustrating a coagulation necrosis histology at the boundary of an anode treatment zone.

FIGS. 15a and 15b illustrate images of necrosis within necrotic prostate tissue caused by DC ablation at a cathode and an anode. FIG. 15a illustrates liquefaction necrosis histology at the boundary of a cathode treatment zone. Normal tissue is shown at 131 and liquefaction necrosis is shown at 133. As shown, a transition zone exists at 135 with a liquefaction necrosis boundary 137 being formed. FIG. 15b illustrates coagulation necrosis histology at the boundary of an anode treatment zone. Specifically, normal tissue is shown at 131 and coagulation necrosis is shown at 139.

Liquefaction necrosis and coagulation necrosis create a change in the structure in the prostate as the affected tissues become fibrous and are absorbed into the body through its natural healing process. This thus causes removal of cellular mass, leaving a void. Because the treatment zone is predictable, the void is predictable. By removing cellular mass within the prostate, the interior of the prostate is debulked and excess pressure placed on the prostatic urethra is reduced. This reduction in pressure on the urethra reduces or eliminates BPH symptoms, sometimes referred to as Lower Urinary Tract Symptoms (LUTS). It is an advantage of DC ablation over other techniques that the outer wall of the prostate is more resistant to damage caused by the electrochemical reaction than is inner prostate tissue. Hence, a set of electrodes not perforating the outer wall but close to the wall destroys the desired prostate tissue inside the boundary formed by the wall and not the wall itself. The outer boundary generally appears to be more chemically robust as well as providing a mechanical boundary. Thus, while thermal energy does not respect the tissue plane, DC ablation does.

In some embodiments, the electrodes may be withdrawn, the catheter repositioned, and the electrodes redeployed to cover the desired treatment zones. In other embodiments, the number of electrodes provided is sufficient to provide treatment without redeployment of the system.

Once the reactions leading to cell necrosis have begun, the electrodes may be withdrawn and the catheter is withdrawn. In some embodiments, the electrodes are withdrawn into the catheter and the catheter is withdrawn. Withdrawing the electrodes into the catheter may comprise release of a trigger or slide in the handle, may comprise collapsing the electrodes by sliding a sheath over the electrodes, or may be done in other suitable manner. In some embodiments, the electrodes and the catheter are withdrawn simultaneously.

The liquefaction and softening of treated tissue around the cathode results at least from elevated pH; elevated pH causes necrosis and cell lysis. Rupture of the cell wall causes the rigid pathologic tissue to soften, relieving symptoms of BPH related to excess compression of the urethra. This effect can be employed to advantage in the removal of electrodes. Changing the polarization of each electrode to cathodic at some time during treatment will soften the area and allow easier removal of the electrode. Likewise, inserting the electrodes may be eased by making each one cathodic during the insertion. If tenting of the urethra is evident during insertion, causing each electrode to be cathodic at that time can soften the urethra at the electrode tip sufficiently to allow easier penetration without significant additional damage to the urethra For example, with some physiologies it may be difficult to penetrate lumens, such as the urethra, and tissue with a fine electrode. Chemical drilling may be used to aid in tissue penetration. More specifically, DC ablation may be used to help penetrate the tissue. In some embodiments, all of the electrodes may be negative or cathodic to aid in tissue penetration. This takes advantage of the inherent electroosmosis of DC ablation where fluids are drawn to the cathodes and the tissue becomes edemic. The gelatinous tissue so treated is more easily penetrated. Thus, in some embodiments, the electrode may be activated when first contacted with the tissue but before advancement into the tissue. The electrodes may be advanced during pre-treatment or pre-treatment may be done for a short period of time, for example approximately 30 seconds, and the electrodes then advanced.

Figure 16:
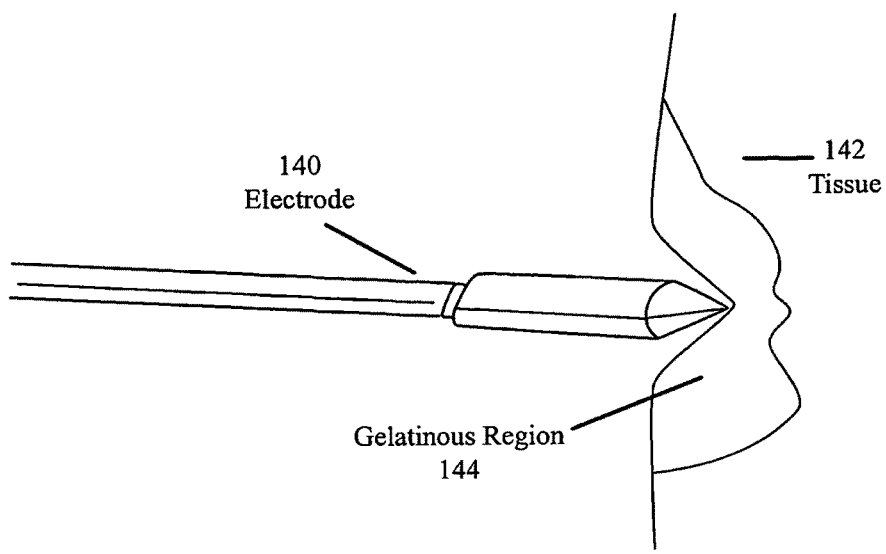
FIG. 16 illustrates a view of electrode deployment into pretreated tissue.

FIG. 16 illustrates a view of electrode deployment into pretreated tissue. As shown, the tissue 142 includes a pretreated region 144 that is substantially gelatinous. The electrode 140 is able to more easily penetrate the tissue 142 in the gelatinous region 144.

Figure 17A:
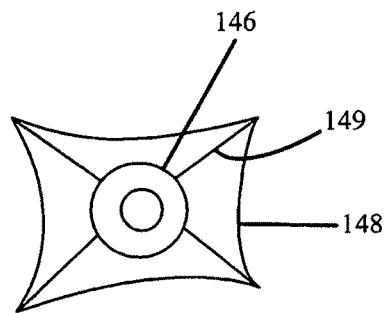
FIG. 17a illustrates a system for tissue treatment including a catheter and electrodes with the electrodes deployed without vacuum, in accordance with one embodiment.
Figure 17B:
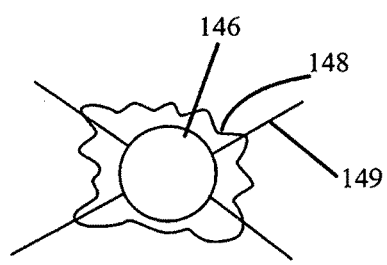
FIG. 17b illustrates a system for tissue treatment including a catheter and electrodes with the electrodes deployed with vacuum, in accordance with one embodiment.

FIGS. 17a and 17b illustrate a further embodiment to facilitate electrode penetration. In another embodiment of urethral preparation, a vacuum may be used to put the urethra in direct and firm contact with the catheter of a system for treating tissue as provided herein. Direct and firm contact of the urethra with the catheter facilitates piercing of the urethra by electrodes. With some physiologies, the urethra may have a larger cross section than the catheter placed therein. This increases column strength requirements for the catheter and makes it more difficult for the electrodes to pierce the catheter. For example, the urethra may expand and not be penetrated by the electrodes or the electrodes may buckle against the urethra. FIGS. 17a and 17b illustrate a system for tissue treatment including a catheter 146 and electrodes 149. The figures illustrate an end view with the system deployed through the urethra 148. FIG. 17a illustrates electrodes 149 deployed (without vacuum) and causing expansion of the urethra 148. As shown in FIG. 17b, by drawing the urethra 148 firmly against the catheter 146, for example by vacuum force, the electrodes 149 more easily penetrate the urethra 148. Thus, the electrodes 149 may be deployed relatively immediately after drawing of the urethra 148 against the catheter 146. FIG. 17b illustrates electrodes 149 penetrating the urethra 148, with the urethra 148 vacuumed to the catheter 146.

Figure 18:
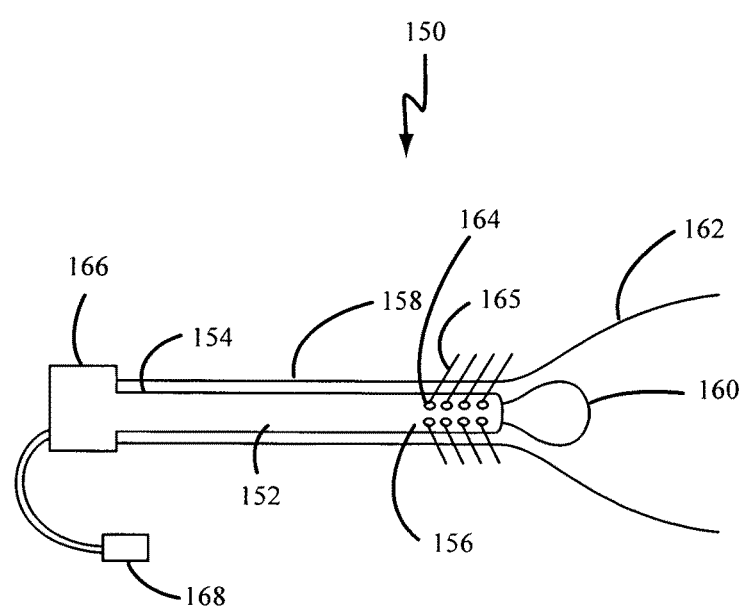
FIG. 18 illustrates an embodiment of a system for treating tissue including vacuum ports at the electrode holes, in accordance with one embodiment.

FIG. 18 illustrates an embodiment of a system for treating tissue including vacuum ports at the electrode holes. As shown, the system 150 includes a catheter 152 having a proximal end 154 and a distal end 156. As shown, the catheter 152 is configured to extend through the urethra 158. A balloon or other fixation element 160 is provided at the distal end 156 of the catheter 152 and is shown deployed in the bladder 162. A plurality of electrode holes 164 are provided at a distal portion, near the distal end 156, of the catheter 152. The electrode holes 164 operate for facilitating deployment of electrodes 165 from the catheter 152 and also operate as vacuum ports. A vacuum connector 166 and an electrical connector 168 are provided at the proximal end 154 of the catheter 152. The vacuum connector 166 may couple to a syringe or other means for achieving a vacuum. Drawing a vacuum before electrode penetration may facilitate use of smaller electrodes. In some embodiments, the system shown in FIG. 18 may be used for saline injection and vacuum. More specifically, the electrode holes/vacuum ports may be used to create a vacuum and also to distribute saline. Thus, in one embodiment, vacuum is achieved during penetration of the electrodes and is followed by saline injection for buffering during treatment.

As can be appreciated from the chemical reactions occurring at the electrodes, gases may be generated by DC ablation. More specifically, during DC ablation of soft tissue, ions are created at the anode and cathode electrodes when current passes through the electrodes. In order for the current to pass, the impedance generally is stable and less than about 5 k$\Omega$ to prevent operating at high voltages. DC ablation creates hydrogen and oxygen gas during the hydrolysis process. These gases can cause the impedance from the electrode to the tissue to spike greater than about 5 k$\Omega$. This happens when the gas is allowed to build up around the electrode without either diffusing into the tissue, being vented away from the treatment area, or going into solution in fluid around the treatment zone. Typical impedance ranges within the prostate are between approximately 300 and 500 ohms when treating with a current of greater than approximately 5 mA.

The amount of current delivered affects the amount of gas created. The rate at which gas is created is directly proportional to the current at which it is delivered. For soft tissue applications such as the prostate, DC ablation generally may be delivered between approximately 10 mA and approximately 50 mA. Generally, at currents higher than 50 mA, gas created by the treatment may not have sufficient time to dissolve, diffuse, or vent. 75 to 100 mA may be used to decrease treatment time if gas is able to sufficiently vent. Conversely, at currents lower than 10 mA, the body's buffering may reduce effectiveness of the treatment. In one embodiment, current level is between approximately 25 mA and 40 mA.

Generally, the amount of gas generated by treatment is determined by dosing. The amount of gas generated typically increases as current increases. In various embodiments, the system may be provided with mechanisms for venting the gases generated. Means for venting the gases may be provided within the electrodes, within the catheter, or other. Accordingly, the method for BPH treatment may further comprise venting gases created during treatment. Removal of the gases may lower the impedance and impedance fluctuations seen by the electrodes, thereby permitting continued treatment in the desired range of current and voltage.

Figure 19A:
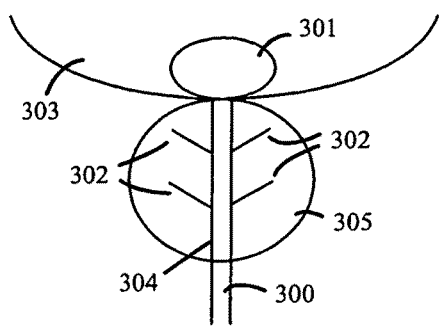
FIG. 19a illustrates balloon deployment in a bladder, in accordance with one embodiment.
Figure 19B:
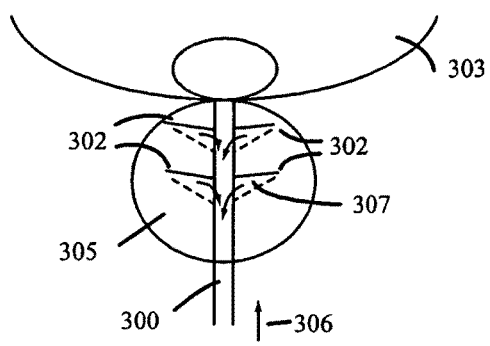
FIG. 19b illustrates catheter deployment while applying force towards a bladder, in accordance with one embodiment.
Figure 19C:
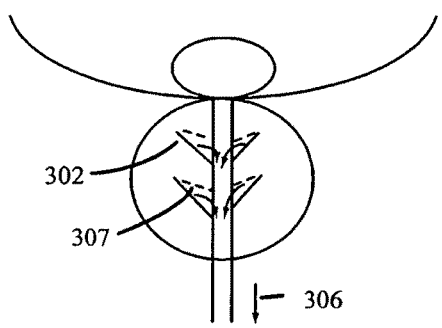
FIG. 19c illustrates catheter deployment while applying force away from the bladder in accordance with one embodiment.

A first embodiment of a mechanism for venting gases is shown in FIGS. 19a-19c. FIGS. 19a-19c illustrate relevant anatomy to BPH treatment including the bladder 303, urethra 304, and prostate 305. FIGS. 19a-19c further illustrate a catheter 300, balloon 301, electrodes 302, and gaps 307. As shown in FIG. 19a, the balloon 301 is located in the bladder 303 and inflated. The electrodes 302, having punctured the urethra 304, reside within prostate 305 either prior to or after applying current for DC ablation. In FIG. 19b, the catheter 300 has been pushed forward with force 306 towards the bladder 303 prior to applying current but after deploying electrodes 302. Force 306 holds the electrodes 302 in the position shown in FIG. 19b. This creates gaps 307 in the prostate 305 between the original electrode position of FIG. 19a and the new position of FIG. 19b. The gaps 307 serve to provide a path for the gases generated during DC ablation to escape. In an alternative embodiment, shown in FIG. 19c, the catheter 300 may be pulled away from the bladder 303 after deploying the electrodes 302.

Figure 20A:
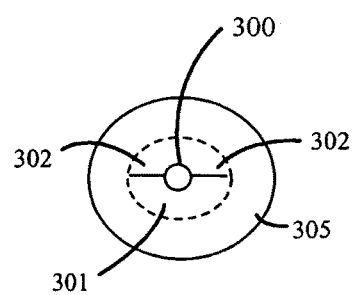
FIG. 20a illustrates electrode deployment in a prostate, in accordance with one embodiment.
Figure 20B:
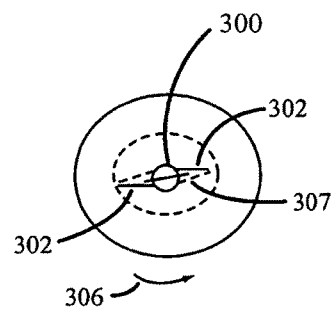
FIG. 20b illustrates catheter rotation for movement of electrodes, in accordance with one embodiment.

A second embodiment of a mechanism for venting gas is shown in FIGS. 20a and 20b. In yet another embodiment, the electrodes 302 may be rotated following deployment, as shown in FIGS. 20a and 20b. In FIG. 20a, electrodes 302 are shown deployed in prostate 305. The broken line represents the balloon 301. In FIG. 20b, the catheter 300 has been rotated by force 306, causing the electrodes 302 to assume a new position and opening up gaps 307 through which the gases may escape. In alternative embodiments, other means for removing gases may be used. For example, gas may be vented by having a negative pressure in the delivery system or catheter to effectively vacuum gas away from the active electrode(s).

Figure 21A:
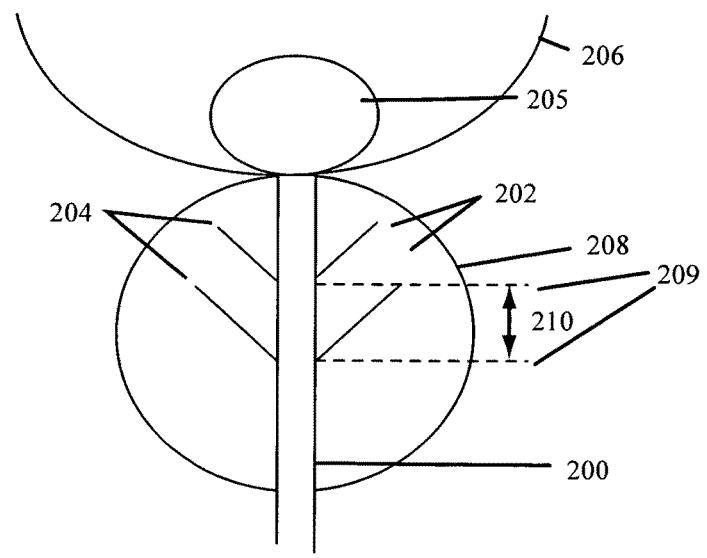
FIG. 21a illustrates a coronal view of a system comprising two axial planes of four electrodes each, in accordance with one embodiment.
Figure 21B:
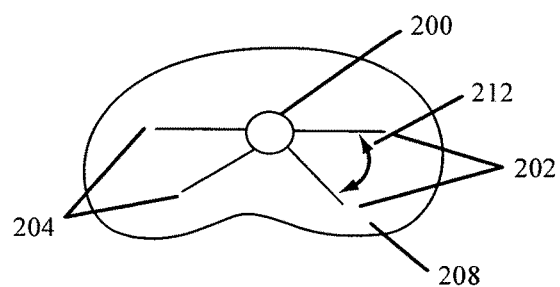
FIG. 21b illustrates a transverse view of a system comprising four electrodes in each axial plane, in accordance with one embodiment.

FIGS. 21a and 21b illustrate an embodiment comprising of two axial planes of four electrodes and illustrate the axial electrode spacing and angular separation. FIG. 21a is a coronal or top view and FIG. 21b is a transverse or end view. The system is shown including a catheter 200, a plurality of electrodes including two electrodes 202 on one side of the catheter 200 and two electrodes 204 on the other side of the catheter 200, and a fixation element 205. The catheter 200 is deployed transurethrally and the fixation element 205 positioned in the bladder 206 such that deployment of the electrodes 202 is into the prostate 208. As shown in FIG. 21a, an axial spacing 210, comprising the distance between the electrodes 202 or 204 on each side of the catheter 200, is provided between the electrodes 202 or 204. Dashed lines 209 indicate the longitudinal position of the electrodes 202 relative to the catheter 200. As shown in FIG. 21b, an angular spacing 212, comprising the distance between the electrodes 202 or 204 on each side of the catheter 200, is provided between the electrodes 202 or 204. The angular spacing is the angle between the posterior and anterior electrode on each side of the catheter.

Providing multiple electrodes to an area to be ablated can reduce the number of coulombs or the dose required from each electrode, thus decreasing the amount of gas created at each electrode. In some embodiments, no single electrode delivers more than approximately 72 coulombs. In one embodiment, each electrode delivers between approximately 24 and 48 coulombs of charge with an axial electrode spacing (measured down the catheter) of approximately 8 to 10 mm and an angular separation of between approximately 15 to 65 degrees. A suitable angular spacing is approximately 30 to 45 degrees with 35 degrees being optimal in certain embodiments. The axial spacing could be increased to 12 to 16 mm and up 20 mm if the dosing is increased. The axial separation could be reduced to 4 to 6 mm if dose per electrode is reduced and the number of electrodes is increased.

During treatment, the electrodes may lose ohmic contact with different types of tissues, thereby making it difficult to deliver the desired current. When contact is lost, it can cause the treatment zone to become more unpredictable and muscle contractions can occur due to spikes in voltage and current. Loss of contact may take place for multiple reasons including, at least:

1) Hydrogen gas created from the cathode reaction or oxygen gas from the anode reaction may saturate the electrode surface and cause an increase of impedance;

2) Chlorine gas created from the anode reaction may saturate electrode surface and cause an increase of impedance; and 3) The reaction at the anode may cause local dehydration and cause the tissue proximate to the electrode to lose its conductive properties.

In some embodiments, actions may be taken to prevent an increase in impedance or to counteract an increase in impedance arising at least from these sources. In one embodiment, a positive force may be added to the tissue using the active portion of the electrode, by the shape of the electrode design, or by using an array of electrodes and sequencing the therapy to allow natural diffusion within prostatic tissue to overcome the increase of impedance at the electrode site. Force to the electrode can be accomplished by adding a torque, an axial load down the electrode, or an axial load down the catheter.

Figure 22A:
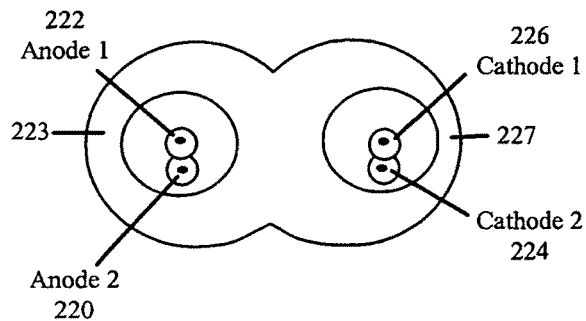
FIG. 22a illustrates two cathodes in parallel and two anodes in parallel and the associated treatment zones with moderate resistance, in accordance with one embodiment.
Figure 22B:
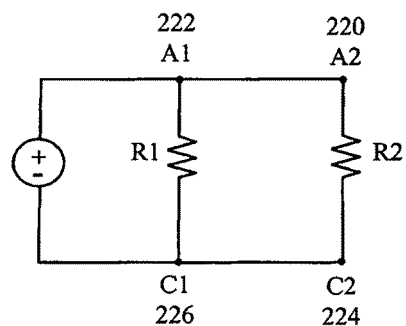
Figure 22C:
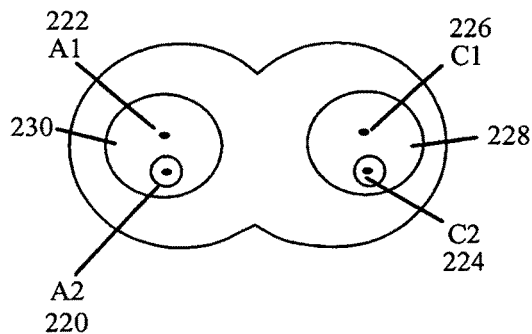
FIG. 22c illustrates treatment zones with high resistance, in accordance with one embodiment.

In another embodiment, an array of electrodes may be used including either or both of multiple cathodes and anodes in parallel with each other to deliver the therapy. For example, as shown in FIGS. 22a and 22c, multiple anodes and multiple cathodes may be provided in parallel. FIG. 22a illustrates a first anode 222, a second anode 220, a first cathode 226, and a second cathode 224. FIG. 22a further illustrates the treatment areas 223 and 227 associated with the anodes 222, 220 and the cathodes 226, 224, respectively. Generally, each electrode of an anode pair or cathode pair may be at approximately the same potential and be placed in close proximity. Providing electrodes in parallel and in close proximity can ensure continued treatment even if one electrode loses contact. More specifically, if one anode (or cathode) of an anode (or cathode) pair loses contact, the area will continue to be treated by the other anode (or cathode) in parallel. This is true whether the electrode pair is an anode pair or a cathode pair. FIG. 22a illustrates a pair of anodes 220 and 222 in parallel and a pair of cathodes 224 and 226 in parallel. FIG. 22b illustrates an electric current diagram for FIG. 22a. FIG. 22c illustrates the effective treatment areas 230 and 228 resulting from R1 and R2, respectively, of FIG. 22b. As shown, the effective treatment areas 230 and 228, or areas ablated, approximates the effective treatment areas 223 and 227 of FIG. 22a, where no impedance problems occur. While FIGS. 22a-22c illustrate two anodes and two cathodes, more than two electrodes may be put in parallel.

In one embodiment, the generator may be configured to monitor a measurement of impedance between the electrodes and uses a pattern of impedance measurements to predict a significant increase in impedance. Upon prediction of an increase in impedance, the generator reduces the current level or turns off the current, thereby preventing a current spike that could cause nerve stimulation.

Various current delivery mechanisms may be used to reduce the likelihood of stimulating nerves. In one embodiment, the generator utilizes a current source circuit with a high voltage compliance. Voltage compliance (or compliance voltage) is the maximum voltage a current source will go to in its attempt to source the programmed current. Compliance voltage values may be user settable, allowing user control over the sourcing and measurement process. If the generator voltage compliance is higher than the current level multiplied by the impedance, the current is controlled and current spikes are substantially prevented. For example, a voltage compliance of 200 V allows the current source to deliver a current of 20 mA without current spike due to an impedance change of 10 kΩ.

The likelihood of sudden impedance changes can be reduced by using low current, such as less than or equal to about 30 mA. The low current substantially prevents the gas generation rate from greatly exceeding the rate that the gas escapes from and/or diffuses into tissue.

In another embodiment, to reduce the likelihood of sudden impedance changes and to complete treatment in a relatively short time frame, treatment may be started with a relatively high current, for example approximately 50 mA, and the current level may be reduced one or more times during the treatment, for example to a level less than about 20 mA. At the start of treatment, using the high current level, gas is generated at a high rate. Before enough gas accumulates to cause the electrode to lose contact with the tissue, the gas generation rate is decreased, by reducing current level, to better balance the gas generation and gas escape/diffusion rates.

In yet another embodiment, a low level current (between approximately 1 mA and approximately 2 mA) can be applied for a short time (for example, less than about 5 minutes) before ramping up the current level. With the short delivery of a low level current, the area around the anode dehydrates and holds the anode in place. The forced contact between electrode and tissue may reduce impedance levels.

In a further embodiment, a low level current (between approximately 1 mA and approximately 2 mA) of opposite polarity from what will be used in the treatment may be applied for a short time (for example, less than about 5 minutes) before ramping up. The current may change the properties of the tissue around each electrode to reduce an impedance problem before ramping up the current.

Electrodes

In medical devices, electrodes are used to make electrical contact with body tissue. Depending upon the electrical source, the location of treatment, and the application of the treatment, the electrodes may be designed differently. The systems and methods for treating tissue described herein use direct current and this disclosure is thus limited to direct current applications. The location where this treatment may occur may be anywhere in the body. While the specific applications may vary, they generally all relate to DC ablation of tissue. DC ablation uses electrolysis to create necrosis of the tissue. Electrolysis uses two electrodes: an anode and a cathode. Multiple electrodes can be used in many different combinations and configurations to provide devices designed for different applications.

There are two theoretically extreme types of physiological electrodes, polarizing and non-polarizing. While never perfectly achievable in practice, both can be approximated.

In a theoretical non-polarizing electrode, current passes freely across the electrode-electrolyte interface without loss of energy. This can be nearly achieved with materials that readily oxidize and dissolve. One example useful in biological systems is a silver/silver chloride (Ag/AgCl) electrode. In such electrode, silver (Ag) is oxidized at the electrode surface into silver ions ($Ag^+$) and electrons ($e^-$) in solution at the interface. The silver ions react with chloride ions ($Cl^-$) and form silver chloride (AgCl) which precipitates on opposite silver electrode. In this example, silver is oxidized at one electrode while the other is plated by silver-chloride. Similar techniques may be used for electroplating in a process known as electrode position.

Ag/AgCl electrodes (non-polarizing) are nearly ideal in biological sensing or stimulating electrodes where the current is alternating. However, when using direct current stimulation, the silver (or other non-polarizing material) is readily oxidized and not replenished by alternating plating/oxidation and the material is consumed. Voltage overpotentials are minimal in non-polarizing electrodes; as the voltage is increased, current begins flowing at close to standard half-cell potentials.

In a theoretical perfectly polarizing electrode, no charge crosses the surface of the electrode. Current is transferred as a displacement current similar to a capacitor. The polarizing electrode is relatively inert to resist oxidation and dissolving. A platinum (or platinum-iridium) electrode is close to the ideal polarizing electrode. The platinum or platinum-iridium electrode sets up a large change in the concentration of ions at the electrode-electrolyte interface thereby causing a large voltage overpotential. This requires additional voltage prior to conducting current.

Platinum (or other polarizing material) must have perfect coverage on the electrode surface. Pinholes, cracks or other imperfections serve as sacrificial conductors due to their lower voltage overpotentials. In non structural regions of the electrodes, such as the tip, this may be acceptable. However, corrosion occurring in the middle of the electrode can cause a separation in the electrode. This issue is acute at the anode or positive electrode where the oxidation occurs. In contrast, the cathode or negative electrode is less susceptible to corrosion. Thus, in one embodiment of a system for tissue treatment using DC ablation, the electrodes are fixed to a given polarity with the anodes being platinum-iridium and the cathodes being a less expensive material such as stainless steel.

Figure 23:
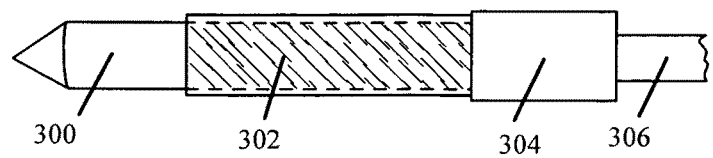
FIG. 23 illustrates a side view of an electrode assembly including an electrode, crimp tube, conductor wire, and insulation.

FIG. 23 illustrates one example of an electrode suitable for use with systems described herein. The electrode 300 of FIG. 23 is made up of a metal conductor material that is the interface between the electrical circuit and the tissue. A portion of the electrode may have insulation 302 covering a portion of it, limiting the amount of exposed electrode that is available for the reaction. The electrode 300 may have a tube 304 that is either crimped or welded to the electrode on one end and a conductor wire 306 on the other end.

Figure 24A:
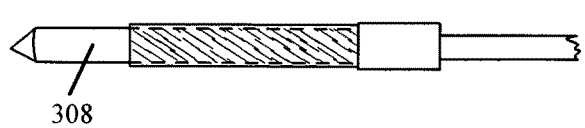
FIG. 24a illustrates a straight wire shaped electrode, in accordance with one embodiment.
Figure 24B:
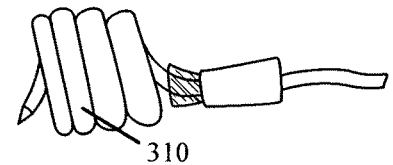
FIG. 24b illustrates a coil shaped electrode, in accordance with one embodiment.
Figure 24C:
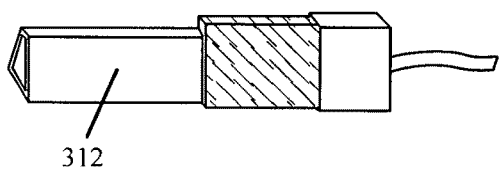
FIG. 24c illustrates a blade shaped electrode, in accordance with one embodiment.
Figure 24D:
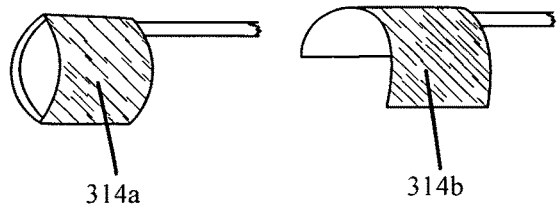
FIG. 24d illustrates a ring and partial ring shaped electrode, in accordance with one embodiment.
Figure 24E:
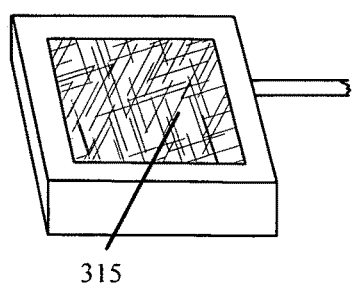
FIG. 24e illustrates a wire mesh shaped electrode, in accordance with one embodiment.

Depending upon the application and the location of the treatment, the electrodes may have different shapes and configurations. FIGS. 24a-24e show different shapes of electrodes. FIG. 24a illustrates a straight wire electrode 308. FIG. 24b illustrates a coil electrode 310. FIG. 24c illustrates a blade electrode 312. FIG. 24d illustrates a ring electrode 314a and a partial ring electrode 314b. FIG. 24e illustrates a wire mesh electrode 315.

As shown in FIG. 24a, straight wire is one shape for an electrode. A wire electrode 308 can be basic platinum or stainless steel wire. Such electrode may be easily inserted into tissue if it has a small diameter and/or a sharpened end. The wire may be permanently attached to a catheter in a fixed location, or may move within channels inside the catheter. The wire may alternatively be formed into a coil or mesh electrode.

As shown in FIG. 24b, a coil is another shape for an electrode. A coil electrode 310 may be screwed into tissue or may be mounted on a device that can be inserted into the tissue. Such device may be a catheter with one or more multiple coil electrodes mounted thereon. The coil electrodes 310 can be made of the same materials as the wire anodes and cathodes described with respect to FIG. 24a. The coils can be made of long sections of electrode wire. The wire can range from 0.12 mm to 0.5 mm in diameter depending on how tightly wound the coil is. The length and diameter of the electrode wire and spacing between the winds of the coil generally determine the shape of the treatment zone created by the electrode.

As shown in FIG. 24c, a blade 312 is another shape for an electrode. It represents many different shapes of material that can be used that are not round. The shapes may be oval or rectangular (as shown) or other shapes that better fit the application requirements than a round wire. These requirements may include greater conductivity, greater strength, better flex fatigue, or it may fit into the design better or give better bending characteristics.

As shown in FIG. 24d, a ring is another shape for an electrode. Generally, a ring electrode may be similar to a tightly wound coil electrode. A ring electrode 314a or a partial ring electrode 314b may be made from thin material and formed into a ring or made from a flat part and welded into a ring. Ring electrodes can be placed over other structures such as a catheter body to control the electrode position. In a similar way, a portion of a ring can be used to direct the current in a particular direction instead of 360 degrees around the catheter body.

FIG. 24e shows another type of electrode shape. It is made of woven uninsulated wire to form a wire mesh 315. This mesh allows the electrode to make contact with a large, relatively flat, surface. Because the mesh is made of wire instead of solid material, the mesh has greater flexibility, better flex fatigue, and is less expensive than solid sheets of the same material.

Figure 25:
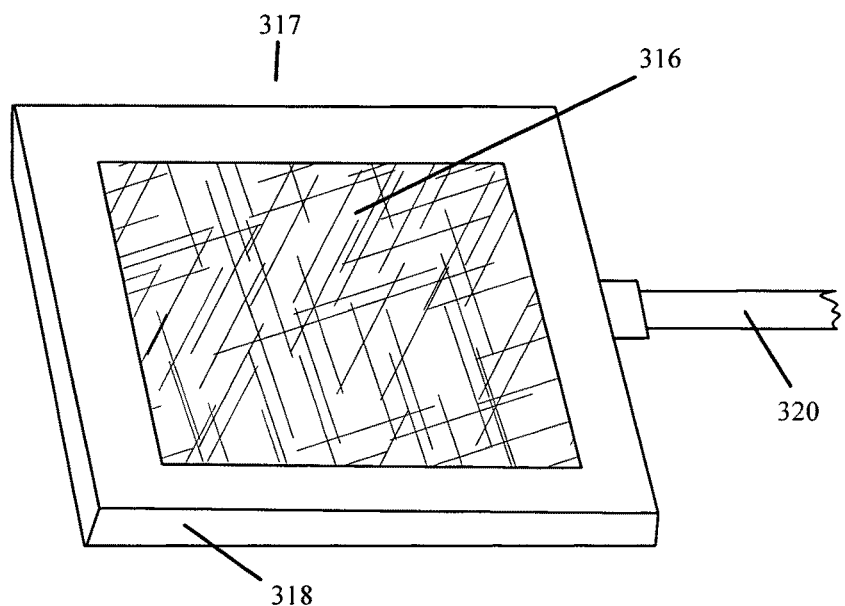
FIG. 25 illustrates the details of a wire mesh shaped electrode, in accordance with one embodiment.

FIG. 25 illustrates a detailed view of a wire mesh electrode. As shown, the wire mesh electrode is a fixed electrode that can be used on the tissue surface. The wire mesh electrode 317 may be formed as a large surface electrode that spreads the treatment over a large surface area so that tissue damage is on the surface of the tissue and does not penetrate deep into the tissue. In the embodiment shown, the electrode 317 is a woven mesh of un-insulated wires 316, with an insulating coating on the side of the mesh away from the tissue 318. An electrical connection 320 is made to the wire mesh. A cathodic electrode may comprise a stainless steel or titanium wire mesh while an anodic electrode may comprise a platinum or platinum coated wire mesh.

An alternative cathodic wire mesh electrode may comprise a silver-chloride electrode. This type of electrode typically does not treat the tissue. The silver chloride reaction takes place at the tissue instead of forming the hydroxide ions normally formed at the ablation cathode.

Figure 26:
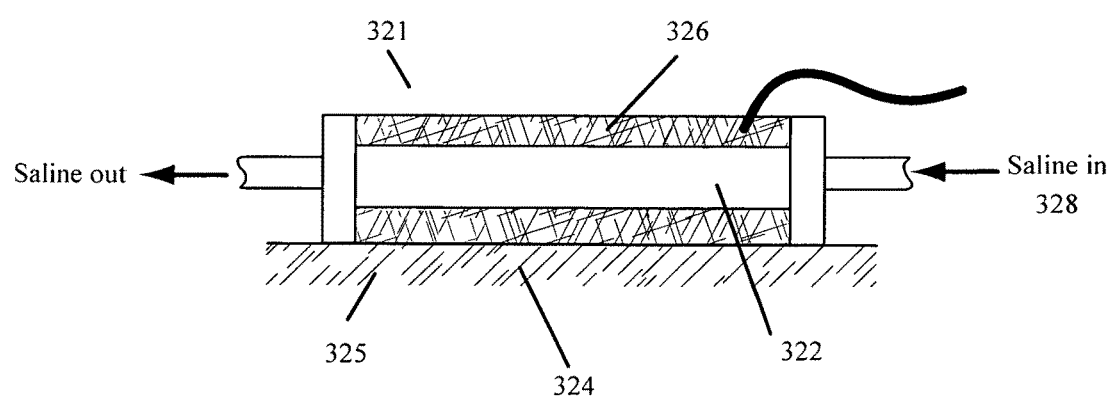
FIG. 26 illustrates an alternative anodic wire mesh shaped electrode, in accordance with one embodiment.

FIG. 26 illustrates an alternative anodic wire mesh electrode 321. As shown, the wire mesh electrode 321 includes two wire mesh layers 324, 326 with a chamber 322 between layers. The first wire mesh layer 324 may be placed on the skin 325. The chamber may be configured to be capable of having saline 328 flow through it, allowing the anodic reaction to take place in the chamber and not at the skin. The saline solution acts to dilute and wash away the acid produced by the anodic reaction in the chamber.

Various electrode configurations are suitable for use with a DC ablation system and method as discussed herein. The electrodes may comprise different materials, different configurations, and have different coatings. The electrodes may be provided singly, in pairs, or other.

In some embodiments, the electrodes may comprise Nitinol clad with platinum, or a Nitinol wire encased in a platinum tube. Platinum has a natural resistance to material decomposition during the transfer of energy. Platinum does not react with chemicals found naturally in the body or generated during electrolysis. Platinum is relatively soft, and a low amount of force can permanently deform or break items manufactured of platinum. Materials having similar properties and suitable for uses as described herein with respect to platinum include, for example, Rhodium, Palladium, Iridium, and Platinum Iridium.

Nitinol is a nickel, titanium, metal alloy. Nitinol is generally either superelastic or shape memory. Shape memory material can be deformed at room temperature but, when the temperature is elevated above its activation temperature, it returns to its preformed configuration. Superelastic material has a transition temperature below room temperature such that, at room temperature or above, it stays in a normal, preformed configuration (such as straight).

For use with the systems of treating tissue discussed herein, the electrodes may be configured to have a high resistance to material decomposition when electrons are transferred and also to have a high resistance to bending stress. Accordingly, a material with high resistance to deformation, such as Nitinol, may be coated with a material with high resistance to material decomposition, such as platinum.

Figure 27:
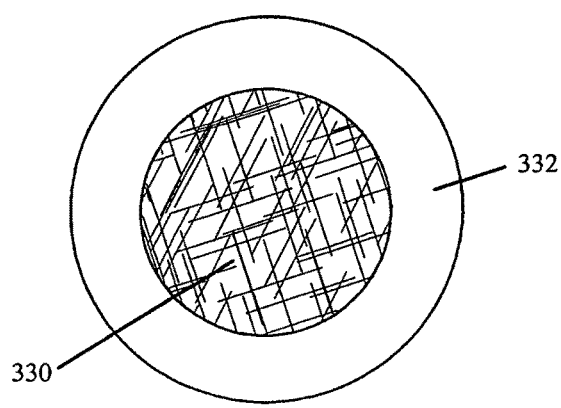
FIG. 27 illustrates a cross section of an electrode having an inner core and an outer shell, in accordance with one embodiment.

FIG. 27 illustrates a cross section of an electrode having an inner core 330 and an outer shell or coating 332. The inner core 330 may be, for example, superelastic Nitinol. The outer shell 332 may be, for example, platinum. The combination provides a corrosion resistant, superelastic wire that is useful for electrodes whose shape retention is desirable. In various embodiments, the electrodes may have a diameter between 0.25 mm and 0.5 mm. Such diameter is sufficient for puncturing tissue but retains flexibility for retraction of the electrode after treatment.

A Nitinol wire metal may withstand by-products of tissue treatment as provided herein when used as a cathode. Further configuration of the Nitinol wire may be done to enhance its suitability for withstanding by-products of tissue treatment when used as an anode. For example, a Nitinol wire may be configured to withstand by-products of tissue treatment by the addition of a corrosion resistant coating.

As mentioned, DC ablation is an electrolysis process. The electrolysis process, as well as the acid, base, and chloride ions that are produced by the electrolysis, require the electrode materials to be able to withstand a very corrosive environment. Many different coatings and coating techniques were examined and tested for the ability to stand up to the electrolysis process used in the DC ablation process. Platinum and Platinum Iridium are perfect electrode materials, but do not retain their original shape when bent and the material flex fatigues after only a few cycles. Stainless steel had the strength to stand up to the bending and flexing required by the design, but it retained a permanent set when used in the design. Stainless steel would work for only a short time (10 minutes) before dissolving as an anode. As a cathode, stainless steel would be acceptable for a few hours. Nitinol is a material that will maintain its original preset condition (bent, straight, etc.) under extreme bending conditions. Nitinol would last longer than the stainless steel as a cathode, but would also dissolve after 10 to 15 minutes as an anode. As a cathode, Nitinol would also be acceptable for several hours of use. It was determined that a suitable combination of material for an anode or cathode is Nitinol with a platinum coating. Such combination provides the mechanical characteristic and the chemical resistance to electrolysis.

While combination electrodes are discussed herein, in one embodiment an electrode may be used without the electrolysis resistant coating. In accordance with such embodiment, the anodic electrodes dissolve in the body during the electrolysis process and thus need not be removed after treatment.

Returning to combination (or composite) electrodes, there are different ways to coat materials with platinum. Electrolytic coating uses an electrolytic process to coat platinum on the surface of the metal. The parts are placed in a tank and a current is passed between the parts and the solution of ions of material to be coated. Nickel and platinum electrolytic coatings were attempted. This process did not give consistent coatings in thin layers, and testing showed that the coating did not adhere well during flexing. The material had pin-holes that allowed corrosion to take place through the coating. Another method, vapor deposition, is a process capable of coating materials with thin and consistent coatings. In this process, the parts to be coated were placed in a vacuum chamber, and material to be coated was ionized. The materials in the chamber are coated with the ionized vapor. Platinum and Titanium Nitride were tested. Other possible coatings are Iridium, Rhodium, crystalline and amorphous carbon, and Iridium Oxide. The Platinum and Titanium Nitride coatings did not adhere strong enough to the wire to withstand the bending and abrasion required of the electrodes. They also did not perform well in the corrosion testing where pin holes caused anodic electrode failures due to the dissolving of the core material (similar to the other coatings). These coatings would have prevented corrosion better in thicker coatings, but thicker coatings tend to not stick to the surface or core as well as thinner coatings. Thicker coatings also start to take over the composite material properties (causing stress cracks from flex fatigue, and greater permanent set).

To get a strong, thin, pin-hole free coating, a continuous tube of conducting metal can be applied over the core Nitinol wire. Two methods to achieve this are Drawn-Filled-Tube (DFT) and Cladding. Both of these processes start out with an ingot of the center core material surrounded by a tube of outer material. In the Drawn-Filled-Tube method, a tube of the outer material is placed over the core material. In the cladding process, thin sheets of the outer tube material are wrapped on the center core until the desired outer tube thickness is achieved. In both cases, once the composite ingot is made, it is drawn down to the correct diameter in successive steps with heat treatment cycles between the steps. In one embodiment a core of Nitinol is used with an outer tube of platinum or platinum iridium. The drawing steps and heat treatment cycles may be optimized to maintain the material properties of the Nitinol, such that the platinum adheres to the core Nitinol.

In one embodiment, a Nitinol core is used with a 100% Platinum coating, with a core to coating cross-sectional area ratio of 90/10%. During the processing two material layers (center Nitinol core and outer platinum tube) separated. When the coating had 10% iridium added (90/10% PtIr), the coating became harder and better matched to the core Nitinol. At the same time, a thicker coating, with a core to coating cross sectional area of 80/20%, was created. The resulting wire outside diameter was 0.28 mm with the outside coating thickness of 0.0127 mm. The composite wire had Ultimate Tensile strength of 1100 to 1500 MPa, a Permanent Set of 0 to 1% Strain, and a Modulus of Elasticity of 55 to 75 GPa. In order to insert the wire into tissue, the wire needs to have minimum buckle strength. Buckle strength is largely determined by the material cross-section (including diameter), Modulus of Elasticity, and unsupported length. This electrode wire did not have a large enough buckle strength to insert the electrode into the tissue. A larger diameter was required. Wire diameters of 0.33 and 0.46 mm were made with the 90/10% Platinum Iridium outer tube and a core to coating cross-sectional area ratio of 85/15%. The 0.33 mm diameter material was on the border of being able to penetrate tissue. The 0.46 mm diameter material penetrated tissue with ease when sharpened. The new 0.46 mm diameter material had some variations in material properties. Those with a Permanent Set of higher than 1% strain had too low of a buckle strength to be used in the design. The material was required to have a Permanent Set of less than 1% strain.

A suitable embodiment includes a coating composition of platinum with 5 to 20% iridium added and Nitinol core with an 80 to 85% core cross sectional area. Improvements in annealing and drawing capabilities may allow pure platinum and increase the core cross-sectional area to 90%. In one embodiment the composite electrode material may contain a minimum of 40% cold work to maximize buckling strength. In another embodiment, the cold work may be reduced to 30-35% in order to minimize flex fatigue. Generally, the exact composition is a compromise between needs for buckling strength and needs for flex fatigue. Thus, the composite electrode may be varied for different applications with differing needs.

Other variations in electrode diameter and length will work for various electrode designs. In one embodiment, an electrode may be 0.46 mm in diameter, 6 mm exposed electrode length, and 32 mm unsupported length. The exposed length may be between 3 and 12 mm. The 0.46 mm diameter electrodes have been used up to 40 mm long. Smaller electrode diameters (0.38, 0.41, and 0.43 mm) may be used in with shorter unsupported lengths in this design. The electrode diameter may be between 0.25 and 1 mm. The unsupported electrode length vs. electrode diameter is design dependent. It is to be appreciated that these dimensions are exemplary of a specific embodiment and are not intended to be limiting.

In one embodiment material specifications for the electrodes are as follows.

Material Core to Coating Cross-sectional Area Ratio: 90/10% core to outer coating to 70/30% core to outer coating
PtIr Coating: 95/5% PtIr to 70/30%
Cold Work: 30 to 45%
Ultimate Tensile Strength: 1100 to 1500 MPa
Permanent Set: Less than 1% Strain
E=55 to 75 GPa (reference only)

The greater the percentage of cross sectional area taken by the outer shell or coating, the more the composite material takes on the characteristics of the outer shell or coating. Where the outer shell is used only to protect the inner core and the characteristics of the inner material, or a high resistance to bending stress, are desirable, the percentages of the inner core and the outer shell may be balanced accordingly. In some embodiments, it may be desirable to make the outer shell coating as thick as possible with minimal effects on the mechanical characteristics of the composite. For example, the outer shell may be from 5 to 50% of the diameter (thickness from 0.01 to 0.25 mm). The outer coating may be adjusted by changing the percentage of cross-sectional area, or by keeping that constant, changing the outer diameter of the composite wire. Coating thickness may generally be between 5 and 50% of the electrode diameter (0.01 to 0.25 mm coating thickness).

In one embodiment, the electrodes may comprise a superelastic Nitinol wire encased in a platinum/iridium tube. Superelastic Nitinol wire can experience a strain of approximately 8% before permanent deformation occurs. The following equation thus can be used to determine a safe relative size of the electrode diameter for a minimum bend radius:

$$\text{Strain} = (\text{wire radius}/(\text{wire radius} + \text{bend radius}))$$

$$8\% \ (\text{wire radius} + \text{bend radius}) = \text{wire radius}$$

0.08 bend radius=(1−0.08)×wire radius

Bend radius=(0.92/0.08)×wire radius

Bend radius=11.5×wire radius

Thus, in one embodiment, a 0.3 mm diameter electrode wire may use a minimum bend diameter of approximately 11.5×0.3 mm or approximately 3.2 mm. A bend diameter smaller than this will cause permanent deformation. In another embodiment, a 0.46 mm diameter electrode wire may use a minimum bend diameter of approximately 11.5×0.46 mm or approximately 5.3 mm.

The amount of curvature left in a wire after it has been wrapped around a mandrel is relative to the modulus of the core material, the ultimate strength of the outer tube of material, and the radius of each. Pure platinum has the lowest material ultimate strength, giving the largest residual bending radius of curvature. The following equation can be used to determine residual wire bending radius of curvature.

Residual Wire Bending Radius of Curvature $$=((E_c)(r)(r_i^4))-((r_i)(\text{UTS})(r^4-r_i^4)/((\text{UTS})(r^4-r_i^4))$$

Where:
$E_c$=core (Nitinol) modulus=55 GPa
r=outer radius of the composite=0.14 mm (0.3 mm diameter)
$r_i$=core radius=0.133 mm (0.265 mm diameter if 90% cross-sectional area)
UTS=ultimate strength of outer tube=172 MPa (platinum)

Using these predictions and methods, a wire resistant to corrosion during passive and active electrolysis and having wire elastic characteristics of Nitinol may be provided. The wire is relatively straight after being wrapped around a small mandrel.

In one embodiment, the electrode may comprise a 0.3 mm diameter wire with a 90% (by volume) Nitinol core. In another embodiment, the electrode may comprise a 0.3 mm diameter wire with an 80% (by volume) Nitinol core and an outer material of 90/10% Pt/Ir. The outer material wall is approximately 0.016 mm thick. In this embodiment, the residual bending radius of curvature is approximately 38 mm.

Figure 28:
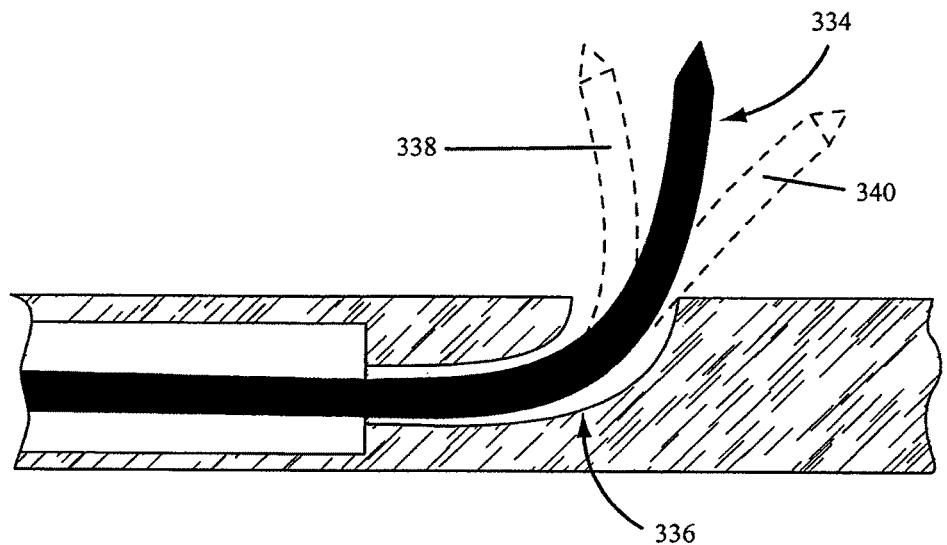
FIG. 28 illustrates variation seen in the extension of a straight electrode based on the thickness of an outer coating on the electrode, in accordance with one embodiment.

The coating thickness can also affect another characteristic of the straight moving electrode. FIG. 28 illustrates a straight electrode 334 and possible exit paths from a cavity 336 in tissue. As shown, the cavity 336 follows a curved path. The electrode exit path may curl more 338 or less 340 depending upon the thickness of the outer coating. When pure platinum wire is used it curls more than when straight Nitinol is used. The thickness of the outer sheath of platinum will determine whether it acts more like platinum or Nitinol.

In accordance with further embodiments, the electrode wires may be insulated to control the shape of the treatment zone and to protect the exposed wire end. Insulation may be used to facilitate electrode penetration of tissue without treating that tissue. The insulation generally is flexible and tough, and capable of adhering to the electrode so that it can be pulled inside the catheter and pushed back out without removing the insulation. One suitable insulating material is thin walled polyimide tubing adhered to the electrode with adhesive. Another insulating material is Parylene, a vapor deposited coating. Other materials that may be used to insulate the electrode include tubes of polyethylene, PTFE, silicone, PEEK, or insert molded thermoplastic such as polycarbonate or ABS.

Insulation material may be placed on electrodes to limit where the active area of the electrode is located. The insulation material may be PTFE, Polyimide, ETFE, Parylene, or other similar insulation materials. The material may generally be fixed in place. Generally, the insulation material is designed to remain in place through abrasion caused by the movement of the electrode. The base electrode material, the thickness of the insulation material, and the type and amount of abrasion will affect the ability of the insulation to stay in place. Some materials like Parylene are vapor coated in place, with the exposed areas of the electrodes masked off. This process can produce good results unless the masking is not accurately done or the material does not stick to the base electrode material. Some materials like PTFE and ETFE are more difficult to bond to the electrode surface for the same reasons they are chemically inert. Some materials like Polyimide are very tough even in thin cross sections (0.05 to 0.08 mm wall thickness), and can be easily bonded to the electrode surfaces. In various embodiments, wall thicknesses for the insulation may be between 0.02 and 0.13 mm. Another method of fixing the end of the insulation in place is through the use of a crimp tube that overlaps the insulation and is crimped down onto the insulation, trapping the end between the crimp tube and the electrode. A combination of these methods can also be used in which the tube is bonded in place with adhesive and then the end is crimped in place.

Figure 29:
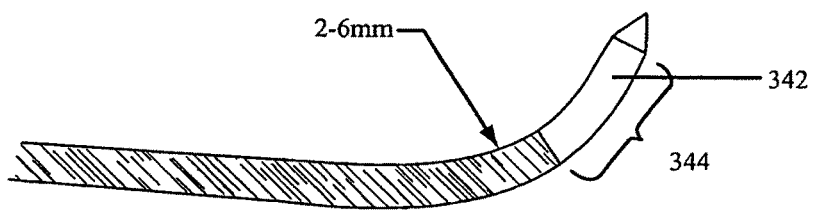
FIG. 29 illustrates a curved wire electrode with insulation, in accordance with one embodiment.
Figure 30:
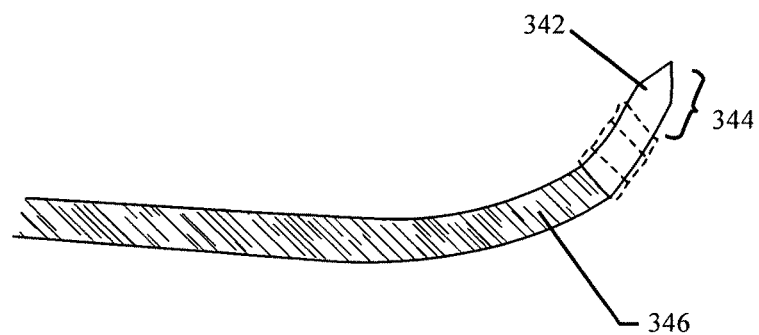
FIG. 30 illustrates a straight wire electrode with insulation, in accordance with one embodiment.

FIGS. 29 and 30 illustrate a needle electrode 342 having an un-insulated portion tip 344. Specifically, an electrode having the form of a straight or curved needle, with a bend radius of 2-6 mm may be coated in part with an insulator (alternatively, as previously described, the needle electrode may be coated in whole with an insulator). Thus, a portion 344 of the electrode 342 is un-insulated. In the embodiments shown, the un-insulated portion 344 is at the tip. The un-insulated portion 344 may be provided at a given length to optimize treatment. The desired length may vary depending on treatment area, on patient physiology, or on other factors. In some embodiments, as shown in FIG. 30, an electrode is provided having an insulated portion 346 and an un-insulated portion 344 wherein the un-insulated portion 344 may be adjusted to create a custom length of un-insulated portion 344. Such adjustment may be done via a thermal or chemical wire stripping tool or a laser. A suitable tool is provided by Coast Cable Tools and will thermally strip insulation from solid wires of size #14 to #30 AWG. Other tools may alternatively be used.

Figure 31:
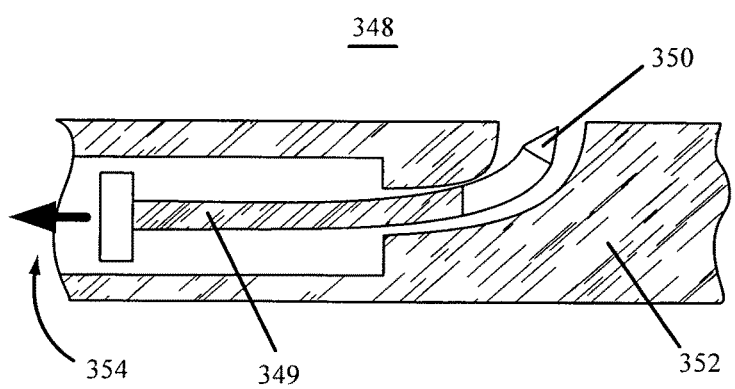
FIG. 31 illustrates a deployed straight wire electrode with a sharpened tip, in accordance with one embodiment.
Figure 32:
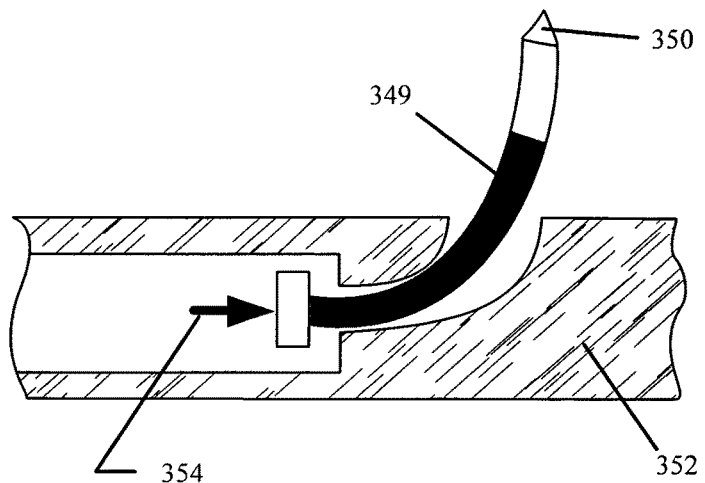
FIG. 32 illustrates a retracted straight wire electrode with a sharpened tip, in accordance with one embodiment.

FIGS. 31 and 32 illustrate a system 348 including an electrode 349 having a sharpened tip 350. As shown, the system includes a catheter 352 with an electrode deployment mechanism 354 provided therein. FIG. 31 illustrates the system 348 with the electrode 349 retracted. FIG. 32 illustrates the system 348 with the electrode 349 deployed. The electrode 349 may include insulation over its length with an exposed metal section at the tip 350.

In some embodiments, the tip of the electrodes may be configured for different angles of insertion. Routing through different channels in a polymer steering tip of a catheter provides a different angle of insertion into tissue for DC ablation electrodes. Further, tip sharpness of the electrodes may be increased to facilitate penetration. Generally, the distal 0.5 to 1.5 mm may be sharpened to enhance penetration. Increasing the angle of insertion of the electrode to approach approximately 90 degrees from parallel with the urethra increases the percentage of reliable insertion by approximately 10 percent for every 10 degree of angle change, representing an increase in angle from parallel. Further, reducing the surface area of the electrode tip by approximately 50 to 75% reduces the force required for tissue penetration by approximately 50 to 75% for a given electrode diameter and angle. Thus, for example, starting with an electrode diameter of approximately 0.25 to approximately 0.5 mm, the insertion force drops from about 800 to 1000 g for an electrode with a square and perpendicular end to about 300 to 400 g for an electrode with angular cuts to sharpen the end of the electrode.

Placement of the electrodes at treatment locations is done by penetrating tissue with the electrodes. The tissue may be difficult to penetrate and so the electrodes may be further configured with a device to facilitate puncture and penetration. Specifically, in one embodiment, fixed electrodes may be mounted to a device that has a feature that punctures the skin or tissue. There may be a removable structure that penetrates the tissue and then is retracted once the fixed electrode is in place.

Electrodes that move may be configured with an integral feature for puncturing the tissue so that the electrode can be moved into treatment position. Electrodes may move through channels in a device to extend out of the device and retract into the device after treatment. These devices may be provided with features that enhance maneuverability and substantially prevent them from getting stuck on corners and features that facilitate either the extension or retraction of the electrodes. Depending upon the configuration of the electrodes and the device, the ability to penetrate tissue and the ability to maneuver may be in direct opposition (a round electrode end may not penetrate tissue and a sharp electrode end may get stuck inside the device).

A suitable puncturing feature for a moving electrode is a sharp pointed end on the insertion end of the electrode. Such feature may be increasingly desirable as the diameter of the electrode increases. A 0.25 mm diameter electrode may use a flat or round insertion end instead of a sharp insertion end with acceptable puncture force. In contrast, the insertion force of a 0.5 mm diameter electrode is significantly improved with a sharp puncture feature on its insertion end.

Figure 33:
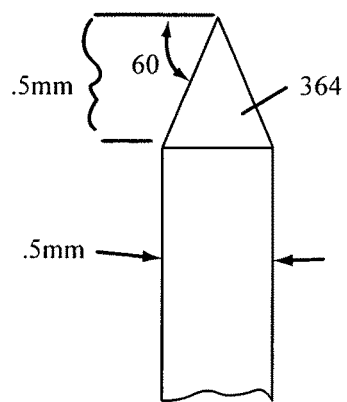
FIG. 33 illustrates a straight wire electrode with a cone shaped, sharpened tip, in accordance with one embodiment.
Figure 34A:
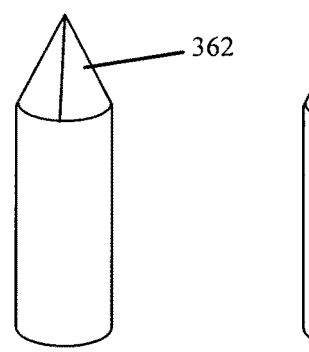
FIG. 34a illustrates a straight wire electrode with a faceted shaped, sharpened tip, in accordance with one embodiment.
Figure 34B:
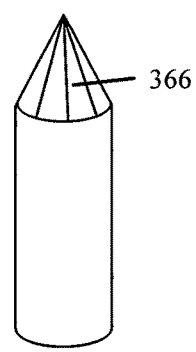
FIG. 34b illustrates a straight wire electrode with a multi-faceted shaped, sharpened tip, in accordance with one embodiment.

FIGS. 33, 34a and 34b illustrate electrodes with sharpened insertion ends as puncturing features. FIG. 33 illustrates a conic shaped end 364. FIGS. 34a and 34b illustrate a faceted shape end 362, 366 respectively. In alternative embodiments, the puncturing feature may be a combination of conic shape and a faceted shape or may have other suitable configuration. A variation in the conic feature is the angle and length of the conic feature. A 60 degree angle on a 0.5 mm long conic feature is suitable, for example, with a 0.5 mm diameter wire. Any angle between 45 and 85 degrees may be used as long as the flat on the top of the pointed end is small. A faceted feature may have two, three, or more facets. Facets at a 60 degree angle and of 0.5 mm length are suitable with a 0.5 mm diameter wire. The number of facets greater than two and an angle between 45 and 85 degrees may be used. The more facets, the more the puncturing feature approximates a conic feature. The lower the angle, the shorter the facet and the greater the insertion force. The opposite is true for a higher angle.

FIG. 35a illustrates a round 368 insertion end and FIG. 35b illustrates a flat insertion at end 370. Rounder flat insertion ends can be used for preventing moving electrodes from sticking on surfaces as they are extended or retracted through a curved channel. The specific configuration for maneuverability depends upon the channels and electrode. Rounded ends are generally suited for maneuvering 45 degree angles on the cone while facets on the end of the electrode help prevent sticking during extension and retraction. In some cases the angle or radius of the channel that the electrode must follow determines the radius or angle of the facet on the end of the electrode. Another alternative is to turn one of the facets into a radiused side. If the radiused side is oriented toward the angle or radius of the channel, it can prevent the sticking of the electrode as it is extended, but yet not significantly increase the insertion force of the electrode.

These features can be put on the end of the electrodes using a grinding operation (manual or automatic), or an Electro Discharge Machine (EDM). If the features are oriented on the electrode, automation of the process facilitates repeatability of the process.

A proper orientation of electrodes relative a device may enhance utilization of features of the electrodes, especially in the case of moving pin electrodes. An example of this is a moving pin electrode with a radius on one of the sharpened facets on the end of the electrode. Such electrode may be aligned with the outside radius of a channel that the tip of the electrode is to follow during electrode insertion. If the electrode is aligned, the electrode radius follows the incline of the radiused channel. However, if the electrode is misaligned, the electrode end digs into the radius of the channel and may be stuck. The same factors exist if the electrode end is curved. Proper alignment helps the electrode conform to the curvature of a channel as the electrode is extended.

FIG. 36 illustrates an electrode with a shaped crimp tube 372 with an orientation feature 374 on it. In an alternative embodiment, the orientation feature is formed into the crimp tube as it is crimped/staked. The feature may be flat or angled or a series of flats and/or angles. Such features may be designed to mate with a mating feature on the mating part of the device. The orientation of the mating part may be done by a series of mated features that automatically orient the part, or by the ability of the mating part to be fixed to another mating part that is attached to the main structure of the device.

Figure 37:
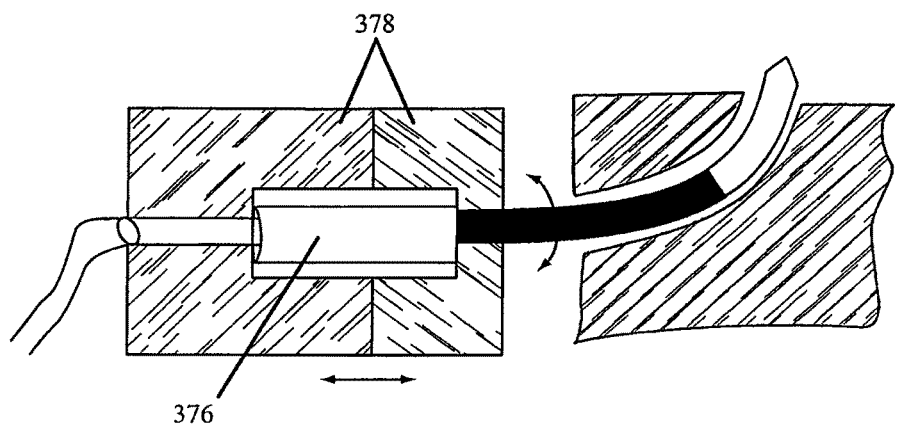
FIG. 37 illustrates a curved wire electrode with a crimp tube that is trapped between two pieces of driver parts, in accordance with one embodiment.

FIG. 37 illustrates a device with an electrode having a crimp tube 376 fixed in place in a driver part 378 of the device so that it can rotate, but not move back and forth relative to the direction of the electrode movement. As the electrode moves in the channel, features of the electrode (a radius in the end of the electrode), automatically align the electrode with the channel.

Figure 38A:
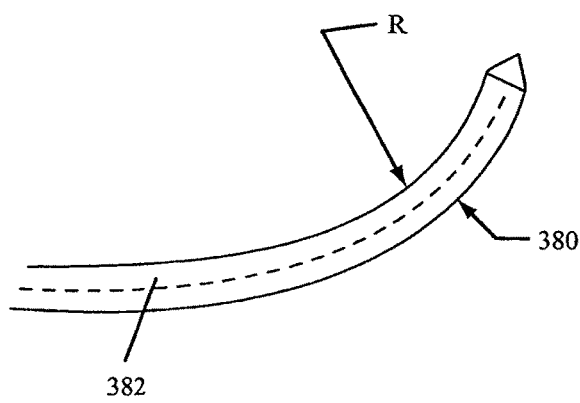
FIG. 38a illustrates a curved wire electrode having a radius of curvature, in accordance with one embodiment.
Figure 38B:
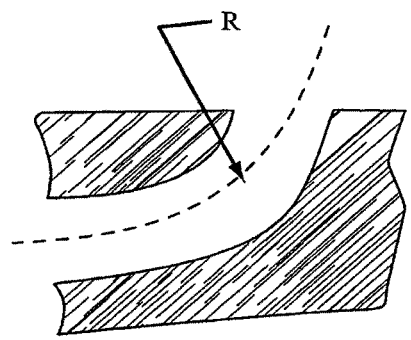
FIG. 38b illustrates a curved channel through which the electrode is deployed wherein the curved channel has the same radius of curvature as the electrode, in accordance with one embodiment.

FIGS. 38b and 38a illustrate a device channel and a complementary electrode, respectively. Moving pin electrodes may be provided with additional features to assist the tip of the electrode in following a curved channel. One embodiment has a small radius 380 of FIG. 38a in the end of the electrode 382 that matches the curvature of the channel it is trying to follow. If the radius of the bend in the electrode is smaller than the radius of the bend in the channel it is trying to follow, then the sharp tip could get stuck in the top surface of the channel. If the bend radius of the electrode is larger than the bend radius of the channel then the electrode may become stuck in the bottom surface of the channel. Accordingly, the electrode may be provided with a bend radius approximately equal the bend radius of the device channel. For example, for a channel that has a center radius of 2 mm, an electrode may have a 2 mm radius of curvature.

The bend may be formed using any suitable method. Two examples are described for illustration. One method is to non-elastically bend the end of the wire with a forming tool. This is easy and inexpensive but bending the wire non-elastically can over stress the wire and coating, causing it crack or break. Another method to place the curvature in the electrode is to place the electrode in a forming tool that is capable of withstanding the heat treating temperatures, and heat treat the electrode to the required curvature. Placing a curvature in the electrode may be assisted by attaching an orientation feature to the electrode (crimp tube) to assure that the curvature is aligned with the radius of the curvature (bend radius) in the channel the electrode is following.

Figure 39:
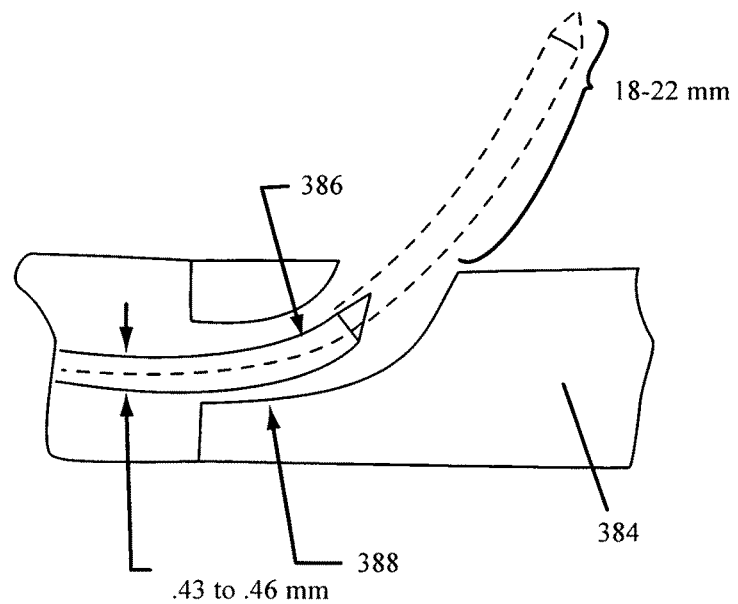
FIG. 39 illustrates a curved electrode and a matching curved channel, in accordance with one embodiment.

FIG. 39 illustrates a catheter 384 including an electrode path with a bend radius 386. As shown, a defined channel 388 is provided as an electrode path. An undersized electrode follows the electrode path to support puncture of tissue. For an approximately 0.43 mm to approximately 0.46 mm electrode diameter and desired deployment of approximately 18 to approximately 22 mm, a suitable bend radius is approximately 5 to approximately 7 mm to optimize puncture. Thus, in the embodiment shown, the bend radius 386 is approximately 5 to approximately 7 mm and the electrode channel 388 is approximately 0.8 mm diameter.

Generally, the angle of incidence of the electrode may affect the electrode insertion force into tissue. While increasing the angle of insertion, for example to approximately perpendicular to the urethra, attention may also be given to column strength. Generally, electrode configuration and deployment may account for column strength, bend radius, and incident angle. Thus, to optimize tissue puncture and repeatability of puncture, the column strength (buckling resistance) required to advance an electrode length along the angle of insertion is considered.

Figure 40A:
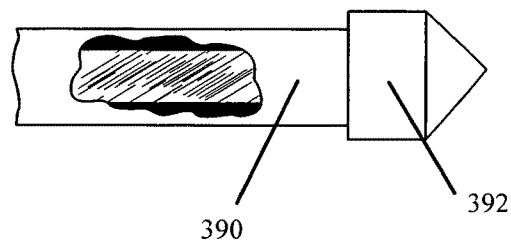
FIG. 40a illustrates a filled tube electrode with a cap attached to the end of the electrode, in accordance with one embodiment.

FIG. 40a illustrates an electrode/filled tube 390 with a cap 392 provided on one end thereof. Generally, the caps 392 are described in reference to coupling to the end of a filled tube electrode 390. In other embodiments, the caps 392 may be coupled to the end of a solid wire. In alternative embodiments, ends of the filled tube 390 (or electrode) may be welded shut, for example with a laser welder, to form a closed or round feature.

Figure 40B:
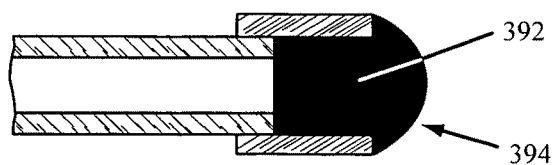
FIG. 40b illustrates a filled tube electrode with a tubular cap that has a rounded end, in accordance with one embodiment.
Figure 40C:
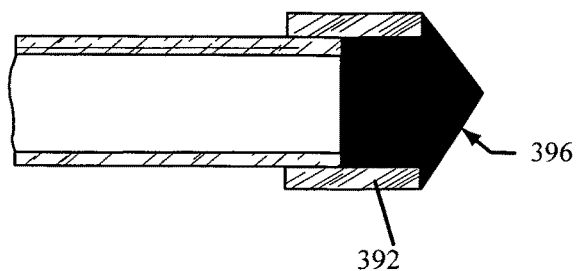
FIG. 40c illustrates a filled tube electrode with a tubular cap that has a sharp end, in accordance with one embodiment.
Figure 40D:
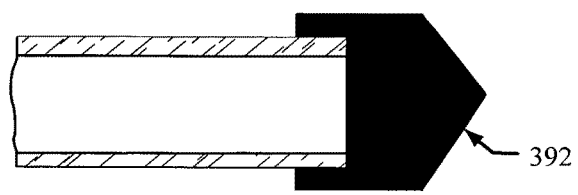
FIG. 40d illustrates a filled tube electrode with a solid cap attached to the end of the electrode, in accordance with one embodiment.
Figure 40E:
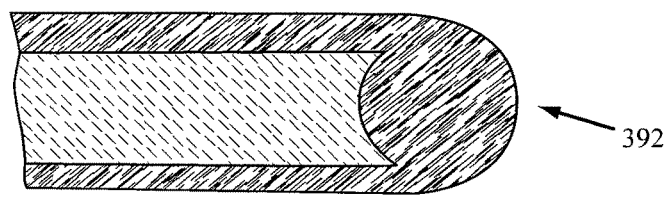
FIG. 40e illustrates a filled tube electrode with a rounded end from welding the end of the tube shut, in accordance with one embodiment.

FIGS. 40b-40d illustrate various embodiments of electrode caps 392. The electrode caps 392 may comprise an outer material and an inner material. The outer material may be insulating, conducting, or other. The inner material may be insulating or other. In some embodiments, the cap 392 may have first and second ends, with the first end being bonded or coupled to the electrode (or filled tube) and the other end formed into a round or sharp point. The first end thus may be machined or formed in a configuration for receiving the electrode. In the embodiment of FIG. 40b, the cap 392 is a tubular cap having a round second end 394. In the embodiment of FIG. 40c, the cap 392 is a tubular cap having a pointed second end 396. In the embodiment of FIG. 40d, the cap 392 is a solid material. In the embodiment of FIG. 40e, the end of the filled electrode tube is welded shut and has a rounded end.

In some embodiments, a cap or other seal may be provided on one or more ends of a tube (or electrode). In one embodiment, the cap may be formed from an insulating material and may further be filled with an insulating material. The cap may be bonded or otherwise coupled to the tube (electrode) to protect the interior of the tube, or the material from corrosion. For example, the cap may be formed from an insulating material such as polyimide, and filled with silicone, epoxy, or glue and bonded or otherwise coupled to one end of an electrode. In another embodiment, the cap comprises a thin plastic tube, such as polyimide, and is coupled to an end of the electrode and filled with a non-conductive substance such as glue, epoxy, or silicone. The cap may be filled with the non-conductive substance and then coupled to the electrode or may be coupled to the electrode and then filled with the non-conductive substance. The surface area of the exposed electrode may be decreased using a non-conductive cap.

In an alternative embodiment, the cap may be formed from a conducting material. The conducting material may be machined to a thin tube on one end and that end may be bonded to an end of an electrode to protect the interior of the tube, or the material having a high resistance to bending stress, and to corrosion. For example, the cap may be formed from a solid conductor such as platinum or platinum-iridium and bonded to an end of the electrode. A solid conductive cap does not significantly reduce the surface area of the exposed electrode. In some embodiments, a conductive cap may increase the exposed surface area.

As previously discussed, DC ablation creates hydrogen and oxygen gas during the hydrolysis process. These gases can cause the impedance from the electrode to the tissue to spike greater than about 5 k$\Omega$. In various embodiments, the system may be provided with mechanisms for venting the gases generated. Means for venting the gases may be provided within the electrodes, within the catheter, or other. Accordingly, the method for BPH treatment may further comprise venting gases created during treatment. The electrodes may be designed to be hollow and perforated so as to provide a means to vent the gases generated by DC ablation. After passing through the electrodes the gases may flow through a lumen in the catheter and emerge outside the body. Pressure may be applied from outside the body to draw out the gases.

Various design attributes may be controlled to reduce or minimize the occurrence of spikes in electrode impedance due to gas. As discussed, the concentration and rate of gas generated at a specific point of contact decreases as the surface area of each electrode increases. Thus, the length of active electrodes may be increased or maximized in contact with the tissue to be ablated. For example, in embodiments for treatment within the prostate, electrode length may be greater than approximately 3 mm. An upper limit for electrode length may be defined by the shape of the desired ablation zone. In one embodiment, electrode length is approximately 8 mm. Similarly, shape or diameter of active electrodes may be selected to increase surface area and thus decrease impedance variation. Specifically, by increasing the diameter or surface area of the shape of the electrode, the gas created is dispersed over a larger area. This facilitates venting of gas more efficiently and diffusion of gas away from the electrode. This in turn can lead to a more robust DC ablation treatment.

Figure 41:
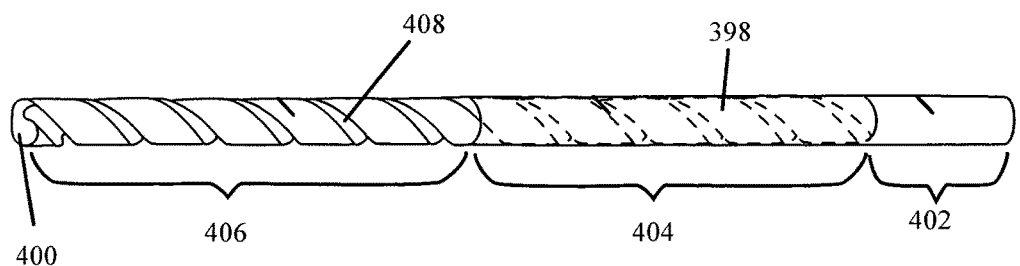
FIG. 41 illustrates an insulated electrode with one or more helical channels cut into the side of the electrode to facilitate the removal of gas produced by electrolysis in the tissue, in accordance with one embodiment.

FIG. 41 illustrates an alternative embodiment of an electrode 398 for venting gas. Removing gas from the treatment site facilitates more predictable electrode performance. The electrode 398 of FIG. 41 comprises a helical tip section 400 and does not have a significantly increased diameter when compared to standard needle electrodes. The electrode is electrically active to deliver DC current and induce necrosis in the tissue surrounding, at least, the electrode tip. As shown, the electrode 398 thus comprises an electrical connection length 402, an insulated length 404, and an active electrode length 406 (at the tip in the embodiment shown). The active electrode length 406 includes a helical channel section 408 below the external surface of the electrode. The helical channel section 408 facilitates migration of gaseous by-products of the reaction away from the reaction site. Reduction of the gas build-up reduces the likelihood of larger bubbles forming and thereby encourages lower, more constant impedance levels. In some embodiments, the helical channel may have a double helix configuration. A double helix configuration facilitates venting at the electrode tip and cuts spacing in half for gas to reach the helical undercut. The double helix channel maximizes gas channels while providing good flexibility and kink resistance. In accordance with some embodiments, the outer diameter of the electrodes ranges from approximately 0.25 mm to approximately 0.5 mm and the helical depth is approximately 15% to approximately 25% of the overall electrode diameter for each channel.

The helical channel is thus provided in the electrode tip. Deployment of the helical channel electrode in a catheter is similar to that of a straight pin electrode. The electrode maintains flexibility and thus may be directed out of the catheter at an angle between approximately 0 and approximately 90 degrees (with respect to the catheter), for example, with electrode outer diameters of approximately 0.25 to approximately 0.5 mm. Generally, the chamfered helical tip can facilitate easier insertion of the electrode into tissue, thus reducing force required to deploy out from the main body of the catheter.

In the embodiment of FIG. 41, the helical tip 400 and helical channel section 408 facilitate gas migration away from the treatment site and enhance performance by at least three actions: First, the helical tip 400 and helical channel section 408 allows a small amount of gas to stay in the channel away from the active section. Second, the helical tip 400 and helical channel section 408 allows the gas to migrate to the insulated length 404 of the electrode, and move past the insulated length 404 because there is no gas creation in the area of the insulated length 404 that would impede gas escape. Third, the helical tip 400 and helical channel section 408 allow some portion of the gas to migrate to the insulated length 404 and remain in place under an insulative layer of the insulated length (described below), thereby becoming at least somewhat stationary in an area where it will not impact the tissue reaction.

Figure 42:
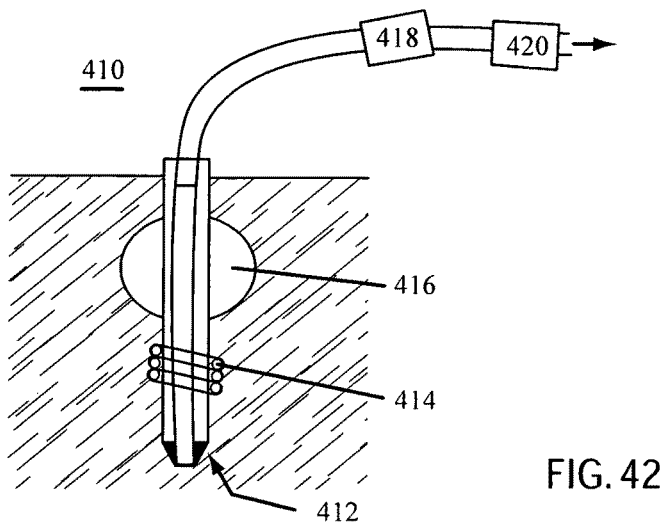
FIG. 42 illustrates a system for removing gas produced by electrolysis and incorporates a hollow electrode, in accordance with one embodiment.

FIG. 42 illustrates a further embodiment for addressing gas created during DC ablation of tissue. The embodiment shown comprises a DC ablation gas trap percutaneous electrode 410. As shown, the electrode 410 comprises an electrically active tip 412, a rigid coil 414 (for example in a chemically resistant sleeve), an expandable or inflatable ring 416, an expanding valve 418, and a controller/regulator 420. The electrically active tip delivers current to the tissue to be treated. Generally, the tip is chemically resistant. In one embodiment, the tip 412 includes a platinum coil 414 wherein the coil configuration adds retention force to the electrode. A rigid coil 414 in a chemically resistant sleeve provides sufficient stiffness to self introduce or to follow a hole made with a rigid obdurator and sleeve. The rigid coil 414 in a chemically resistant sleeve further has sufficient flexibility to follow an arduous explant path. The chemically resistant sleeve provides a coating for chemical resistance to ablation. The expandable or inflatable ring 416 is an atraumatic feature that retains the electrode 410 in position. The ring 416 as expanded substantially prevents escape of electrolysis by-products to increase the ablation zone. In some embodiments, the ring 416 may be radiographically marked to facilitate accurate placement for retention and chemical containment. The expandable/inflatable ring 416 may further be coated to improve chemical robustness. The controller/regulator 420 and expanding valve 418 cooperate to expand the expandable/inflatable ring 416. The controller/regulator 420 facilitates controlled, consistent expansion of the ring 416 to prevent tissue damage. The expanding valve 418 triggers expansion of the ring 416 through mechanical, hydraulic, pneumatic, or other expanding means.

An alternative is to use a "getter" that is activated with the electrodes to evacuate the vents inside the electrodes. The "getter" may be used in-place of a vacuum. The getter in this case may alternatively be absorbent pads located in the device 410. The getter may be designed to be discarded with the used device once the treatment is completed.

In another embodiment, the expandable/inflatable ring 416 may be surrounded by a series of electrodes spaced around its circumference. As the expandable/inflation ring expands, it forces the electrodes in contact with the tissue, assuring intimate contact between the tissue and the electrodes. The electrodes can be of one type (anode or cathode) or of alternating type (anode, cathode, anode, cathode or cathode, cathode, anode, anode).

Figure 43A:
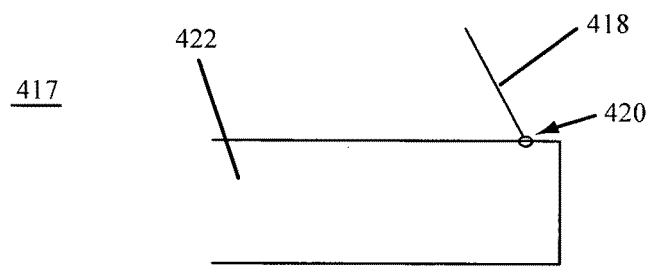
FIG. 43a illustrates a hinged electrode, in accordance with one embodiment.

FIGS. 43a-43d illustrate devices 417 wherein the electrodes 418 are hinged. FIG. 43a illustrates an embodiment with a hinge 420 at the point of intersection with the catheter 422. In other embodiments, other mechanism may be provided at the point of intersection for facilitating hinging of the electrode relative the catheter. Other mechanisms may comprise, for example, a thinned or weakened section of the electrode. The hinge mechanism facilitates flexing at the hinge.

Figure 43B:
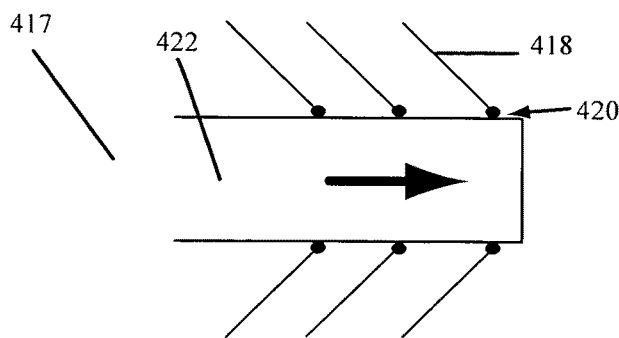
FIG. 43b illustrates a hinged electrode during insertion, in accordance with one embodiment.
Figure 43C:
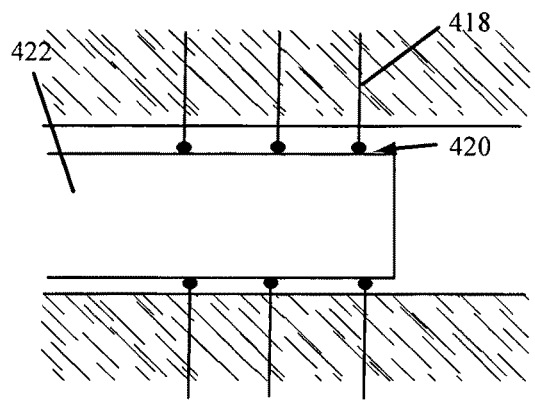
FIG. 43c illustrates a hinged electrode during penetration, in accordance with one embodiment.
Figure 43D:
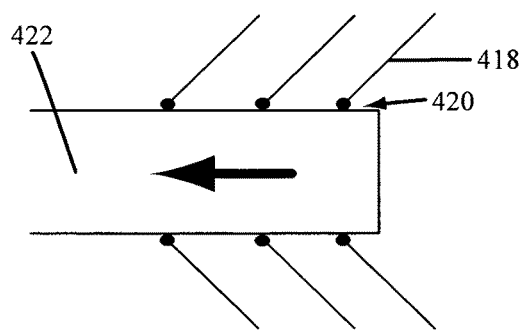
FIG. 43d illustrates a hinged electrode during withdrawal, in accordance with one embodiment.

FIG. 43b illustrates the device 417 during insertion, with the electrodes 418 flexing proximally, opposed to the direction of insertion. FIG. 43c illustrates the device 417 during penetration, with the electrodes 418 extending outwardly from the catheter 422. FIG. 43d illustrates the device 417 during withdrawal, with the electrodes 418 flexing distally, opposed to the direction of withdrawal.

As noted, in some embodiments, a Nitinol core may be coated with a material using vapor deposition. Vapor deposition provides a rough, porous outer surface with increased surface area. Particularly, coating a Nitinol core with a pinhole free Pt, TiN+C, C, TiN+IrOx, or IrOx coating using vapor deposition provides improved electrical characteristics. Thus, a corrosion resistant coating with improved electrical properties such as lower surface impedance may be provided.

In some embodiments, the electrodes may be diamond coated. The corrosion induced during DC current passing between electrodes may cause electrode fracture. By coating the electrodes with diamond, the likelihood of corrosion may be reduced. By protecting the metal portion of the electrode from body fluids, the life of the electrode can be extended.

In some embodiments, the electrodes may be bipolar consisting of two conductive surfaces that are insulated from each other. At least one electrical connection must be made to each conductive surface.

EXAMPLES

Example 1

The dose to be delivered through the electrodes can be determined by the size of the lesion required to encompass the entire tumor to be treated and the length of the conductive portion of the electrode. The volume (V) of the created lesion with amount of coulombs of charge (C) delivered may also be determined. The tissue response for the cathode will be 0.06 cc/C and 0.04 cc/C for the anode. The radius of treatment (r) can then be back calculated with the following equation where (1) is the length of the electrode.

$$V = 4/\pi * r^3 + \pi * r^2 * l$$

Figure 44:
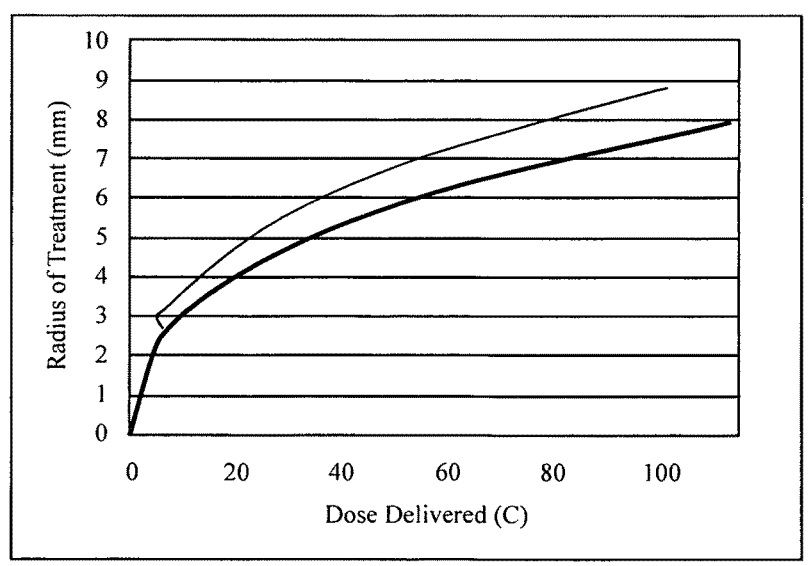
FIG. 44 illustrates the relationship between treatment radii and dose delivered for an 8 mm active electrode.

An example of a dosing chart for a 6 mm electrode is shown in FIG. 44 with an upper and lower limit on expected treatment zone radii for a given dose.

Example 2

A study was performed to assess various, impedance parameters including dose to failure, effect of length, effect of electrode type, effect of electrode diameter, effect of pin diameter, effect of insulation, effect of current and parallel paths.

The Dose to Failure evaluation showed that dose to failure is inversely proportional to length and diameter of the electrode and is proportional to the amount of venting. The following equation was determined:

$$DTF = (Gas\ Formation - Venting) * current$$

$$DTF = (1/(d*L) - (n^2 * \Delta p/l)) * i$$

Where:
DTF=Dose Time to Failure (failure is defined as the occurrence of electrical spiking in the current)
d=diameter of electrode
L=length of electrode
n=number of electrodes
Δp=pressure drop across vent
l=length of insulation
i=current at electrode Through empirical testing it was shown that as pin length and diameter increases the impedance stability of the system increases. Furthermore as the electrode surface area of the active section increases the impedance stability increases. With a constant electrode surface area of the active sections impedance stability increases with a lower magnitude of direct current or running multiple electrodes in parallel. With a constant current and electrode surface area of the active section the impedance stability increases by decreasing the insulation length from the active area back to catheter by allowing the gases to vent out of the active area.

Example 3

A study was performed to assess the corrosive properties of Nitinol and platinum-iridium-coated Nitinol wires. The study further observed the effects of Parylene-coated electrodes on electrode corrosion and tissue treatment zones.

Nitinol is commonly used in medicine and is known to corrode at the anode with applied direct current. Platinum is resistant to corrosion. Accordingly, for testing the invention disclosed herein, platinum/iridium (a combination of platinum and iridium) coated Nitinol wires have been employed.

Parylene-C coating has high electro-resistivity, is corrosion resistant, has high electrical impedance, and is impermeable to moisture. In this study, Parylene-C coating was applied to both Nitinol and platinum/iridium electrodes. The properties of the Parylene-C coating were observed.

Two tests were performed. One test used Nitinol wires for both cathode and anode. The other test used platinum/iridium-coated Nitinol wires for both cathode and anode. The electrodes were inserted into two separate gels and run for 120 coulombs at 25 mA. To confirm no corrosion of the platinum/iridium-coated Nitinol electrodes, a further test was performed that was run for 500 coulombs at 25 mA. Pictures of each electrode were taken before and after the tests in order to see changes in the appearance of the electrodes. Observations and results were documented.

Figure 45A:
FIG. 45a illustrates a Nitinol anode pin electrode with no coating before DC ablation is done.
Figure 45B:
FIG. 45b illustrates a Nitinol anode pin electrode with no coating after DC ablation is done.

FIGS. 45a and 45b illustrate the Nitinol anode before starting the test and after the test was stopped, respectively. The tests were to carry on for 120 coulombs at 25 mA. After approximately 20 minutes, the current for the Nitinol electrodes dropped to 0 (zero). This was presumably due to corrosion of the anode, as illustrated in FIG. 45b.

The Nitinol cathode had no apparent corrosion, nor did the platinum/iridium-coated electrodes. The confirmation test of 500 coulombs at 25 mA also resulted in no observable corrosion of either the platinum/iridium-coated anode or cathode.

The Parylene-C coating also was found to be a dependable insulator. The portions of the electrodes that were coated with Parylene-C were not active. No ion exchange occurred in these regions. This was observed at the start of the tests when the treatment sizes were not so big that they overlapped the coated regions. This coating also appeared to have a positive effect on impedance. It appeared that the microscopic insulation facilitated gas escape, resulting in lower impedance.

The results showed that the Nitinol anode had significant corrosion but the cathode did not. The platinum/iridium-coated Nitinol wires had no corrosion, even after further testing with 500 coulombs.

Example 4

A study was performed to determine the relationship between ease of insertion of an electrode through the urethra and the diameter of the electrode. The electrodes were inserted through the urethra, from the capsule, in pig prostates.

Two pig prostates and urethras were inserted with various diameter pin electrodes. The resulting ease of insertion to pierce through the capsule and into the urethra was subjectively judged by the individuals inserting the pins into the urethras. Pins were approximately 8 mm in length. Other methods of introducing the pin into the tissue were tried and judged relative to the initial insertion method. These methods include using a 0.5 mm diameter needle to pierce through the capsule and into the swine urethra and using a pair of tweezers to pierce and pull the tissues apart. The ease of insertion was then subjectively ranked by two individuals, each of whom did the trials independently, with a rank of 10 being the easiest to insert and a rank of 1 indicating nearly impossible to insert.

Results are shown in Table 7, below.

TABLE 7

| Insertion Method | 0.5 mm PtIr Pin | 0.8 mm PtIr Pin | 0.3 mm PtIr Coated NiTi |
|---|---|---|---|
| Normal | 6, 8 | 4, 6 | 1, 1 |
| Needle Pierced | 8, 7 | 6, 6 | 8, 1 |
| Tweezers | 8, 9 | 8, 9 | 2, 7 |

Test Subject: Subject 1 (First Number); Subject 2 (Second Number)

Both subjects ranked the diameter of electrodes in the following order: Best—0.5 mm PtIr Pin, 0.8 mm PtIr Pin, Worst—0.3 mm Par Coated pin.

The 0.5 mm diameter pin provided substantial stiffness such that the electrode did not buckle. The 0.8 mm pin did not insert as easily as the 0.5 mm pin, presumably because the created hole is larger. It is hypothesized that if the tip of the 0.8 mm pin was sharpened or tapered, it could perform as well as the 0.5 mm pin. The 0.3 mm pin provided very little stiffness or mechanical advantage and buckled. This pin was unable to be inserted.

Using a needle or tweezers to create a pilot hole was only incrementally better as it was difficult to find the hole.

Although the invention has been described with reference to specific embodiments, persons skilled in the art will recognize that changes may be made in form and detail without departing from the spirit and scope of the invention.

What is claimed is:

1. A set of low-corrosion electrodes for use with a system for non-thermal direct current ablation of a tissue that includes a power source configured to receive parameters and deliver a direct current for a period of time of about 8 minutes to less than 60 minutes to the set of low-corrosion electrodes carried by a catheter having an outer sheath substantially surrounding the catheter to generate at least two necrotic zones formed in the tissue by delivering a net electrical change that imparts at least one of a high pH and a low pH to the tissue proximate the set of electrodes, the set of low-corrosion electrodes comprising:
a set of tips including a first pair of tips and a second pair of tips, the set of tips configured for puncturing the tissue to deliver, by the direct current, the net electrical charge, each of the set of tips associated with a corresponding one of the set of low-corrosion electrodes;
a length extending between the catheter and each of the set of tips, wherein each length is configured to be guided through a corresponding channel within the catheter and each length defines a bend radius and a variable angle of incidence of each of the tips relative to the tissue to optimize tissue puncture by the set of tips, each of the lengths including:
a non-thermal electrically conductive active portion, the active portion having an inserted portion between approximately 3 mm and 12 mm long and having an outer diameter of 0.25 to 1.0 mm;
a supporting inner core; and
an outer shell having a thickness of between approximately 0.01 mm and approximately 0.25 mm;
the first pair of tips comprising:
a first electrode of the set of low-corrosion electrodes extending in a first direction from the catheter and through a corresponding aperture defined in the outer sheath; and
a second electrode of the set of low-corrosion electrodes extending in a second direction from the catheter and through a corresponding aperture defined in the outer sheath wherein the first direction and the second direction are separated by an acute angle of between approximately 15 degrees and 65 degrees due to the bend radius and the variable angle of incidence of the lengths corresponding to the first pair of tips;
the second pair of tips comprising:
a third electrode of the set of low-corrosion electrodes extending in a third direction from the catheter and through a corresponding aperture defined in the outer sheath; and
a fourth electrode of the set of low-corrosion electrodes extending in a fourth direction from the catheter and through a corresponding aperture defined in the outer sheath, wherein the third direction and the fourth direction are separated by an acute angle of between approximately 15 degrees and 65 degrees due to the bend radius and the variable angle of incidence of the lengths corresponding to the second pair of tips;
wherein the tips of each of the first, second, third, and fourth electrodes are configured for puncturing the tissue to deliver by the direct current the net electrical charge to the tissue to ablate the tissue via non-thermal direct current ablation that imparts at least one of a high pH and a low pH to the tissue proximate each of the pair of tips, and wherein each of the first pair of tips are separated from each of the second pair of tips by an obtuse angle and the outer sheath does not include any apertures arranged in the obtuse angle between the first pair of tips and the second pair of tips.

2. The set of low-corrosion electrodes of claim 1, wherein the outer shell is formed of platinum/iridium cladded to the inner core and is substantially pinhole free and is between approximately 70 to 95% platinum.

3. The set of low-corrosion electrodes of claim 1, wherein each of the lengths is pre-shaped to define the bend radius and the variable angle of incidence with a heat set or mechanical bend.

4. The set of low-corrosion electrodes of claim 1, wherein the outer shell comprises a corrosion resistant polarizing material.

5. The set of low-corrosion electrodes of claim 1, wherein each electrode has a diameter and wherein the outer shell has a thickness comprising between approximately 10 and 30% of the diameter of the electrode.

6. The set of low-corrosion electrodes of claim 1, wherein each electrode has a diameter and wherein the outer shell has a thickness comprising between approximately 5 and 50% of the diameter of the electrode.

7. The set of low-corrosion electrodes of claim 1, wherein each of the first and second pairs of tips are configured to extend up to 22 mm from the catheter to inside the tissue.

8. The set of low-corrosion electrodes of claim 1, wherein each electrode has an insulated portion.

9. The set of low-corrosion electrodes of claim 8, further comprising an adjustable insulation sleeve over the insulated portion such that the active portion of each electrode has an adjustable length.

10. The set of low-corrosion electrodes of claim 9, wherein the insulation portion has a thickness of 0.02 to 0.13 mm.

11. The set of low-corrosion electrodes of claim 9, wherein the insulation portion is thin coating of parylene or polyimide.

12. The set of low-corrosion electrodes of claim 1, wherein the active portion is proximate at least one of the pair of tips.

13. The set of low-corrosion electrodes of claim 1, wherein each electrode is bipolar and comprises an anode surface and a cathode surface.

14. The set of low-corrosion electrodes of claim 1, wherein each of the pair of tips is sharpened.

15. The set of low-corrosion electrodes of claim 1, wherein each electrode comprises a minimum bend diameter of 11.5 times the outer diameter.

16. A set of low-corrosion electrodes for use with a system for non-thermal direct current ablation of tissue including a catheter with a catheter end having an outer sheath substantially surrounding the catheter end and a means for direct current charge delivery of a direct current for a period of time of about 8 minutes to less than 60 minutes to the set of low-corrosion electrodes to generate at least two necrotic zones formed in the tissue by delivering a net electrical change that imparts at least one of a high pH and a low pH to the tissue proximate the set of low-corrosion electrodes, the set of electrodes each comprising:
a length extending between the catheter end and each of a set of tips including a first pair of tips and a second pair of tips, wherein each length is configured to be guided through a corresponding channel within the catheter end and each length defines a bend radius and a variable angle of incidence of the tip relative to the tissue to optimize tissue puncture by the tip and wherein the shape and orientation of each defined channel is configured to direct the set of low-corrosion electrodes such that each of the first pair of tips are separated from one another by an acute angle of between approximately 15 degrees and 65 degrees due to the bend radius and variable angle of incidence of the lengths corresponding to the first pair of tips, and, wherein each of the second pair of tips are separated from one another by an acute angle of between approximately 15 degrees and 65 degrees due to the bend radius and variable angle of incidence of each of the lengths corresponding to the second pair of tips, the lengths including:

a non-thermal electrically conductive active portion configured to transmit the direct current such that the at least two necrotic zones are created to form a field of treatment, the active portion having an inserted portion between approximately 3 mm and 12 mm long and having an outer diameter of approximately 0.25 to 1.0 mm, wherein the active portion is proximate at least one of the pair of tips; and an inner core and an outer shell configured so that the outer shell is cladded to the inner core and the outer shell has a thickness of between approximately 0.01 mm and approximately 0.25 mm, the first pair of tips configured for puncturing the tissue to deliver by the direct current a net positive electrical charge, a first one of the first pair of tips extending from the catheter end through a first aperture in the outer sheath in a first direction, and a second one of the first pair of tips extending from the catheter end through a second aperture in the outer sheath in a second direction, wherein the first direction and the second direction are separated by an acute angle;

the second pair of tips configured for puncturing the tissue to deliver by the direct current a net negative electrical charge while the first pair of tips delivers the net positive electrical charge, a first one of the second pair of tips extending from the catheter end through a third aperture in the outer sheath in a third direction, a second one of the second pair of tips extending from the catheter end through a fourth aperture in the outer sheath in a fourth direction, wherein the third direction and the fourth direction are separated by an acute angle, wherein each of the first direction and the second direction of the first pair of tips are separated from each of the third direction and the fourth direction of the second pair of tips by an obtuse angle, and wherein the outer sheath does not include any apertures arranged between the first pair of tips and the second pair of tips;

wherein the first pair of tips and the second pair of tips are each configured to ablate tissue therebetween via non-thermal direct current ablation that imparts at least one of a high pH and a low pH to the tissue proximate each of the pair of tips in response to the means for direct current charge delivery.

17. The set of low-corrosion electrodes of claim 16, wherein the outer shell comprises platinum/iridium comprising 70 to 95% platinum.

18. The set of low-corrosion electrodes of claim 16, wherein each of the lengths of the electrodes is pre-shaped with a slight radius to assist in deployment.

19. The set of low-corrosion electrodes of claim 16, wherein each of the pair of tips is sharpened.

20. The set of low-corrosion electrodes of claim 16, wherein each electrode has a diameter and wherein the outer shell has a thickness comprising between approximately 5 and 50% of the diameter of the electrode.

21. The set of low-corrosion electrodes of claim 16, wherein each electrode comprises a minimum bend diameter of 11.5 times the outer diameter.

22. A set of low-corrosion electrodes for use with a system for non-thermal ablation of tissue including a catheter with a catheter end having an outer sheath substantially surrounding the catheter end and a means for direct current charge delivery of a direct current for a period of time of about 8 minutes to less than 60 minutes to the set of low-corrosion electrodes to generate at least two necrotic zones formed in the tissue by delivering a net electrical change that imparts at least one of a high pH and a low pH to the tissue proximate the set of low-corrosion electrodes, the set of electrodes comprising:

a first pair of tips configured for puncturing the tissue to deliver by direct current a net positive electrical charge, a first one of the first pair of tips extending from the catheter end through a first aperture in the outer sheath in a first direction, and a second one of the first pair of tips extending from the catheter end through a second aperture in the outer sheath in a second direction, wherein the first direction and the second direction are separated by an acute angle of between approximately 15 degrees and 65 degrees;

a second pair of tips configured for puncturing the tissue to deliver by direct current a net negative electrical charge while the first pair of tips delivers the net positive electrical charge, a first one of the second pair of tips extending from the catheter end through a first aperture in the outer sheath in a third direction, a second one of the second pair of tips extending from the catheter end through a first aperture in the outer sheath in a fourth direction separated from the third direction by an acute angle of between approximately 15 degrees and 65 degrees, wherein the outer sheath does not include any apertures arranged between the apertures corresponding to the first pair of tips and the apertures corresponding to the second pair of tips;

a length extending between the catheter end and each of the pair of tips wherein each length is configured to be guided through a defined channel within the catheter end that permits a bend radius and a variable angle of incidence of the tip relative to the tissue to optimize tissue puncture by the tip, the lengths including:

a non-thermal electrically conductive active portion configured to deliver the direct current, the active portion having an inserted portion between approximately 3 mm and 12 mm long and having an outer diameter of 0.25 to 1.0 mm, wherein the electrode has a diameter and wherein the outer shell has a thickness comprising between approximately 5 and 50% of the diameter of the electrode; and each of the lengths further comprising a supporting inner core and an outer shell, wherein the first pair of tips and the second pair of tips are each configured to ablate tissue via non-thermal direct current ablation that imparts at least one of a high pH and a low pH to the tissue proximate each of the pair of tips in response to the means for direct current charge delivery.

23. The set of low-corrosion electrodes of claim 22, wherein each electrode comprises a minimum bend diameter of 11.5 times the outer diameter.

\* \* \* \* \*